(12) United States Patent
Rehwinkel et al.

(10) Patent No.: US 10,137,110 B2
(45) Date of Patent: Nov. 27, 2018

(54) 1-CYCLOHEXYL-2-PHENYLAMINO-BENZIMIDAZOLES AS MIDH1 INHIBITORS FOR THE TREATMENT OF TUMORS

(71) Applicant: Bayer Pharma Aktiengesellschaft, Berlin (DE)

(72) Inventors: Hartmut Rehwinkel, Berlin (DE); Sonja Anlauf, Wermelskirchen (DE); Duy Nguyen, Berlin (DE); Olaf Panknin, Berlin (DE); Marcus Bauser, Berlin (DE); Katja Zimmermann, Düsseldorf (DE); Stefan Kaulfuss, Berlin (DE); Roland Neuhaus, Berlin (DE); Paul Matthew Blaney, Glossop (GB); Gianna Toschi, Buxton (GB)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 15/520,384

(22) PCT Filed: Oct. 21, 2015

(86) PCT No.: PCT/EP2015/074374
§ 371 (c)(1),
(2) Date: Apr. 19, 2017

(87) PCT Pub. No.: WO2016/062770
PCT Pub. Date: Apr. 28, 2016

(65) Prior Publication Data
US 2017/0319549 A1 Nov. 9, 2017

(30) Foreign Application Priority Data
Oct. 23, 2014 (EP) .................................... 14190067

(51) Int. Cl.
*C07D 235/30* (2006.01)
*A61K 31/4184* (2006.01)
*C07D 401/04* (2006.01)
*C07D 403/04* (2006.01)
*C07D 413/04* (2006.01)

(52) U.S. Cl.
CPC ........ *A61K 31/4184* (2013.01); *C07D 235/30* (2013.01); *C07D 401/04* (2013.01); *C07D 403/04* (2013.01); *C07D 413/04* (2013.01)

(58) Field of Classification Search
CPC .................................................. C07D 235/30
See application file for complete search history.

(56) References Cited

U.S. PATENT DOCUMENTS

| 5,011,472 A | 4/1991 | Aebischer et al. |
| 5,023,252 A | 6/1991 | Hseih |
| 2017/0197921 A1 | 7/2017 | Rehwinkel et al. |
| 2017/0197922 A1 | 7/2017 | Rehwinkel et al. |
| 2017/0320861 A1 | 11/2017 | Rehwinkel et al. |

FOREIGN PATENT DOCUMENTS

| CA | 2011222 | 9/1990 |
| EP | 0385850 | 2/1990 |
| EP | 1069124 | 1/2001 |
| EP | 1810677 | 7/2007 |
| WO | WO-2000032578 | 6/2000 |
| WO | WO-2002004425 | 1/2002 |

(Continued)

OTHER PUBLICATIONS

Golub et al., Science, vol. 286, Oct. 15, 1999, pp. 531-537.*
Chemical Abstracts Registry No. 871929-10-1, indexed in the Registry file on STN CAS Online Jan. 13, 2006.*
Aiello, L.P., et al. (Dec. 1, 1994). "Vascular Endothelial Growth Factor in Ocular Fluid of Patients With Diabetic Retinopathy and Other Retinal Disorders," *The New England Journal of Medicine* 331(22): 1480-1487.
Amary, M., et al. (2011). "IDH1 and IDH2 mutations are frequent events in central chondrosarcoma and central and periosteal chondromas but not in other mesenchymal tumours," *Journal of Pathology*, 224: 334-343.
Balss, J., et al. (2008). "Analysis of the IDH1 codon 132 mutation in brain tumors," *Acta Neuropathol*, 116: 597-602.

(Continued)

*Primary Examiner* — Laura L. Stockton
(74) *Attorney, Agent, or Firm* — Morrison & Foerster LLP

(57) ABSTRACT

The present invention relates to benzimidazol-2-amines of general formula (I) in which $R^1$, $R^2$, $R^3$, $R^4$, $R^5$, $R^6$, $R^7$, $R^8$, $R^9$, $R^{10}$, $R^{11}$ and $R^{12}$ are as defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of neoplasms, as a sole agent or in combination with other active ingredients.

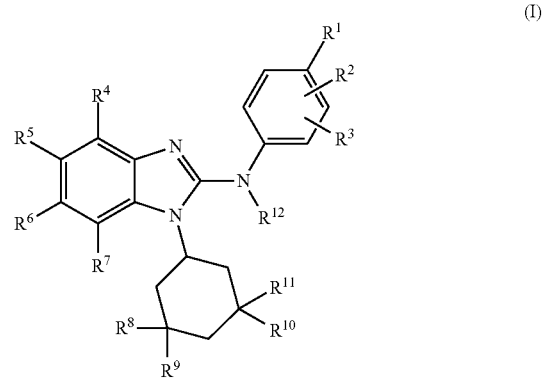

(I)

29 Claims, No Drawings

(56) References Cited

FOREIGN PATENT DOCUMENTS

| WO | WO-2002092575 | 11/2002 |
| WO | WO-2003007945 | 1/2003 |
| WO | WO-2003074515 | 9/2003 |
| WO | WO-2004085425 | 10/2004 |
| WO | WO-2005044793 | 5/2005 |
| WO | WO-2005121132 | 12/2005 |
| WO | WO-2006099379 | 9/2006 |
| WO | WO-2008153701 | 12/2008 |
| WO | WO-2009059214 | 5/2009 |
| WO | WO-2009116074 | 9/2009 |
| WO | WO-2010034796 | 4/2010 |
| WO | WO-2010100249 | 9/2010 |
| WO | WO-2010151441 | 12/2010 |
| WO | WO-2012009678 | 1/2012 |
| WO | WO-2013046136 | 4/2013 |
| WO | WO-2015121209 | 8/2015 |
| WO | WO-2015121210 | 8/2015 |
| WO | WO2015121210 | 8/2015 |
| WO | WO-2016/062677 | 4/2016 |
| WO | WO-2016/198322 | 12/2016 |
| WO | WO-2017/005674 | 1/2017 |
| WO | WO-2017/009325 | 1/2017 |
| WO | WO-2017/012967 | 1/2017 |
| WO | WO-2017/016992 | 2/2017 |
| WO | WO-2017/017046 | 2/2017 |

OTHER PUBLICATIONS

Balss, J., et al. (2012). "Enzymatic assay for quantitative analysis of (D)-2-hydroxyglutarate," *Acta Neuropathol*, 124: 883-891.

Berge, S.M., et al. (Jan. 1977). "Pharmaceutical Salts," *Journal of Pharmaceutical Sciences*, 66(1): 1-19.

Borger, D.R., et al. (2012). "Frequent Mutation of Isocitrate Dehydrogenase (IDH)1 and IDH2 in Cholangiocarcinoma Identified Through Broad-Based Tumor Genotyping," *The Oncologist*, 17: 72-79.

Cairns, R.A., et al. (2012). "IDH2 mutations are frequent in angioimmunoblastic T-cell lymphoma," *Blood Journal*, 119(8): 1901-1903.

Cross, L.C. & Klyne W. (1976). Rules for the Nomenclature of Organic Chemistry, Section E: Stereochemistry, *International Union of Pure and Applied Chemistry*, Pergamon Press, Great Britain 45: 11-30.

Dang, L., et al. (Dec. 2009). "Cancer-associated IDH1 mutations produce 2-hydroxyglutarate," *Nature* 462: 739-744.

Ghiam, A.F., et al. (2012). "Letter to the Editor, IDH mutation status in prostate cancer," *Oncogene*, 31: 3826.

Hartmann, C., et al. (2009). "Type and frequency of IDH1 and IDH2 mutations are related to astrocytic and oligodendroglial differentiation and age: a study of 1,010 diffuse gliomas," *Acta Neuropathol*, 118: 469-474.

Kranendijk, M., et al. (Oct. 15, 2010). "IDH2 Mutations in Patients with D-2-Hydroxyglutaric Aciduria," *Science*, 330: 336.

Lopez, P.F., et al. (Apr. 1996). "Transdifferentiated Retinal Pigment Epithelial Cells Are Immunoreactive for Vascular Endothelial Growth Factor in Surgically Excised Age-Related Macular Degeneration-Related Choroidal Neovascular Membranes," *Investigative Ophthalmology & Visual Science*, 37(5): 855-868.

Mardis, E.R., et al. (2009). "Recurring Mutations Found by Sequencing an Acute Myeloid Leukemia Genome," *The new England Journal of Medicine*, 361(11): 1058-1066.

Mohrenz, I.V., et al. (2013). "Isocitrate dehydrogenase 1 mutant R132H sensitizes glioma cells to BCNU-induced oxidative stress and cell death," *Apoptosis*, 18: 1416-1425.

Nema, S. et al. (Jul.-Aug. 1997). "Excipients and Their use in Injectable Products," *PDA Journal of Pharmaceutical Science & Technology*, 51(4): 166-171.

Pe'Er, J. et al. (1995). "Hypoxia-Induced Expression of Vascular Endothelial Growth factor by Retinal Cells is a Common factor in Neovascularizing Ocular Diseases," *Laboratory Investigation*, 72(6, 19): 638-645.

Powell, M.F., et al. (Sep.-Oct. 1998). "Compendium of Excipients for Parenteral Formulation," *PDA Journal of Pharmaceutical Science & Technology*, 52(5): 238-311.

Shibata, T. et al. (Mar. 2011). "Mutant IDH1 Confers an in Vivo Growth in a Melanoma Cell Line with BRAF Mutation," *The American Journal of Pathology*, 178(3): 1395-1402.

Strickley, R.G. (Nov.-Dec. 1999). "Parenteral Formulations of Small Molecules Therapeutics Marketed in the United States (1999)—Part I," *PDA Journal of Pharmaceutical Science & Technology*, 53(6): 324-349.

International Search Report dated Nov. 19, 2015 for PCT Application No. PCT/EP2015/074374, filed Oct. 21, 2015, 3 pages.

U.S. Appl. No. 15/118,154, filed Feb. 10, 2015, for Rehwinkel et al. (Also published as US-20170197921, cited herewith).

U.S. Appl. No. 15/118,157, filed Feb. 10, 2015, for Rehwinkel et al. (Also published as US-20170197922, cited herewith).

U.S. Appl. No. 15/520,385, filed Oct. 20, 2015, for Rehwinkel et al. (Also published as US-20170320861, cited herewith).

U.S. Appl. No. 15/580,372, filed Jun. 3, 2016, for Ring et al.

U.S. Appl. No. 15/742,363, filed Jul. 4, 2016, for Panknin et al.

U.S. Appl. No. 15/744,641, filed Jul. 12, 2016, for Panknin et al.

U.S. Appl. No. 15/746,352, filed Jul. 14, 2016, for Panknin et al.

U.S. Appl. No. 15/748,014, filed Jul. 22, 2016, for Schirmer.

U.S. Appl. No. 15/748,027, filed Jul. 25, 2016, for Schirmer.

\* cited by examiner

1-CYCLOHEXYL-2-PHENYLAMINO-BENZIMIDAZOLES AS MIDH1 INHIBITORS FOR THE TREATMENT OF TUMORS

CROSS REFERENCE TO RELATED APPLICATIONS

This application is the national stage of International Application No. PCT/EP2015/074374, filed internationally on Oct. 21, 2015, which claims the benefit of European Application No. 14190067.0, filed Oct. 23, 2014.

The present invention relates to benzimidazol-2-amine compounds of general formula (I) as described and defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of neoplasms, as a sole agent or in combination with other active ingredients.

BACKGROUND OF THE INVENTION

The present invention relates to chemical compounds that inhibit mutated isocitratdehydrogenase 1 (mIDH1 R132H), to methods of preparing said compounds, to pharmaceutical compositions and combinations comprising said compounds, to the use of said compounds for manufacturing a pharmaceutical composition for the treatment or prophylaxis of a disease, as well as to intermediate compounds useful in the preparation of said compounds.

Isocitrate dehydrogenases (IDH) are key enzymes in cellular metabolism, converting isocitrate to alpha-ketoglutarate and belong to 2 subgroups, defined by the utilization of different electron receptor. Two of them, isocitrate dehydrogenase 1 and 2 use NADP(+) as electron receptor. IDH1 is located in the cytoplasm and peroxisomes and IDH2 in the mitochondria as an integral part of the TCA cycle, e.g in the following reaction:

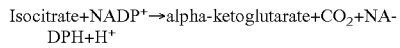

Both enzymes act as homodimers.

In a variety of tumor entities, including glioma, acute myeloid leukemia (AML), chondrosarcoma, cholangiocarcinoma, melanoma, prostate cancer, angioimmunoblastic T-cell lymphoma and others, IDH1 or IDH2 are mutated at a distinct amino acid position (Balss J. Acta Neuropathol. 2008 December; 116(6):597-602, Mardis E R, N Engl J Med. Sep. 10, 2009; 361(11):1058-66, Amary M F, J Pathol. 2011 July; 224(3):334-43, Borger D R, Oncologist. 2012; 17(1):72-9, Shibata T, Am J Pathol. 2011 March; 178(3): 1395-402, Ghiam A F, Oncogene. Aug. 16, 2012; 31(33): 3826, Cairns R A, Blood. Feb. 23, 2012; 119(8):1901-3). This mutation is always heterozygous and mutual exclusive. Most of these point mutations have been found at key positions in the catalytic domain of the enzyme (responsible 2-oxoglutarate coordination), e.g. IDH1R100, IDH1R132, IDH1G97 and IDH$_2$R$^{140,}$ IDH$_2$R172 (Dang L., Nature, Dec. 10, 2009; 462(7274):739-44). In glioma, more than 70% of all non-primary glioblastoma are IDH1 mutated and in 92.7% of the IDH1 mutated tumors the arginine was replaced by a histidine (IDH1R132H). (Hartmann C, Acta Neuropathol. 2009 October; 118(4):469-74).

The replacement of the wildtype amino acid at those catalytic residues leads to a neomorphic activity of the enzyme, converting alpha-ketoglutarate to R-2-hydroxyglutarate (2-HG). 2-HG is metabolic waste, but also an oncometabolite and it is believed to contribute to tumorgenesis (Dang L., Nature, Dec. 10, 2009; 462(7274):739-44) 2-HG is only produced in very low levels in normal cells, but cells harboring the IDH mutations produce high levels of 2-HG. High amounts of 2-HG have also been found in tumors with the IDH mutation. IDH mutations have also been described in patient with other disorders with high 2-HG levels, e.g. in a rare neurometabolic disorder characterized by supraphysiological levels of 2-HG (2-HG aciduria) (Kranendijk M, Science. Oct. 15, 2010; 330(6002):336).

Hence, the inhibition of IDH mutations and its neomorphic activity is a potential therapeutic treatment option for tumors and other IDH mutation related disorders.

WO02/092575A1 relates to benzimidazole compounds as inhibitors of membrane fusion associated events, such as transfusion.

WO03/007945A1 and WO02/04425A2 relates inter alia to benzimidazole compounds as inhibitors of RNA dependent RNA polymerases.

WO2009/059214A1 relates to Aβ-binding benzimidazole derivatives.

WO2008/153701A1 relates to benzimidazole compounds as inhibitors of KSP kinesin activity.

WO2005/121132A1 relates to fused heterocyclic compounds having anti-HCV effect.

EP0385850A2 discloses benzimidazole and azabenzimidazole derivatives for the treatment of cardiovascular diseases and duodenal ulcers.

WO00/32578 A1 discloses benzimidazole compounds as vitronectin receptor antagonists.

WO2004/085425A1 discloses inter alia benzimidazole compounds having VEGFR/KDR inhibitory activity.

EP1810677A1 discloses benzimidazole compounds as GPR40 receptor function regulators.

EP1069124A1 discloses 2-benzimidazolylamine compounds as ORL1-receptor agonists.

WO2010/034796A1 discloses benzimidazole compounds as inhibitors of enzymes belonging to the membrane-assiciated proteins in the eicosanoid and gluthathione metabolism family.

WO2009/116074A2 discloses substituted benzimidazoles as cannabinoid modulators.

WO03/074515A1 discloses benzimidazole derivatives as TIE-2 and/or VEGFR-2 inhibitors.

WO2005/044793A2 discloses inter alia benzimidazole compounds as CRF receptor antagonists.

WO2006/099379A2 discloses benzazole derivatives as beta-secretase inhibitors.

WO2010/100249A1 discloses inter alia benzimidazole compounds as inhibitors of the microsomal prostaglandin E2 synthase-1.

However, the state of the art described above does not describe the specific substituted benzimidazole compounds of general formula (I) of the present invention as defined herein, or a stereoisomer, a tautomer, an N-oxide, a hydrate, a solvate, or a salt thereof, or a mixture of same, as described and defined herein, and as hereinafter referred to as "compounds of the present invention", or their pharmacological activity.

It has now been found, and this constitutes the basis of the present invention, that said compounds of the present invention have surprising and advantageous properties.

In particular, said compounds of the present invention have been found to effectively inhibit mutated isocitratdehydrogenase 1 (mIDH1 R132H) and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, for example, haematological tumours, solid tumours, and/or metastases thereof, e.g. leukaemias and myelodysplastic syndrome, malignant lymphomas including angioimmunoblastic T-cell lymphomas, head and neck tumours including brain tumours and brain metastases (e.g. anaplastic astrocytoma, diffuse astrocytoma, glioblastoma, oligodendroglioma, secondary glioblastoma multiforme), tumours of the thorax including non-small cell and small cell lung tumours, gastrointestinal tumours including cholangiocarcinoma, endocrine tumours, mammary and other gynaecological tumours, urological tumours including renal, bladder and prostate tumours, skin tumours, and sarcomas including chondrosarcomas, and/or metastases thereof.

DESCRIPTION OF THE INVENTION

In accordance with a first aspect, the present invention covers compounds of general formula (I):

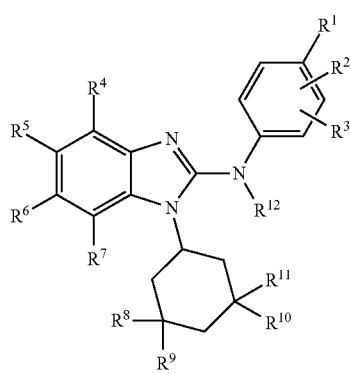

(I)

in which:
$R^1$ represents a halogen atom or group selected from:
  $C_1$-$C_6$-alkyl, $C_1$-$C_6$-alkoxy, $C_1$-$C_6$-haloalkyl, $C_1$-$C_6$-haloalkoxy, cyano, ($C_1$-$C_6$-alkyl)-S—, and ($C_1$-$C_6$-haloalkyl)-S—;
$R^2$ represents a hydrogen atom;
$R^3$ represents a hydrogen atom;
$R^4$ represents a hydrogen atom;
$R^5$ represents a phenyl or heteroaryl group; wherein said group is optionally substituted, with one or more substituents, which are independently of each other selected from:
  halo-, cyano, $C_1$-$C_6$-alkyl, $C_3$-$C_6$-cycloalkyl, $C_1$-$C_6$-haloalkyl, $C_1$-$C_6$-haloalkoxy, nitro, $R^{13}$O—, $R^{13}$S—, $R^{13}$OC(=O)—($C_1$-$C_6$-alkyl), $R^{13}$OC(=O)—($C_2$-$C_6$-alkenyl), $R^{13}$OC(=O)—($C_1$-$C_6$-alkoxy)-, $R^{14}(R^{16})$NC(=O)—($C_1$-$C_6$-alkyl)-, $R^{14}(R^{15})$NC(=O)—($C_2$-$C_6$-alkenyl)-, $R^{14}(R^{15})$NC(=O)—($C_1$-$C_6$-alkoxy)-, ($C_1$-$C_6$-alkyl)-S—, ($C_1$-$C_6$-alkyl)-S(=O)—, ($C_1$-$C_6$-alkyl)-S(=O)$_2$—, ($C_1$-$C_6$-haloalkyl)-S—, —C(=O)OR$^{13}$, —C(=O)N(R$^{14}$)R$_{15}$, —C(=O)N(R$^{14}$)S(=O)$_2$R$^{16}$, —N(R$^{14}$)R$^{15}$, —N(R$^{14}$)C(=O)R$^{16}$, —N(R$^{14}$)C(=O)R$^{17}$, —N(R$^{14}$)S(=O)$_2$R$^{16}$, —S(=O)$_2$OR$^{13}$, and —S(=O)$_2$N(R$^{14}$)R$^{15}$;

$R^6$ represents a hydrogen atom or a halogen atom or group selected from:
  $C_1$-$C_6$-alkyl, and $C_1$-$C_6$-alkoxy;
$R^7$ represents a hydrogen atom;
$R^8$ represents a $C_1$-$C_3$-alkyl group;
$R^9$, $R^{10}$, and $R^{11}$
  are independently of each other selected from: hydrogen and $C_1$-$C_3$-alkyl;
$R^{12}$ represents a hydrogen atom;
$R^{13}$ represents a hydrogen atom or a group selected from:
  $C_1$-$C_6$-alkyl, $C_3$-$C_6$-cycloalkyl, HO—($C_2$-$C_6$-alkyl)-, and ($C_1$-$C_3$-alkoxy)-($C_2$-$C_6$-alkyl)-;
$R^{14}$ and $R^{15}$
  are independently of each other selected from: hydrogen, $C_1$-$C_6$-alkyl, $C_3$-$C_6$-cycloalkyl, HO—($C_2$-$C_6$-alkyl)-, ($C_1$-$C_3$-alkoxy)-($C_2$-$C_6$-alkyl)-, $C_1$-$C_6$-haloalkyl, $H_2$N—($C_2$-$C_6$-alkyl)-, ($C_1$-$C_3$-alkyl)N(H)($C_2$-$C_6$-alkyl)-, ($C_1$-$C_3$-alkyl)$_2$N($C_2$-$C_6$-alkyl)-, $R^{13}$OC(=O)—($C_1$-$C_6$-alkyl)-, 4- to 6-membered heterocycloalkyl, phenyl, heteroaryl, phenyl-($C_1$-$C_6$-alkyl)-, and heteroaryl-($C_1$-$C_6$-alkyl)-;
  wherein phenyl and heteroaryl groups are optionally substituted with one or two substituents, which are independently of each other selected from: $C_1$-$C_3$-alkyl, $C_3$-$C_6$-cycloalkyl, $C_1$-$C_3$-alkoxy, $C_3$-$C_6$-cycloalkyloxy, $C_1$-$C_3$-haloalkyl, $C_1$-$C_3$-haloalkoxy, halogen, cyano, —C(=O)OR$^{13}$, and —C(=O)NH$_2$;
or
$R^{14}$ and $R^{15}$
  together with the nitrogen atom to which they are attached form a 4-6-membered heterocycloalkyl;
    said 4-6-membered heterocycloalkyl being optionally substituted with one substituent selected from: $C_1$-$C_3$-alkyl, $C_1$-$C_3$-haloalkyl, $C_1$-$C_3$-alkoxy, $C_1$-$C_3$-haloalkoxy, $C_3$-$C_6$-cycloalkyl, $C_3$-$C_6$-cycloalkyloxy, amino, hydroxy, halogen, and cyano;
    or said 4-6-membered heterocycloalkyl being optionally substituted with one or two halogen atoms;
$R^{16}$ represents a hydrogen atom or a group selected from:
  $C_1$-$C_6$-alkyl, HO—($C_1$-$C_6$-alkyl)-, $C_3$-$C_6$-cycloalkyl, HO—($C_3$-$C_6$-cycloalkyl)-, $C_1$-$C_6$-haloalkyl, ($C_1$-$C_3$-alkoxy)-($C_1$-$C_6$-alkyl), phenyl, heteroaryl, and 4- to 6-membered heterocycloalkyl;
  wherein phenyl and heteroaryl groups are optionally substituted with one or two substituents, which are independently of each other selected from: $C_1$-$C_3$-alkyl, $C_3$-$C_6$-cycloalkyl, $C_1$-$C_3$-alkoxy, $C_3$-$C_6$-cycloalkyloxy, $C_1$-$C_3$-haloalkyl, $C_1$-$C_3$-haloalkoxy, halogen, cyano, —C(=O)OR$^{13}$, and —C(=O)N(R$^{14}$)R$^{15}$;
$R^{17}$ represents a group selected from: —N(R$^{14}$)R$^{15}$ and $C_1$-$C_6$-alkoxy;
or a stereoisomer, a tautomer, an N-oxide, a hydrate, a solvate, or a salt thereof, or a mixture of same.

The terms as mentioned in the present text have preferably the following meanings:

The term "halogen atom", "halo-" or "Hal-" is to be understood as meaning a fluorine, chlorine, bromine or iodine atom.

The term "$C_1$-$C_6$-alkyl" is to be understood as preferably meaning a linear or branched, saturated, monovalent hydrocarbon group having 1, 2, 3, 4, 5, or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl- or iso-propyl group.

The term "—$C_1$-$C_8$-alkylene-" is understood as preferably meaning a bivalent, linear or branched, saturated hydrocarbon chain (or "tether") having 1, 2, 3, 4, 5, 6, 7 or 8 carbon atoms, e.g. —$CH_2$— ("methylene" or "—$C_1$-alkylene-") or, for example —$CH_2$—$CH_2$— ("ethylene" or "—$C_2$-alkylene-"), —$CH_2$—$CH_2$—$CH_2$—, —C(H)($CH_3$)—$CH_2$— or —C($CH_3$)$_2$— ("propylene" or "—$C_3$-alkylene-"), or, for example —$CH_2$—C(H)($CH_3$)—$CH_2$—, —$CH_2$—C($CH_3$)$_2$—), —$CH_2$—$CH_2$—$CH_2$—$CH_2$— ("butylene" or "—$C_4$-alkylene-"), "—$C_5$-alkylene-", e.g. —$CH_2$—$CH_2$—$CH_2$—$CH_2$—$CH_2$— ("n-pentylene"), or "—$C_6$-alkylene-", e.g. —$CH_2$—$CH_2$—$CH_2$—$CH_2$—$CH_2$—$CH_2$— ("n-hexylene") group. Particularly, said alkylene tether has 1, 2, 3, 4, or 5 carbon atoms ("—$C_1$-$C_5$-alkylene-"), more particularly 1 or 2 carbon atoms ("—$C_1$-$C_2$-alkylene-"), or, 3, 4, or 5 carbon atoms ("—$C_3$-$C_5$-alkylene-").

The term "$C_1$-$C_6$-haloalkyl" is to be understood as preferably meaning a linear or branched, saturated, monovalent hydrocarbon group in which the term "$C_1$-$C_6$-alkyl" is defined supra, and in which one or more hydrogen atom is replaced by a halogen atom, in identically or differently, i.e. one halogen atom being independent from another. Particularly, said halogen atom is F. Said $C_1$-$C_6$-haloalkyl group is, for example, —$CF_3$, —$CHF_2$, —$CH_2F$, —$CF_2CF_3$, $CH_2CH_2F$, $CH_2CHF_2$, $CH_2CF_3$, or $CH_2CH_2CF_3$.

The term "$C_1$-$C_6$-alkoxy" is to be understood as preferably meaning a linear or branched, saturated, monovalent, group of formula —O—($C_1$-$C_6$-alkyl), in which the term "$C_1$-$C_6$-alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "$C_1$-$C_6$-haloalkoxy" is to be understood as preferably meaning a linear or branched, saturated, monovalent $C_1$-$C_6$-alkoxy group, as defined supra, in which one or more of the hydrogen atoms is replaced, in identically or differently, by a halogen atom. Particularly, said halogen atom is F. Said $C_1$-$C_6$-haloalkoxy group is, for example, —$OCF_3$, —$OCHF_2$, —$OCH_2F$, —$OCF_2CF_3$, or —$OCH_2CF_3$.

The term "$C_2$-$C_6$-alkenyl" is to be understood as preferably meaning a linear or branched, monovalent hydrocarbon group, which contains one or more double bonds, and which has 2, 3, 4, 5 or 6 carbon atoms, particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl)ethenyl, buta-1,3-dienyl, penta-1,4-dienyl, hexa-1,5-dienyl, or methylhexadienyl group. Particularly, said group is vinyl or allyl.

The term "$C_3$-$C_6$-cycloalkyl" is to be understood as meaning a saturated, monovalent, monocyclic hydrocarbon ring which contains 3, 4, 5 or 6 carbon atoms. Said $C_3$-$C_6$-cycloalkyl group is for example, a monocyclic hydrocarbon ring, e.g. a cyclopropyl, cyclobutyl, cyclopentyl or cyclohexyl ring.

The term "$C_3$-$C_6$-cycloalkyloxy" is to be understood as meaning a saturated, monovalent, monocyclic hydrocarbon group of formula —O—($C_3$-$C_6$-cycloalkyl), in which the term "$C_3$-$C_6$-cycloalkyl" is defined supra, e.g. a. a cyclopropyloxy, cyclobutyloxy, cyclopentyloxy or cyclohexyloxy group.

The term "4- to 6-membered heterocycloalkyl", is to be understood as meaning a saturated, monovalent, monocyclic hydrocarbon ring which contains 3, 4 or 5 carbon atoms, and one or two heteroatom-containing groups selected from: O, S, S(=O), S(=O)$_2$, NH, and C(=O); wherein a 4-membered heterocycloalkyl group contains only one heteroatom-containing group selected from: O, S, S(=O), S(=O)$_2$, NH, and C(=O). Said 4- to 6-membered heterocycloalkyl group is attached to the rest of the molecule via any one of the carbon atoms or, if present, a nitrogen atom.

Particularly, without being limited thereto, said heterocycloalkyl can be a 4-membered ring, such as azetidinyl or oxetanyl, or a 5-membered ring, such as tetrahydrofuranyl, dioxolinyl, pyrrolidinyl, imidazolidinyl or pyrazolidinyl, or a 6-membered ring, such as tetrahydropyranyl, piperidinyl, morpholinyl, dithianyl, thiomorpholinyl or piperazinyl.

The term "heteroaryl" is understood as preferably meaning a monovalent, monocyclic, bicyclic or tricyclic aromatic ring system having 5, 6, 7, 8, 9, 10, 11, 12, 13 or 14 ring atoms (a "5- to 14-membered heteroaryl" group), particularly 5 or 6 or 9 or 10 atoms, and which contains at least one heteroatom which may be identical or different, said heteroatom being such as oxygen, nitrogen or sulfur, and in addition in each case can be benzocondensed. Particularly, heteroaryl is selected from: thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl, benzofuranyl, benzothienyl, benzoxazolyl, benzisoxazolyl, benzimidazolyl, benzotriazolyl, indazolyl, indolyl, isoindolyl, pyridinyl, pyridazinyl, pyrimidinyl, pyrazinyl, triazinyl, quinolinyl, quinazolinyl, isoquinolinyl, azocinyl, indolizinyl, purinyl, cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, and oxepinyl.

In general, and unless otherwise mentioned, the heteroaryl group includes all the possible isomeric forms thereof, e.g. the positional isomers thereof. Thus, for some illustrative non-restricting example, the term pyridinyl includes pyridin-2-yl, pyridin-3-yl, and pyridin-4-yl; or the term thienyl includes thien-2-yl, and thien-3-yl.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, particularly $C_1$-$C_2$, $C_1$-$C_3$, $C_1$-$C_4$, $C_1$-$C_6$, more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkyl", and "$C_2$-$C_6$-alkenyl" is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$, particularly $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

Should a substituent be composed of more than one part, as in case of e.g. ($C_1$-$C_4$-alkoxy)-($C_1$-$C_4$-alkyl)-, a hyphen at the beginning or at the end of the substituent marks the point of attachment to the rest of the molecule.

Ring system substituent means a substituent attached to an aromatic or nonaromatic ring system which, for example, replaces an available hydrogen on the ring system.

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, and (4-methoxy-benzene)sulfonyloxy.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence is preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of this invention optionally contain one or more asymmetric centre, depending upon the location and nature of the various substituents desired.

Asymmetric carbon atoms is present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds. The compounds of the present invention optionally contain sulphur atoms which are asymmetric, such as an asymmetric sulfoxide, of structure:

for example, in which * indicates atoms to which the rest of the molecule can be bound.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. R- or S-isomers, or E- or Z-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers. Another example concerns dihydroxyoxazoles which can exist as tautomers as well, two of which are shown below:

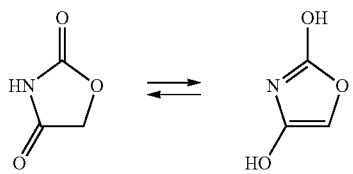 [SMILES: O=C1COC(=O)N1 ; Oc1coc(O)n1]

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19. A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "x HCl", "x CF$_3$COOH", "x Na$^+$", for example, are to be understood as not a stoichiometric specification, but solely as a salt form.

This applies analogously to cases in which synthesis intermediates or example compounds or salts thereof have been obtained, by the preparation and/or purification processes described, as solvates, such as hydrates with (if defined) unknown stoichiometric composition.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorph, or as a mixture of more than one polymorph, in any ratio.

The present invention covers compounds of general formula (I), supra, in which $R^1$ represents a halogen atom or group selected from: $C_1$-$C_6$-alkyl, $C_1$-$C_6$-alkoxy, $C_1$-$C_6$-haloalkyl, $C_1$-$C_6$-haloalkoxy, cyano, ($C_1$-$C_6$-alkyl)-S—, and ($C_1$-$C_6$-haloalkyl)-S—.

In a preferred embodiment, the present invention relates to compounds of general formula (I), supra, in which $R^1$ represents a group selected from: $C_1$-$C_6$-alkyl, $C_1$-$C_6$-alkoxy, $C_1$-$C_6$-haloalkyl, $C_1$-$C_6$-haloalkoxy, ($C_1$-$C_6$-alkyl)-S—, and ($C_1$-$C_6$-haloalkyl)-S—.

In another preferred embodiment, the present invention relates to compounds of general formula (I), supra, in which $R^1$ represents a group selected from: $C_1$-$C_6$-haloalkyl, $C_1$-$C_6$-haloalkoxy, and ($C_1$-$C_6$-haloalkyl)-S—.

In another preferred embodiment, the present invention relates to compounds of general formula (I), supra, in which $R^1$ represents a group selected from: $C_1$-$C_3$-alkyl, $C_1$-$C_3$-alkoxy, $C_1$-$C_3$-haloalkyl, $C_1$-$C_3$-haloalkoxy, ($C_1$-$C_3$-alkyl)-S—, and ($C_1$-$C_3$-haloalkyl)-S—.

In another preferred embodiment, the present invention relates to compounds of general formula (I), supra, in which $R^1$ represents a group selected from: $C_1$-$C_3$-haloalkyl, $C_1$-$C_3$-haloalkoxy, and ($C_1$-$C_3$-haloalkyl)-S—.

In another preferred embodiment, the present invention relates to compounds of general formula (I), supra, in which $R^1$ represents a group selected from: ethyl, ethoxy, cyano, —CF$_3$, —OCF$_3$, —SCF$_3$, iso-propyl, iso-propoxy, and —OCHF$_2$.

In another preferred embodiment, the present invention relates to compounds of general formula (I), supra, in which $R^1$ represents a group selected from: ethyl, ethoxy-, —OCF$_3$, iso-propyl, iso-propoxy, and —OCHF$_2$.

In another preferred embodiment, the present invention relates to compounds of general formula (I), supra, in which $R^1$ represents a group selected from: —OCF$_3$, and —OCHF$_2$.

In another preferred embodiment, the present invention relates to compounds of general formula (I), supra, in which $R^1$ represents a group selected from: ethyl, ethoxy, iso-propyl, and iso-propoxy.

In another preferred embodiment, the present invention relates to compounds of general formula (I), supra, in which $R^1$ represents a group selected from: —OCF$_3$, —SCF$_3$, and —CF$_3$.

The present invention covers compounds of general formula (I), supra, in which $R^5$ represents a phenyl or heteroaryl group; wherein said group is optionally substituted, with one or more substituents, which are independently of each other selected from: halo-, cyano, $C_1$-$C_6$-alkyl, $C_3$-$C_6$-cycloalkyl, $C_1$-$C_6$-haloalkyl, $C_1$-$C_6$-haloalkoxy, nitro, $R^{13}$O—, $R^{13}$S—, $R^{13}$OC(=O)—($C_1$-$C_6$-alkyl)-, $R^{13}$OC(=O)—($C_2$-$C_6$-alkenyl)-, $R^{13}$OC(=O)—($C_1$-$C_6$-alkoxy)-, $R^{14}$($R^{15}$)NC(=O)—($C_1$-$C_6$-alkyl)-, $R^{14}$($R^{15}$)NC(=O)—($C_2$-$C_6$-alkenyl)-, $R^{14}$($R^{15}$)NC(=O)—($C_1$-$C_6$-alkoxy)-, ($C_1$-$C_6$-alkyl)-S—, ($C_1$-$C_6$-alkyl)-S(=O)—, ($C_1$-$C_6$-alkyl)-S(=O)$_2$—, ($C_1$-$C_6$-haloalkyl)-S—, —C(=O)O$R^{13}$, —C(=O)N($R^{14}$)$R^{15}$, —C(=O)N($R^{14}$)S(=O)$_2$$R^{16}$, —N($R^{14}$)$R^{15}$, —N($R^{14}$)C(=O)$R^{16}$, —N($R^{14}$)C(=O)$R^{17}$, —N($R^{14}$)S(=O)$_2$$R^{16}$, —S(=O)$_2$O$R^{13}$, and —S(=O)$_2$N($R^{14}$)$R^{15}$.

In a preferred embodiment, the present invention relates to compounds of general formula (I), supra, in which $R^5$ represents a phenyl or heteroaryl group; wherein said group is optionally substituted, with one or more substituents, which are independently of each other selected from: halo-, cyano, $C_1$-$C_6$-alkyl, $C_1$-$C_6$-haloalkyl, $C_1$-$C_6$-haloalkoxy, $R^{13}O-$, $R^{13}S-$, $(C_1-C_6\text{-alkyl})-S-$, $(C_1-C_6\text{-alkyl})-S(=O)-$, $(C_1-C_6\text{-alkyl})-S(=O)_2-$, $(C_1-C_6\text{-haloalkyl})-S-$, $-C(=O)OR^{13}$, and $-C(=O)N(R^{14})R^{15}$.

In another preferred embodiment, the present invention relates to compounds of general formula (I), supra, in which $R^5$ represents a phenyl or heteroaryl group; wherein said group is optionally substituted, with one or more substituents, which are independently of each other selected from: halo-, cyano, $C_1-C_3$-alkyl, $C_1-C_3$-haloalkyl, $C_1-C_3$-haloalkoxy, $R^{13}O-$, $R^{13}S-$, $(C_1-C_3\text{-alkyl})-S-$, $(C_1-C_3\text{-alkyl})-S(=O)-$, $(C_1-C_3\text{-alkyl})-S(=O)_2-$, $(C_1-C_3\text{-haloalkyl})-S-$, $-C(=O)OR^{13}$, and $-C(=O)N(R^{14})R^{15}$.

In another preferred embodiment, the present invention relates to compounds of general formula (I), supra, in which $R^5$ represents a phenyl or heteroaryl group; wherein said group is optionally substituted, with one or more substituents, which are independently of each other selected from: halo-, $C_1-C_3$-alkyl, $C_1-C_3$-haloalkyl, $R^{13}O-$, $-C(=O)OR^{13}$, and $-C(=O)N(R^{14})R^{15}$.

In another preferred embodiment, the present invention relates to compounds of general formula (I), supra, in which $R^5$ represents a phenyl or heteroaryl group; wherein said group is optionally substituted, with one, two or three substituents, which are independently of each other selected from: halo-, $C_1-C_3$-alkyl, $C_1-C_3$-haloalkyl, $R^{13}O-$, $-C(=O)OR^{13}$, and $-C(=O)N(R^{14})R^{15}$.

In another preferred embodiment, the present invention relates to compounds of general formula (I), supra, in which $R^5$ represents an phenyl or heteroaryl group; wherein said group is optionally substituted, with one or more substituents, which are independently of each other selected from: halo-, cyano-, $C_1-C_6$-alkyl, $C_3-C_6$-cycloalkyl, $C_1-C_6$-haloalkyl, $C_1-C_6$-haloalkoxy, nitro, $R^{13}O-$, $R^{13}S-$, $R^{13}OC(=O)-(C_1-C_6\text{-alkyl})-$, $R^{13}OC(=O)-(C_2-C_6\text{-alkenyl})$, $R^{13}OC(=O)-(C_1-C_6\text{-alkoxy})-$, $R^{14}(R^{15})NC(=O)-(C_1-C_6\text{-alkyl})-$, $R^{14}(R^{15})NC(=O)-(C_2-C_6\text{-alkenyl})-$, $R^{14}(R^{15})NC(=O)-(C_1-C_6\text{-alkoxy})-$, $(C_1-C_6\text{-alkyl})-S-$, $(C_1-C_6\text{-alkyl})-S(=O)-$, $(C_1-C_6\text{-alkyl})-S(=O)_2-$, $(C_1-C_6\text{-haloalkyl})-S-$, $-C(=O)OR^{13}$, $-C(=O)N(R^{14})R^{15}$, $-C(=O)N(R^{14})S(=O)_2R^{16}$, $-N(R^{14})R^{15}$, $-N(R^{14})C(=O)R^{16}$, $-N(R^{14})C(=O)R^{17}$, $-N(R^{14})S(=O)_2R^{16}$, $-S(=O)_2OR^{13}$, and $-S(=O)_2N(R^{14})R^{15}$; wherein said heteroaryl group is selected from: thienyl, furanyl, pyrrolyl, oxazolyl, thiazolyl, imidazolyl, pyrazolyl, isoxazolyl, isothiazolyl, oxadiazolyl, triazolyl, tetrazolyl, thiadiazolyl, thia-4H-pyrazolyl, benzofuranyl, benzothienyl, benzoxazolyl, benzisoxazolyl, benzimidazolyl, benzotriazolyl, indazolyl, indolyl, isoindolyl, pyridinyl, pyridazinyl, pyrimidinyl, pyrazinyl, triazinyl, quinolinyl, quinazolinyl, isoquinolinyl, azocinyl, indolizinyl, purinyl, cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, and oxepinyl.

In another preferred embodiment, the present invention relates to compounds of general formula (I), supra, in which $R^5$ represents a phenyl or heteroaryl group; wherein said group is optionally substituted, with one or more substituents, which are independently of each other selected from: halo-, cyano, $C_1-C_6$-alkyl, $C_3-C_6$-cycloalkyl, $C_1-C_6$-haloalkyl, $C_1-C_6$-haloalkoxy, nitro, $R^{13}O-$, $R^{13}S-$, $R^{13}OC(=O)-(C_1-C_6\text{-alkyl})-$, $R^{13}OC(=O)-(C_2-C_6\text{-alkenyl})$, $R^{13}OC(=O)-(C_1-C_6\text{-alkoxy})-$, $R^{14}(R^{15})NC(=O)-(C_1-C_6\text{-alkyl})-$, $R^{14}(R^{15})NC(=O)-(C_2-C_6\text{-alkenyl})-$, $R^{14}(R^{15})NC(=O)-(C_1-C_6\text{-alkoxy})-$, $(C_1-C_6\text{-alkyl})-S-$, $(C_1-C_6\text{-alkyl})-S(=O)-$, $(C_1-C_6\text{-alkyl})-S(=O)_2-$, $(C_1-C_6\text{-haloalkyl})-S-$, $-C(=O)OR^{13}$, $-C(=O)N(R^{14})R^{15}$, $-C(=O)N(R^{14})S(=O)_2R^{16}$, $-N(R^{14})R^{15}$, $-N(R^{14})C(=O)R^{16}$, $-N(R^{14})C(=O)R^{17}$, $-N(R^{14})S(=O)_2R^{16}$, $-S(=O)_2OR^{13}$, and $-S(=O)_2N(R^{14})R^{15}$; wherein said heteroaryl group is selected from: thienyl, furanyl, pyrrolyl, oxazolyl, thiazolyl, imidazolyl, pyrazolyl, isoxazolyl, isothiazolyl, oxadiazolyl, triazolyl, tetrazolyl, thiadiazolyl, thia-4H-pyrazolyl, pyridinyl, pyridazinyl, pyrimidinyl, pyrazinyl, and triazinyl.

In another preferred embodiment, the present invention relates to compounds of general formula (I), supra, in which $R^5$ represents a phenyl or heteroaryl group; wherein said group is optionally substituted, with one or more substituents, which are independently of each other selected from: halo-, cyano, $C_1-C_6$-alkyl, $C_3-C_6$-cycloalkyl, $C_1-C_6$-haloalkyl, $C_1-C_6$-haloalkoxy, nitro, $R^{13}O-$, $R^{13}S-$, $R^{13}OC(=O)-(C_1-C_6\text{-alkyl})-$, $R^{13}OC(=O)-(C_2-C_6\text{-alkenyl})-$, $R^{13}OC(=O)-(C_1-C_6\text{-alkoxy})-$, $R^{14}(R^{15})NC(=O)-(C_1-C_6\text{-alkyl})-$, $R^{14}(R^{15})NC(=O)-(C_2-C_6\text{-alkenyl})-$, $R^{14}(R^{15})NC(=O)-(C_1-C_6\text{-alkoxy})-$, $(C_1-C_6\text{-alkyl})-S-$, $(C_1-C_6\text{-alkyl})-S(=O)-$, $(C_1-C_6\text{-alkyl})-S(=O)_2-$, $(C_1-C_6\text{-haloalkyl})-S-$, $-C(=O)OR^{13}$, $-C(=O)N(R^{14})R^{15}$, $-C(=O)N(R^{14})S(=O)_2R^{16}$, $-N(R^{14})R^{15}$, $-N(R^{14})C(=O)R^{16}$, $-N(R^{14})C(=O)R^{17}$, $-N(R^{14})S(=O)_2R^{16}$, $-S(=O)_2OR^{13}$, and $-S(=O)_2N(R^{14})R^{15}$; wherein said heteroaryl group is selected from: oxazolyl, pyrazolyl, oxadiazolyl, triazolyl, tetrazolyl, and pyridinyl.

In another preferred embodiment, the present invention relates to compounds of general formula (I), supra, in which $R^5$ represents a phenyl or heteroaryl group; wherein said group is optionally substituted, with one or more substituents, which are independently of each other selected from: halo-, cyano, $C_1-C_6$-alkyl, $C_3-C_6$-cycloalkyl, $C_1-C_6$-haloalkyl, $C_1-C_6$-haloalkoxy, nitro, $R^{13}O-$, $R^{13}S-$, $R^{13}OC(=O)-(C_1-C_6\text{-alkyl})-$, $R^{13}OC(=O)-(C_2-C_6\text{-alkenyl})-$, $R^{13}OC(=O)-(C_1-C_6\text{-alkoxy})-$, $R^{14}(R^{15})NC(=O)-(C_1-C_6\text{-alkyl})-$, $R^{14}(R^{15})NC(=O)-(C_2-C_6\text{-alkenyl})-$, $R^{14}(R^{15})NC(=O)-(C_1-C_6\text{-alkoxy})-$, $(C_1-C_6\text{-alkyl})-S-$, $(C_1-C_6\text{-alkyl})-S(=O)-$, $(C_1-C_6\text{-alkyl})-S(=O)_2-$, $(C_1-C_6\text{-haloalkyl})-S-$, $-C(=O)OR^{13}$, $-C(=O)N(R^{14})R^{15}$, $-C(=O)N(R^{14})S(=O)_2R^{16}$, $-N(R^{14})R^{15}$, $-N(R^{14})C(=O)R^{16}$, $-N(R^{14})C(=O)R^{17}$, $-N(R^{14})S(=O)_2R^{16}$, $-S(=O)_2OR^{13}$, and $-S(=O)_2N(R^{14})R^{15}$; wherein said heteroaryl group is selected from: 1,2-oxazol-4-yl, 1,3-oxazol-5-yl, 1H-pyrazol-4-yl, 1H-pyrazol-5-yl, pyridin-4-yl, 1,3,4-oxadiazol-2-yl, 1,2,4-oxadiazol-3-yl, 1H-tetrazol-5-yl, 1,2,4-triazol-3-yl, and 1,3,4-oxadiazol-2-yl.

In another preferred embodiment, the present invention relates to compounds of general formula (I), supra, in which $R^5$ represents a phenyl or heteroaryl group; wherein said group is optionally substituted, with one or more substituents, which are independently of each other selected from: halo-, $C_1-C_6$-alkyl, $C_1-C_6$-haloalkyl, $R^{13}O-$, $-C(=O)OR^{13}$, and $-C(=O)N(R^{14})R^{15}$; wherein said heteroaryl group is selected from: thienyl, furanyl, pyrrolyl, oxazolyl, thiazolyl, imidazolyl, pyrazolyl, isoxazolyl, isothiazolyl, oxadiazolyl, triazolyl, tetrazolyl, thiadiazolyl, thia-4H-pyrazolyl, pyridinyl, pyridazinyl, pyrimidinyl, pyrazinyl, and triazinyl.

In another preferred embodiment, the present invention relates to compounds of general formula (I), supra, in which $R^5$ represents a phenyl or heteroaryl group; wherein said group is optionally substituted, with one, two or three substituents, which are independently of each other selected from: halo-, $C_1-C_3$-alkyl, $C_1-C_3$-haloalkyl, $R^{13}O-$, $-C(=O)OR^{13}$, and $-C(=O)N(R^{14})R^{15}$; wherein said heteroaryl group is selected from: thienyl, furanyl, pyrrolyl, oxazolyl, thiazolyl, imidazolyl, pyrazolyl, isoxazolyl, isothiazolyl, oxadiazolyl, triazolyl, tetrazolyl, thiadiazolyl, thia-4H-pyrazolyl, pyridinyl, pyridazinyl, pyrimidinyl, pyrazinyl, and triazinyl.

In another preferred embodiment, the present invention relates to compounds of general formula (I), supra, in which $R^5$ represents a phenyl or heteroaryl group; wherein said group is optionally substituted, with one or more substituents, which are independently of each other selected from: halo-, $C_1$-$C_6$-alkyl, $C_1$-$C_6$-haloalkyl, $R^{13}O$—, —C(=O) $OR^{13}$, and —C(=O)N($R^{14}$)$R^{15}$; wherein said heteroaryl group is selected from: oxazolyl, pyrazolyl, oxadiazolyl, triazolyl, tetrazolyl, and pyridinyl.

In another preferred embodiment, the present invention relates to compounds of general formula (I), supra, in which $R^5$ represents a phenyl or heteroaryl group; wherein said group is optionally substituted, with one or more substituents, which are independently of each other selected from: halo-, $C_1$-$C_3$-alkyl, $C_1$-$C_3$-haloalkyl, $R^{13}O$—, —C(=O) $OR^{13}$, and —C(=O)N($R^{14}$)$R^{15}$; wherein said heteroaryl group is selected from: oxazolyl, pyrazolyl, oxadiazolyl, triazolyl, tetrazolyl, and pyridinyl.

In another preferred embodiment, the present invention relates to compounds of general formula (I), supra, in which $R^5$ represents a phenyl or heteroaryl group; wherein said group is optionally substituted, with one, two or three substituents, which are independently of each other selected from: fluoro, methyl, methoxy, ethoxy, hydroxy, —CF$_3$, —C(=O)OH, —C(=O)OCH$_3$, and —C(=O)NH$_2$; wherein said heteroaryl group is selected from: oxazolyl, pyrazolyl, oxadiazolyl, triazolyl, tetrazolyl, and pyridinyl.

The present invention covers compounds of general formula (I), supra, in which $R^6$ represents a hydrogen atom or a halogen atom or group selected from: $C_1$-$C_6$-alkyl, and $C_1$-$C_6$-alkoxy.

In a preferred embodiment, the present invention relates to compounds of general formula (I), supra, in which $R^6$ represents a hydrogen atom or a halogen atom or group selected from: $C_1$-$C_3$-alkyl, and $C_1$-$C_3$-alkoxy.

In a preferred embodiment, the present invention relates to compounds of general formula (I), supra, in which $R^6$ represents a hydrogen atom or a $C_1$-$C_3$-alkyl group.

In a preferred embodiment, the present invention relates to compounds of general formula (I), supra, in which $R^6$ represents a hydrogen atom or a methyl group.

In a preferred embodiment, the present invention relates to compounds of general formula (I), supra, in which $R^6$ represents a hydrogen atom group.

The present invention covers compounds of general formula (I), supra, in which $R^8$ represents a $C_1$-$C_3$-alkyl group.

In a preferred embodiment, the present invention relates to compounds of general formula (I), supra, in which $R^8$ represents a $C_1$-$C_2$-alkyl group.

In another preferred embodiment, the present invention relates to compounds of general formula (I), supra, in which $R^8$ represents a methyl group.

The present invention covers compounds of general formula (I), supra, in which $R^9$, $R^{10}$, and $R^{11}$ are independently of each other selected from: hydrogen and $C_1$-$C_3$-alkyl.

In a preferred embodiment, the present invention relates to compounds of general formula (I), supra, in which $R^9$, $R^{10}$, and $R^{11}$ are independently of each other selected from: hydrogen and methyl.

In another preferred embodiment, the present invention relates to compounds of general formula (I), supra, in which $R^8$ represents a hydrogen atom, $R^9$ represents a hydrogen atom, $R^{10}$ represents a methyl group, and $R^{11}$ represents a methyl group.

In another preferred embodiment, the present invention relates to compounds of general formula (I), supra, in which $R^8$ represents a methyl group, $R^9$ represents a hydrogen atom, $R^{10}$ represents a methyl group, and $R^{11}$ represents a methyl group.

In another preferred embodiment, the present invention relates to compounds of general formula (I), supra, in which $R^8$ represents a methyl group, $R^9$ represents a methyl group, $R^{10}$ represents a methyl group, and $R^{11}$ represents a methyl group.

The present invention covers compounds of general formula (I), supra, in which $R^{13}$ represents a hydrogen atom or a group selected from: $C_1$-$C_6$-alkyl, $C_3$-$C_6$-cycloalkyl, HO—($C_2$-$C_6$-alkyl)-, and ($C_1$-$C_3$-alkoxy)-($C_1$-$C_6$-alkyl)-.

The present invention covers compounds of general formula (I), supra, in which $R^{13}$ represents a hydrogen atom or a group selected from: $C_1$-$C_6$-alkyl, $C_3$-$C_6$-cycloalkyl, HO—($C_2$-$C_6$-alkyl)-, and ($C_1$-$C_3$-alkoxy)-($C_2$-$C_6$-alkyl)-.

In a preferred embodiment, the present invention relates to compounds of general formula (I), supra, in which $R^{13}$ represents a hydrogen atom or a $C_1$-$C_3$-alkyl group.

In another preferred embodiment, the present invention relates to compounds of general formula (I), supra, in which $R^{13}$ represents a hydrogen atom or a methyl group.

The present invention covers compounds of general formula (I), supra, in which $R^{14}$ and $R^{15}$ are independently of each other selected from: hydrogen, $C_1$-$C_6$-alkyl, $C_3$-$C_6$-cycloalkyl, HO—($C_2$-$C_6$-alkyl)-, ($C_1$-$C_3$-alkoxy)-($C_2$-$C_6$-alkyl)-, $C_1$-$C_6$-haloalkyl, H$_2$N—($C_2$-$C_6$-alkyl)-, ($C_1$-$C_3$-alkyl)N(H)($C_2$-$C_6$-alkyl)-, ($C_1$-$C_3$-alkyl)$_2$N($C_2$-$C_6$-alkyl)-, $R^{13}$OC(=O)—($C_1$-$C_6$-alkyl)-, 4- to 6-membered heterocycloalkyl, phenyl, heteroaryl, phenyl-($C_1$-$C_6$-alkyl)-, and heteroaryl-($C_1$-$C_6$-alkyl)-; wherein phenyl and heteroaryl groups are optionally substituted with one or two substituents, which are independently of each other selected from: $C_1$-$C_3$-alkyl, $C_3$-$C_6$-cycloalkyl, $C_1$-$C_3$-alkoxy, $C_3$-$C_6$-cycloalkyloxy, $C_1$-$C_3$-haloalkyl, $C_1$-$C_3$-haloalkoxy, halogen, cyano, —C(=O)$OR^{13}$, and —C(=O)NH$_2$; or $R^{14}$ and $R^{15}$ together with the nitrogen atom to which they are attached form a 4-6-membered heterocycloalkyl; said 4-6-membered heterocycloalkyl being optionally substituted with one substituent selected from: $C_1$-$C_3$-alkyl, $C_1$-$C_3$-haloalkyl, $C_1$-$C_3$-alkoxy, $C_1$-$C_3$-haloalkoxy, $C_3$-$C_6$-cycloalkyl, $C_3$-$C_6$-cycloalkyloxy, amino, hydroxy, halogen, and cyano; or said 4-6-membered heterocycloalkyl being optionally substituted with one or two halogen atoms.

In a preferred embodiment, the present invention relates to compounds of general formula (I), supra, in which $R^{14}$ and $R^{15}$ are independently of each other selected from: hydrogen, $C_1$-$C_6$-alkyl, $C_3$-$C_6$-cycloalkyl, HO—($C_2$-$C_6$-alkyl)-, ($C_1$-$C_3$-alkoxy)-($C_2$-$C_6$-alkyl)-, $C_1$-$C_6$-haloalkyl, H$_2$N—($C_2$-$C_6$-alkyl)-, ($C_1$-$C_3$-alkyl)N(H)($C_2$-$C_6$-alkyl)-, ($C_1$-$C_3$-alkyl)$_2$N($C_2$-$C_6$-alkyl)-, $R^{13}$OC(=O)—($C_1$-$C_6$-alkyl)-, 4- to 6-membered heterocycloalkyl, phenyl, heteroaryl, phenyl-($C_1$-$C_6$-alkyl)-, and heteroaryl-($C_1$-$C_6$-alkyl)-; wherein phenyl and heteroaryl groups are optionally substituted with one or two substituents, which are independently of each other selected from: $C_1$-$C_3$-alkyl, $C_3$-$C_6$-cycloalkyl, $C_1$-$C_3$-alkoxy, $C_3$-$C_6$-cycloalkyloxy, $C_1$-$C_3$-haloalkyl, $C_1$-$C_3$-haloalkoxy, halogen, cyano, —C(=O)$OR^{13}$, and —C(=O)NH$_2$.

In another preferred embodiment, the present invention relates to compounds of general formula (I), supra, in which $R^{14}$ and $R^{15}$ are independently of each other selected from: hydrogen, $C_1$-$C_6$-alkyl, and $C_3$-$C_6$-cycloalkyl.

In another preferred embodiment, the present invention relates to compounds of general formula (I), supra, in which $R^{14}$ and $R^{15}$ are independently of each other selected from: hydrogen, and $C_1$-$C_3$-alkyl.

In another preferred embodiment, the present invention relates to compounds of general formula (I), supra, in which $R^{14}$ represents a hydrogen atom and $R^{15}$ represents a hydrogen atom.

In another preferred embodiment, the present invention relates to compounds of general formula (I), supra, in which $R^{14}$ and $R^{15}$ together with the nitrogen atom to which they are attached form a 4-6-membered heterocycloalkyl; said 4-6-membered heterocycloalkyl being optionally substituted with one substituent selected from: $C_1$-$C_3$-alkyl, $C_1$-$C_3$-haloalkyl, $C_1$-$C_3$-alkoxy, $C_1$-$C_3$-haloalkoxy, $C_3$-$C_6$-cycloalkyl, $C_3$-$C_6$-cycloalkyloxy, amino, hydroxy, halogen, and cyano; or said 4-6-membered heterocycloalkyl being optionally substituted with one or two halogen atoms.

In another preferred embodiment, the present invention relates to compounds of general formula (I), supra, in which $R^{14}$ and $R^{15}$ together with the nitrogen atom to which they are attached form a 4-6-membered heterocycloalkyl; said 4-6-membered heterocycloalkyl being optionally substituted with one substituent selected from: $C_1$-$C_3$-alkyl, $C_1$-$C_3$-haloalkyl; or said 4-6-membered heterocycloalkyl being optionally substituted with one or two halogen atoms.

The present invention covers compounds of general formula (I), supra, in which $R^{16}$ represents a hydrogen atom or a group selected from: $C_1$-$C_6$-alkyl, HO—($C_1$-$C_6$-alkyl)-, $C_3$-$C_6$-cycloalkyl, HO—($C_3$-$C_6$-cycloalkyl)-, $C_1$-$C_6$-haloalkyl, ($C_1$-$C_3$-alkoxy)-($C_1$-$C_6$-alkyl)-, phenyl, heteroaryl, and 4- to 6-membered heterocycloalkyl; wherein phenyl and heteroaryl groups are optionally substituted with one or two substituents, which are independently of each other selected from: $C_1$-$C_3$-alkyl, $C_3$-$C_6$-cycloalkyl, $C_1$-$C_3$-alkoxy, $C_3$-$C_6$-cycloalkyloxy, $C_1$-$C_3$-haloalkyl, $C_1$-$C_3$-haloalkoxy, halogen, cyano, —C(=O)O$R^{13}$, and —C(=O)N($R^{14}$)$R^{15}$.

In a preferred embodiment, the present invention relates to compounds of general formula (I), supra, in which $R^{16}$ represents a hydrogen atom or a group selected from: $C_1$-$C_3$-alkyl, HO—($C_1$-$C_3$-alkyl)-, $C_3$-$C_6$-cycloalkyl, HO—($C_3$-$C_6$-cycloalkyl)-, $C_1$-$C_3$-haloalkyl, ($C_1$-$C_3$-alkoxy)-($C_1$-$C_3$-alkyl)-, phenyl, heteroaryl, and 4- to 6-membered heterocycloalkyl; wherein phenyl and heteroaryl groups are optionally substituted with one or two substituents, which are independently of each other selected from: $C_1$-$C_3$-alkyl, $C_3$-$C_6$-cycloalkyl, $C_1$-$C_3$-alkoxy, $C_3$-$C_6$-cycloalkyloxy, $C_1$-$C_3$-haloalkyl, $C_1$-$C_3$-haloalkoxy, halogen, cyano, —C(=O)O$R^{13}$, and —C(=O)N($R^{14}$)$R^{15}$.

In another preferred embodiment, the present invention relates to compounds of general formula (I), supra, in which $R^{16}$ represents a hydrogen atom or a group selected from: $C_1$-$C_3$-alkyl, $C_3$-$C_6$-cycloalkyl, HO—($C_3$-$C_6$-cycloalkyl)-, $C_1$-$C_3$-haloalkyl, ($C_1$-$C_3$-alkoxy)-($C_1$-$C_3$-alkyl)-, phenyl, and 4- to 6-membered heterocycloalkyl; wherein the phenyl group is optionally substituted with one or two substituents, which are independently of each other selected from: $C_1$-$C_3$-alkyl, $C_3$-$C_6$-cycloalkyl, $C_1$-$C_3$-alkoxy, $C_3$-$C_6$-cycloalkyloxy, $C_1$-$C_3$-haloalkyl, $C_1$-$C_3$-haloalkoxy, halogen, cyano, —C(=O)O$R^{13}$, and —C(=O)N($R^{14}$)$R^{15}$.

In another preferred embodiment, the present invention relates to compounds of general formula (I), supra, in which $R^{16}$ represents a hydrogen atom or a group selected from: $C_1$-$C_3$-alkyl, $C_3$-$C_6$-cycloalkyl, HO—($C_3$-$C_6$-cycloalkyl)-, $C_1$-$C_3$-haloalkyl, ($C_1$-$C_3$-alkoxy)-($C_1$-$C_3$-alkyl)-, phenyl, and 4- to 6-membered heterocycloalkyl; wherein the phenyl group is optionally substituted with one or two halogen atoms.

In another preferred embodiment, the present invention relates to compounds of general formula (I), supra, in which $R^{16}$ represents a hydrogen atom or a group selected from: $C_1$-$C_3$-alkyl, $C_3$-$C_6$-cycloalkyl, ($C_1$-$C_3$-alkoxy)-($C_1$-$C_3$-alkyl)-, and phenyl.

In another preferred embodiment, the present invention relates to compounds of general formula (I), supra, in which $R^{16}$ represents a hydrogen atom.

In another preferred embodiment, the present invention relates to compounds of general formula (I), supra, in which $R^{16}$ represents a group selected from: $C_1$-$C_3$-alkyl, $C_3$-$C_6$-cycloalkyl, and ($C_1$-$C_3$-alkoxy)-($C_1$-$C_3$-alkyl)-.

The present invention covers compounds of general formula (I), supra, in which $R^{17}$ represents a group selected from: —N($R^{14}$)$R^{15}$ and $C_1$-$C_6$-alkoxy.

In a preferred embodiment, the present invention relates to compounds of general formula (I), supra, in which $R^{17}$ represents a —N($R^{14}$)$R^{15}$ group.

In another preferred embodiment, the present invention relates to compounds of general formula (I), supra, in which $R^{17}$ represents a $C_1$-$C_3$-alkoxy- group.

In another preferred embodiment, the present invention relates to compounds of general formula (Ia)

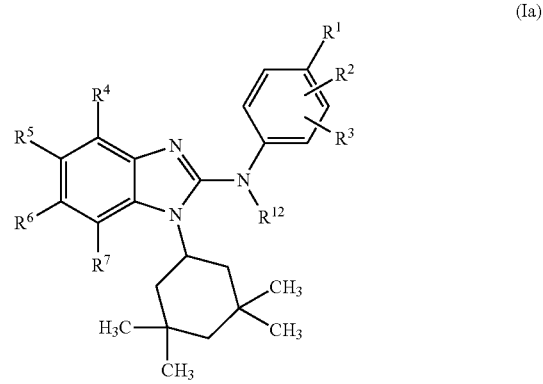

(Ia)

in which $R^1$, $R^2$, $R^3$, $R^4$, $R^5$, $R^6$, $R^7$ and $R^{12}$ are as defined for the compounds of general formula (I) in any of the above mentioned embodiments.

In another preferred embodiment, the present invention relates to compounds of general formula (Ib)

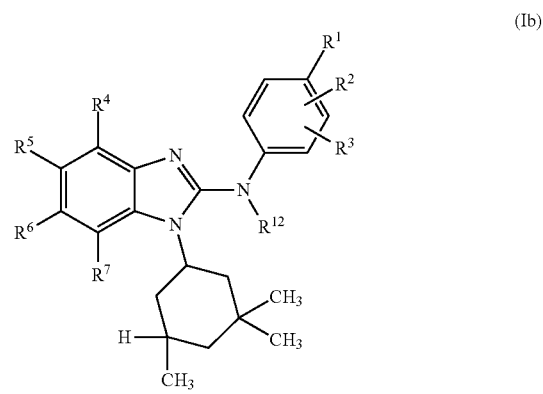

(Ib)

in which $R^1$, $R^2$, $R^3$, $R^4$, $R^5$, $R^6$, $R^7$ and $R^{12}$ are as defined for the compounds of general formula (I) in any of the above mentioned embodiments.

In another preferred embodiment, the present invention relates to compounds of general formula (Ic)

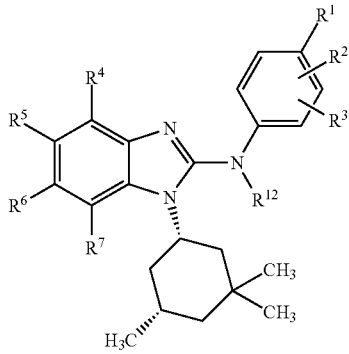

(Ic)

in which $R^1$, $R^2$, $R^3$, $R^4$, $R^5$, $R^6$, $R^7$ and $R^{12}$ are as defined for the compounds of general formula (I) in any of the above mentioned embodiments.

In another preferred embodiment, the present invention relates to compounds of general formula (Id)

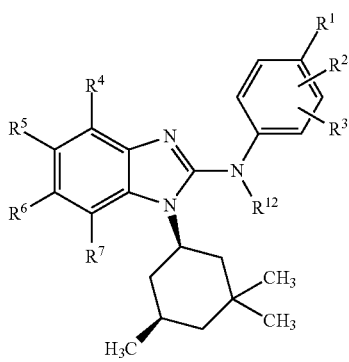

(Id)

in which $R^1$, $R^2$, $R^3$, $R^4$, $R^5$, $R^6$, $R^7$ and $R^{12}$ are as defined for the compounds of general formula (I) in any of the above mentioned embodiments.

It is to be understood that the present invention relates also to any combination of the preferred embodiments described above.

Some examples of combinations are given hereinafter. However, the invention is not limited to these combinations.

In a preferred embodiment, the present invention relates to compounds of general formula (I):

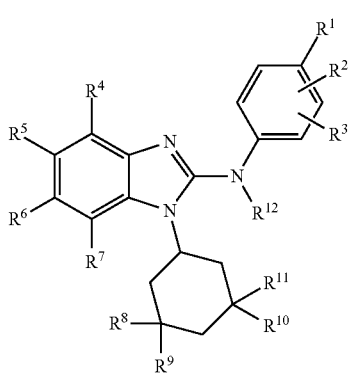

(I)

in which:

$R^1$ represents a halogen atom or group selected from:
$C_1$-$C_6$-alkyl, $C_1$-$C_6$-alkoxy, $C_1$-$C_6$-haloalkyl, $C_1$-$C_6$-haloalkoxy, cyano, ($C_1$-$C_6$-alkyl)-S—, and ($C_1$-$C_6$-haloalkyl)-S—;

$R^2$ represents a hydrogen atom;

$R^3$ represents a hydrogen atom;

$R^4$ represents a hydrogen atom;

$R^5$ represents a phenyl or heteroaryl group; wherein said group is optionally substituted, with one or more substituents, which are independently of each other selected from:
halo-, cyano, $C_1$-$C_6$-alkyl, $C_3$-$C_6$-cycloalkyl, $C_1$-$C_6$-haloalkyl, $C_1$-$C_6$-haloalkoxy, nitro, $R^{13}$O—, $R^{13}$S—, $R^{13}$OC(=O)—($C_1$-$C_6$-alkyl)-, $R^{13}$OC(=O)—($C_2$-$C_6$-alkenyl)-, $R^{13}$OC(=O)—($C_1$-$C_6$-alkoxy)-, $R^{14}(R^{15})$NC(=O)—($C_1$-$C_6$-alkyl)-, $R^{14}(R^{15})$NC(=O)—($C_2$-$C_6$-alkenyl)-, $R^{14}(R^{15})$NC(=O)—($C_1$-$C_6$-alkoxy)-, ($C_1$-$C_6$-alkyl)-S—, ($C_1$-$C_6$-alkyl)-S(=O)—, ($C_1$-$C_6$-alkyl)-S(=O)$_2$—, ($C_1$-$C_6$-haloalkyl)-S—, —C(=O)$OR^{13}$, —C(=O)N($R^{14}$)$R^{15}$, —C(=O)N($R^{14}$)S(=O)$_2R^{16}$, —N($R^{14}$)$R^{15}$, —N($R^{14}$)C(=O)$R^{16}$, —N($R^{14}$)C(=O)$R^{17}$, —N($R^{14}$)S(=O)$_2R^{16}$, —S(=O)$_2OR^{13}$, and —S(=O)$_2$N($R^{14}$)$R^{15}$;

wherein said heteroaryl group is selected from: thienyl, furanyl, pyrrolyl, oxazolyl, thiazolyl, imidazolyl, pyrazolyl, isoxazolyl, isothiazolyl, oxadiazolyl, triazolyl, tetrazolyl, thiadiazolyl, thia-4H-pyrazolyl, pyridinyl, pyridazinyl, pyrimidinyl, pyrazinyl, and triazinyl;

$R^6$ represents a hydrogen atom or a halogen atom or group selected from:
$C_1$-$C_6$-alkyl, and $C_1$-$C_6$-alkoxy;

$R^7$ represents a hydrogen atom;

$R^8$ represents a $C_1$-$C_3$-alkyl group;

$R^9$, $R^{10}$, and $R^{11}$
are independently of each other selected from: hydrogen and $C_1$-$C_3$-alkyl;

$R^{12}$ represents a hydrogen atom;

$R^{13}$ represents a hydrogen atom or a group selected from: $C_1$-$C_6$-alkyl, $C_3$-$C_6$-cycloalkyl, HO—($C_2$-$C_6$-alkyl)-, and ($C_1$-$C_3$-alkoxy)-($C_2$-$C_6$-alkyl)-;

$R^{14}$ and $R^{15}$
are independently of each other selected from: hydrogen, $C_1$-$C_6$-alkyl, and $C_3$-$C_6$-cycloalkyl;

or $R^{14}$ and $R^{15}$
together with the nitrogen atom to which they are attached form a 4-6-membered heterocycloalkyl; said 4-6-membered heterocycloalkyl being optionally substituted with one substituent selected from: $C_1$-$C_3$-alkyl, $C_1$-$C_3$-haloalkyl; or said 4-6-membered heterocycloalkyl being optionally substituted with one or two halogen atoms;

$R^{16}$ represents a hydrogen atom or a group selected from: $C_1$-$C_3$-alkyl, $C_3$-$C_6$-cycloalkyl, ($C_1$-$C_3$-alkoxy)-($C_1$-$C_3$-alkyl)-, and phenyl;

$R^{17}$ represents a group selected from: —N($R^{14}$)$R^{15}$ and $C_1$-$C_3$-alkoxy;

or a stereoisomer, a tautomer, an N-oxide, a hydrate, a solvate, or a salt thereof, or a mixture of same.

In another preferred embodiment, the present invention relates to compounds of general formula (I):

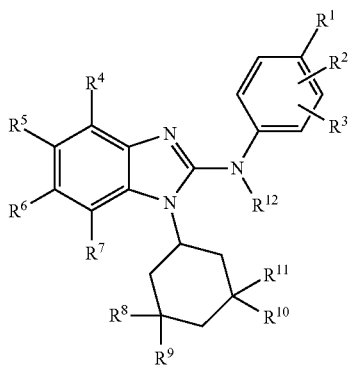

(I)

in which:
R¹ represents a halogen atom or group selected from:
  $C_1$-$C_6$-alkyl, $C_1$-$C_6$-alkoxy, $C_1$-$C_6$-haloalkyl, $C_1$-$C_6$-haloalkoxy, and ($C_1$-$C_6$-haloalkyl)-S—;
R² represents a hydrogen atom;
R³ represents a hydrogen atom;
R⁴ represents a hydrogen atom;
R⁵ represents a phenyl or heteroaryl group; wherein said group is optionally substituted, with one or more substituents, which are independently of each other selected from:
  halo-, cyano, $C_1$-$C_6$-alkyl, $C_1$-$C_6$-haloalkyl, $C_1$-$C_6$-haloalkoxy, $R^{13}$O—, $R^{13}$S—, ($C_1$-$C_6$-alkyl)-S—, ($C_1$-$C_6$-alkyl)-S(=O)—, ($C_1$-$C_6$-alkyl)-S(=O)$_2$—, ($C_1$-$C_6$-haloalkyl)-S—, —C(=O)O$R^{13}$, and —C(=O)N($R^{14}$)$R^{15}$;
  wherein said heteroaryl group is selected from: thienyl, furanyl, pyrrolyl, oxazolyl, thiazolyl, imidazolyl, pyrazolyl, isoxazolyl, isothiazolyl, oxadiazolyl, triazolyl, tetrazolyl, thiadiazolyl, thia-4H-pyrazolyl, pyridinyl, pyridazinyl, pyrimidinyl, pyrazinyl, and triazinyl;
R⁶ represents a hydrogen atom or a halogen atom or group selected from:
  $C_1$-$C_6$-alkyl, and $C_1$-$C_6$-alkoxy;
R⁷ represents a hydrogen atom;
R⁸ represents a $C_1$-$C_3$-alkyl group;
R⁹, R¹⁰, and R¹¹
  are independently of each other selected from: hydrogen and $C_1$-$C_3$-alkyl;
R¹² represents a hydrogen atom;
R¹³ represents a hydrogen atom or a $C_1$-$C_3$-alkyl group;
R¹⁴ and R¹⁵
  are independently of each other selected from: hydrogen, and $C_1$-$C_3$-alkyl;
or
R¹⁴ and R¹⁵
  together with the nitrogen atom to which they are attached form a 4-6-membered heterocycloalkyl; said 4-6-membered heterocycloalkyl being optionally substituted with one substituent selected from: $C_1$-$C_3$-alkyl, and $C_1$-$C_3$-haloalkyl;
or a stereoisomer, a tautomer, an N-oxide, a hydrate, a solvate, or a salt thereof, or a mixture of same.

In another preferred embodiment, the present invention relates to compounds of general formula (I):

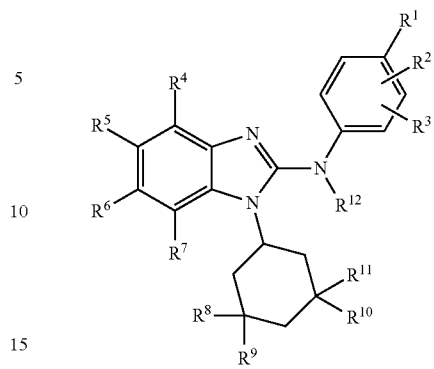

(I)

in which:
R¹ represents a halogen atom or group selected from:
  $C_1$-$C_6$-haloalkyl, $C_1$-$C_6$-haloalkoxy, and ($C_1$-$C_6$-haloalkyl)-S—;
R² represents a hydrogen atom;
R³ represents a hydrogen atom;
R⁴ represents a hydrogen atom;
R⁵ represents a phenyl or heteroaryl group; wherein said group is optionally substituted, with one or more substituents, which are independently of each other selected from:
  halo-, cyano, $C_1$-$C_6$-alkyl, $C_1$-$C_6$-haloalkyl, $C_1$-$C_6$-haloalkoxy, $R^{13}$O—, $R^{13}$S—, —C(=O)O$R^{13}$, and —C(=O)N($R^{14}$)$R^{15}$;
  wherein said heteroaryl group is selected from: oxazolyl, pyrazolyl, oxadiazolyl, triazolyl, tetrazolyl, and pyridinyl;
R⁶ represents a hydrogen atom or a halogen atom or group selected from:
  $C_1$-$C_6$-alkyl, and $C_1$-$C_6$-alkoxy;
R⁷ represents a hydrogen atom;
R⁸ represents a $C_1$-$C_3$-alkyl group;
R⁹, R¹⁰, and R¹¹
  are independently of each other selected from: hydrogen and $C_1$-$C_3$-alkyl;
R¹² represents a hydrogen atom;
R¹³ represents a hydrogen atom or a $C_1$-$C_3$-alkyl group;
R¹⁴ and R¹⁵
  are independently of each other selected from: hydrogen, and $C_1$-$C_3$-alkyl;
or a stereoisomer, a tautomer, an N-oxide, a hydrate, a solvate, or a salt thereof, or a mixture of same.

In another preferred embodiment, the present invention relates to compounds of general formula (I):

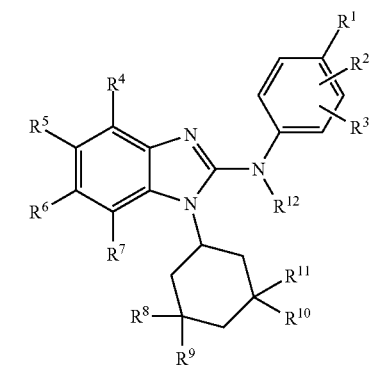

(I)

in which:
R¹ represents a halogen atom or group selected from:
    $C_1$-$C_6$-haloalkyl, $C_1$-$C_6$-haloalkoxy, and ($C_1$-$C_6$-haloalkyl)-S—;
R² represents a hydrogen atom;
R³ represents a hydrogen atom;
R⁴ represents a hydrogen atom;
R⁵ represents a phenyl or heteroaryl group; wherein said group is optionally substituted, with one or more substituents, which are independently of each other selected from:
    halo-, $C_1$-$C_6$-alkyl, $C_1$-$C_6$-haloalkyl, $R^{13}$O—, —C(=O)O$R^{13}$, and —C(=O)N($R^{14}$)$R^{15}$;
    wherein said heteroaryl group is selected from: oxazolyl, pyrazolyl, oxadiazolyl, triazolyl, tetrazolyl, and pyridinyl;
R⁶ represents a hydrogen atom or a $C_1$-$C_3$-group;
R⁷ represents a hydrogen atom;
R⁸ represents a $C_1$-$C_3$-alkyl group;
R⁹, R¹⁰, and R¹¹
    are independently of each other selected from: hydrogen and $C_1$-$C_3$-alkyl;
R¹² represents a hydrogen atom;
R¹³ represents a hydrogen atom or a $C_1$-$C_3$-alkyl group;
R¹⁴ and R¹⁵
    are independently of each other selected from: hydrogen, and $C_1$-$C_3$-alkyl;
or a stereoisomer, a tautomer, an N-oxide, a hydrate, a solvate, or a salt thereof, or a mixture of same.

In another preferred embodiment, the present invention relates to compounds of general formula (I):

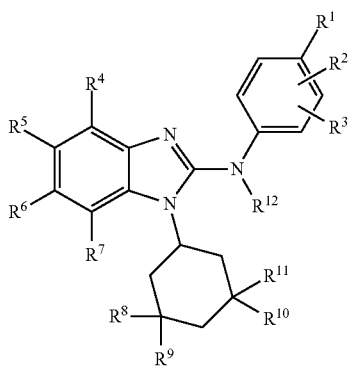

(I)

in which:
R¹ represents a $C_1$-$C_3$-haloalkoxy group;
R² represents a hydrogen atom;
R³ represents a hydrogen atom;
R⁴ represents a hydrogen atom;
R⁵ represents a phenyl or heteroaryl group;
    wherein said phenyl group is substituted with one substituent selected from: —C(=O)OH, —C(=O)OCH₃, —C(=O)NH₂;
    wherein said heteroaryl group is selected from: 3,5-dimethyl-1,2-oxazol-4-yl, 1H-pyrazol-4-yl, 3,5-dimethyl-1H-pyrazol-4-yl, 3-methyl-1H-pyrazol-4-yl, 1H-pyrazol-5-yl, 1,2-oxazol-4-yl, 1,3-dimethyl-1H-pyrazol-5-yl, 1-methyl-1H-pyrazol-4-yl, 2-methoxypyridin-4-yl, 1-methyl-3-(trifluoromethyl)-1H-pyrazol-4-yl, 5-methyl-1,3,4-oxadiazol-2-yl, 1H-tetrazol-5-yl, 5-methyl-4H-1,2,4-triazol-3-yl, 3-ethoxy-5-methyl-1,2-oxazol-4-yl;
R⁶ represents a hydrogen atom or a methyl group;
R⁷ represents a hydrogen atom;
R⁸ represents a $C_1$-$C_3$-alkyl group;
R⁹ represents a hydrogen atom or a $C_1$-$C_3$-alkyl group;
R¹⁰ represents a $C_1$-$C_3$-alkyl group;
R¹¹ represents a $C_1$-$C_3$-alkyl group;
R¹² represents a hydrogen atom;
or a stereoisomer, a tautomer, an N-oxide, a hydrate, a solvate, or a salt thereof, or a mixture of same.

In accordance with a first aspect, the present invention covers compounds of general formula (I):

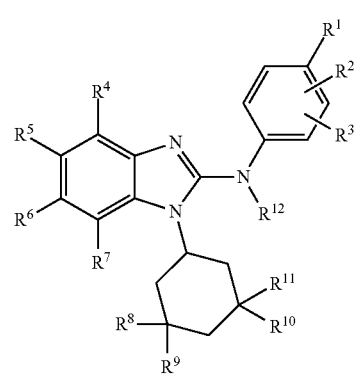

(I)

in which:
R¹ represents —O—CF₃;
R² represents a hydrogen atom;
R³ represents a hydrogen atom;
R⁴ represents a hydrogen atom;
R⁵ represents a phenyl or heteroaryl group;
    wherein said phenyl group is optionally substituted, with one substituent selected from: —C(=O)OH, —C(=O)OCH₃, —C(=O)NH₂, wherein said heteroaryl group is selected from: 3,5-dimethyl-1,2-oxazol-4-yl, 1H-pyrazol-4-yl, 3,5-dimethyl-1H-pyrazol-4-yl, 3-methyl-1H-pyrazol-4-yl, 1H-pyrazol-5-yl, 1,2-oxazol-4-yl, 1,3-dimethyl-1H-pyrazol-5-yl, 1-methyl-1H-pyrazol-4-yl, 2-methoxypyridin-4-yl, 1-methyl-3-(trifluoromethyl)-1H-pyrazol-4-yl, 5-methyl-1,3,4-oxadiazol-2-yl, 1H-tetrazol-5-yl, 5-methyl-4H-1,2,4-triazol-3-yl, 3-ethoxy-5-methyl-1,2-oxazol-4-yl;
R⁶ represents a hydrogen atom or a methyl group;
R⁷ represents a hydrogen atom;
R⁸ represents a methyl group;
R⁹ represents a hydrogen atom or a methyl group;
R¹⁰ represents a methyl group;
R¹¹ represents a methyl group;
R¹² represents a hydrogen atom;
or a stereoisomer, a tautomer, an N-oxide, a hydrate, a solvate, or a salt thereof, or a mixture of same.

It is to be understood that the present invention relates to any sub-combination within any embodiment or aspect of the present invention of compounds of general formula (I), supra.

More particularly still, the present invention covers compounds of general formula (I) which are disclosed in the Example section of this text, infra.

In accordance with another aspect, the present invention covers methods of preparing compounds of the present invention, said methods comprising the steps as described in the Experimental Section herein.

In accordance with an embodiment, the present invention also relates to a method of preparing a compound of general formula (I) as defined supra, said method comprising the step of allowing an intermediate compound of general formula (VI):

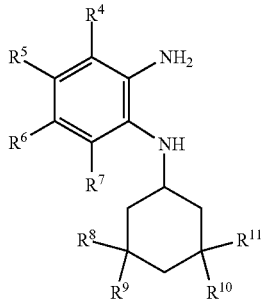
(VI)

in which $R^4$, $R^5$, $R^6$, $R^7$, $R^8$, $R^9$, $R^{10}$ and $R^{11}$ are as defined for the compound of general formula (I) supra, to react with a compound of general formula (III):

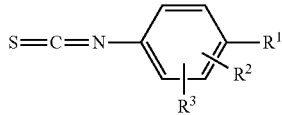
(III)

in which $R^1$, $R^2$ and $R^3$ are as defined as for the compound of general formula (I), supra, thereby giving a compound of general formula (I):

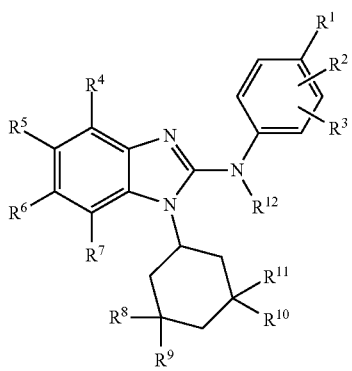
(I)

in which $R^1$, $R^2$, $R^3$, $R^4$, $R^5$, $R^6$, $R^7$, $R^8$, $R^9$, $R^{10}$, $R^{11}$ and $R^{12}$ are as defined for the compound of general formula (I) supra.

In accordance with another embodiment, the present invention also relates to a method of preparing a compound of general formula (I) as defined supra, said method comprising the step of allowing an intermediate compound of general formula (IV):

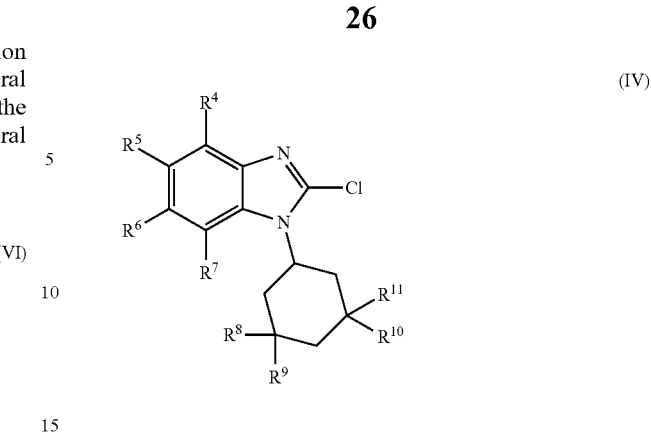
(IV)

in which $R^4$, $R^5$, $R^6$, $R^7$, $R^8$, $R^9$, $R^{10}$ and $R^{11}$ are as defined for the compound of general formula (I) supra, to react with a compound of general formula (V):

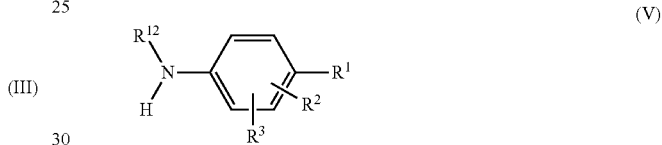
(V)

in which $R^1$, $R^2$, $R^3$ and $R^{12}$ are as defined as for the compound of general formula (I), supra, thereby giving a compound of general formula (I):

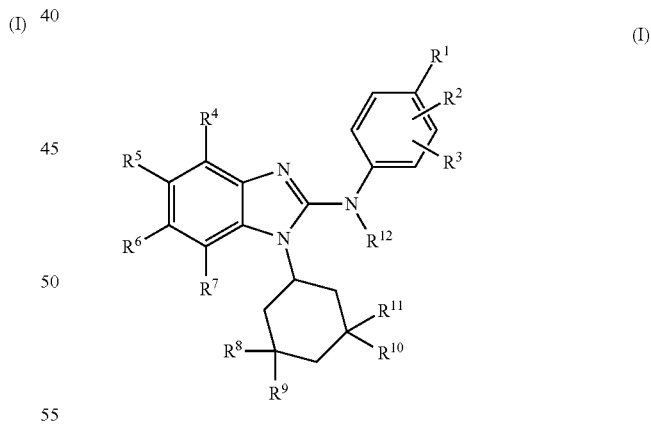
(I)

in which $R^1$, $R^2$, $R^3$, $R^4$, $R^5$, $R^6$, $R^7$, $R^8$, $R^9$, $R^{10}$, $R^{11}$ and $R^{12}$ are as defined for the compound of general formula (I) supra.

In accordance with another embodiment, the present invention also relates to a method of preparing a compound of general formula (I) as defined supra, said method comprising the step of allowing an intermediate compound of general formula (II):

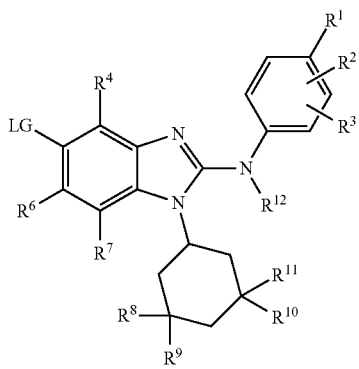
(II)

in which $R^4$, $R^6$, $R^7$, $R^8$, $R^9$, $R^{10}$, $R^{11}$ and $R^{12}$ are as defined for the compound of general formula (I) supra, and LG is a leaving group, preferably a halogen atom, more preferably a bromine atom, to react with a compound of general formula (VII):

$$R^5\text{—}Y \qquad (VII)$$

in which $R^5$ is as defined as for the compound of general formula (I), supra, and Y is a group enabling palladium catalysed coupling reactions, including a boronic acid group, an ester of a boronic acid group, a MIDA boronate, and a potassium fluoro borate;

thereby giving a compound of general formula (I):

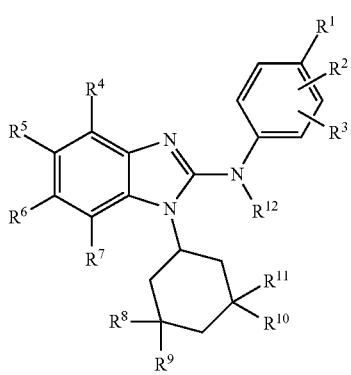
(I)

in which $R^1$, $R^2$, $R^3$, $R^4$, $R^5$, $R^6$, $R^7$, $R^8$, $R^9$, $R^{10}$, $R^{11}$ and $R^{12}$ are as defined for the compound of general formula (I) supra.

In a preferred embodiment, $R^5$—Y is selected from:

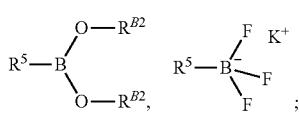

wherein $R^{B1}$ and $R^{B2}$ represent, independently from each other, a hydrogen atom or a $C_1$-$C_6$-alkyl- or $C_3$-$C_6$-cycloalkyl- group;

or $R^{B1}$ and $R^{B2}$ together represent a $C_2$-$C_6$-alkylene group.

In another preferred embodiment, $R^5$—Y represents an N-methyliminodiacetic acid (MIDA) boronate:

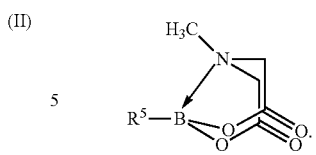

In another preferred embodiment, $R^5$—Y represents

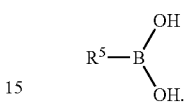

In accordance with a further aspect, the present invention covers intermediate compounds which are useful for the preparation of the compounds of general formula (I), supra.

Particularly, the inventions covers intermediate compounds of general formula (II):

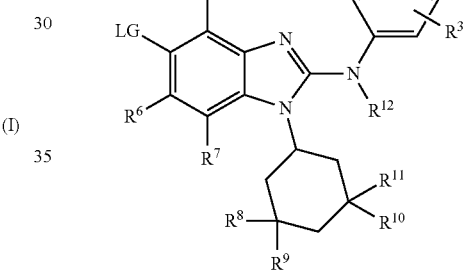
(II)

in which $R^4$, $R^6$, $R^7$, $R^8$, $R^9$, $R^{10}$, $R^{11}$ and $R^{12}$ are as defined for the compound of general formula (I) supra, and LG is a leaving group, preferably a halogen atom, more preferably a bromine atom, intermediate compounds of general formula (VI):

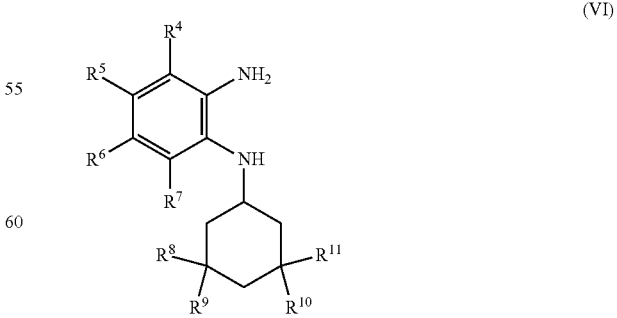
(VI)

in which $R^4$, $R^5$, $R^6$, $R^7$, $R^8$, $R^9$, $R^{10}$ and $R^{11}$ are as defined for the compound of general formula (I) supra, and
intermediate compounds of general formula (IV):

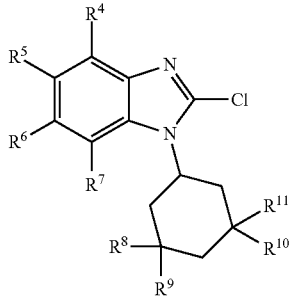

in which $R^4$, $R^5$, $R^6$, $R^7$, $R^8$, $R^9$, $R^{10}$ and $R^{11}$ are as defined for the compound of general formula (I) supra.

More particularly still, the present invention covers the intermediate compounds which are disclosed in the Example section of this text, infra.

In accordance with a further aspect, the present invention covers the use of the intermediate compounds of general formula (VI):

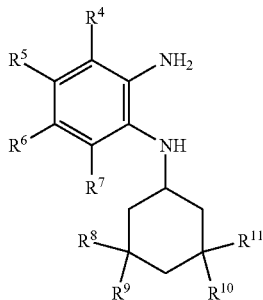

in which $R^4$, $R^5$, $R^6$, $R^7$, $R^8$, $R^9$, $R^{10}$ and $R^{11}$ are as defined for the compound of general formula (I) supra, for the preparation of a compound of general formula (I) as defined supra.

In accordance with yet another aspect, the present invention covers the use of the intermediate compounds of general formula (IV):

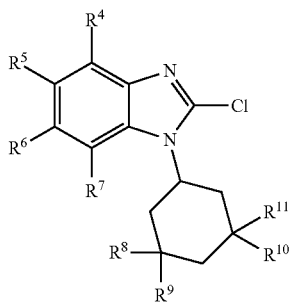

in which $R^4$, $R^5$, $R^6$, $R^7$, $R^8$, $R^9$, $R^{10}$ and $R^{11}$ are as defined for the compound of general formula (I) supra, for the preparation of a compound of general formula (I) as defined supra.

In accordance with yet another aspect, the present invention covers the use of the intermediate compounds of general formula (II):

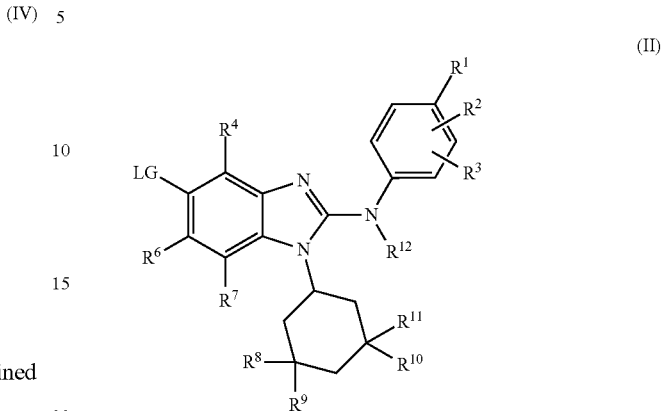

in which $R^4$, $R^6$, $R^7$, $R^8$, $R^9$, $R^{10}$, $R^{11}$ and $R^{12}$ are as defined for the compound of general formula (I) supra, and LG is a leaving group, preferably a halogen atom, more preferably a bromine atom,
for the preparation of a compound of general formula (I) as defined supra.

In accordance with a further aspect, the present invention relates to compounds of general formula (I), as decribed supra, or a stereoisomer, a tautomer, an N-oxide, a hydrate, a solvate, or a salt thereof, particularly a pharmaceutically acceptable salt thereof, or a mixture of same, for use in the treatment or prophylaxis of a disease.

In accordance with a further aspect, the present invention relates to a pharmaceutical composition comprising a compound of general formula (I), as decribed supra, or a stereoisomer, a tautomer, an N-oxide, a hydrate, a solvate, or a salt thereof, particularly a pharmaceutically acceptable salt thereof, or a mixture of same, and a pharmaceutically acceptable diluent or carrier.

Particularly, the pharmaceutical combination comprises:
one or more first active ingredients selected from a compound of general formula (I) as decribed supra, and
one or more second active ingredients selected from chemotherapeutic anti-cancer agents (see below).

In accordance with a further aspect, the present invention relates to use of a compound of general formula (I), as described supra, or a stereoisomer, a tautomer, an N-oxide, a hydrate, a solvate, or a salt thereof, particularly a pharmaceutically acceptable salt thereof, or a mixture of same, for the prophylaxis or treatment of a disease.

In accordance with a further aspect, the present invention relates to use of a compound of general formula (I), as described supra, or a stereoisomer, a tautomer, an N-oxide, a hydrate, a solvate, or a salt thereof, particularly a pharmaceutically acceptable salt thereof, or a mixture of same, for the preparation of a medicament for the prophylaxis or treatment of a disease.

The disease as mentioned before is in particular a disease of uncontrolled cell growth, proliferation and/or survival, an inappropriate cellular immune response, or an inappropriate cellular inflammatory response, particularly in which the disease of uncontrolled cell growth, proliferation and/or survival, inappropriate cellular immune response, or inappropriate cellular inflammatory response is a haematological tumour, a solid tumour and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

Experimental Section

The following table lists the abbreviations used in this paragraph and in the Intermediate Examples and Examples section as far as they are not explained within the text body. NMR peak forms are stated as they appear in the spectra, possible higher order effects have not been considered. Chemical names were generated using the ICS naming tool of ACD labs. In some cases generally accepted names of commercially available reagents were used in place of ICS naming tool generated names.

| Abbreviation | Meaning |
|---|---|
| ACN | acetonitrile |
| br. | broad signal in NMR |
| br. s. | broad singlet |
| CDI | di-1H-imidazol-1-ylmethanone |
| $CD_3OD$ | deuterated methanol |
| DMF | N,N-dimethylformamide |
| d | doublet |
| dd | doublet of doublets |
| ddd | doublet of doublet of doublets |
| DMSO | dimethyl sulfoxide |
| dquint | doublet of quintets |
| EDC | N-(3-dimethylaminopropyl)-N'-ethylcarbodiimide hydrochloride |
| ESI | electrospray ionization |
| EtOH | ethanol |
| h | hour(s) |
| HATU | N-[(dimethylamino)-1H-1,2,3-triazolo-[4,5-b]pyridin-1-ylmethylene]-N-methylmethanaminium hexafluorophosphate N-oxide |
| HCl | hydrochloric acid |
| HCOOH | formic acid |
| HOBt | hydroxybenzotriazole |
| HPLC, LC | high performance liquid chromatography |
| LiOH | lithium hydroxide |
| m | multiplet |
| $m_c$ | centered multiplet |
| min | minute(s) |
| MS | mass spectroscopy |
| MeOH | methanol |
| NaOH | sodium hydroxide |
| $Na_2CO_3$ | sodium carbonate |
| $Na_2SO_4$ | sodium sulfate |
| $NEt_3$ | triethylamine |
| $NH_4Cl$ | ammonium chloride |
| NMP | N-methyl-2-pyrrolidone |
| NMR | nuclear magnetic resonance |
| $Pd_2(dba)_3$ | tris(dibenzylideneacetone)dipalladium |
| PyBOP | (benzotriazol-1-yloxy)tripyrrolidinophosphonium hexafluorophosphate |
| quint | quintet |
| qt | quartet of triplets |
| $R_t$ | retention time |
| rt | room temperature |
| s | singlet |
| t | triplet |
| tt | triplet of triplets |
| T3P | propylphosphonic anhydride, 2,4,6-tripropyl-1,3,5,2,4,6-trioxatriphosphorinane-2,4,6-trioxide solution, PPACA, T3P ®. |
| THF | tetrahydrofurane |
| UPLC | ultra performance liquid chromatography |
| Xanthphos | 4,5-bis(diphenylphosphino)-9,9-dimethylxanthene |

Other abbreviations have their meanings customary per se to the skilled person. The various aspects of the invention described in this application are illustrated by the following examples which are not meant to limit the invention in any way.

Syntheses of Compounds (Overview)

The following schemes and general procedures illustrate general synthetic routes to the compounds of general formula (I) of the invention and are not intended to be limiting. It is obvious to the person skilled in the art that the order of transformations as exemplified in Schemes 1 to 3 can be modified in various ways. The order of transformations exemplified in Schemes 1 to 3 is therefore not intended to be limiting. In addition, interconversion of substituents, for example of residues $R^1$, $R^2$, $R^3$, $R^4$, $R^5$, $R^6$ and $R^7$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts, *Protective Groups in Organic Synthesis,* 3rd edition, Wiley 1999).

Scheme 1:

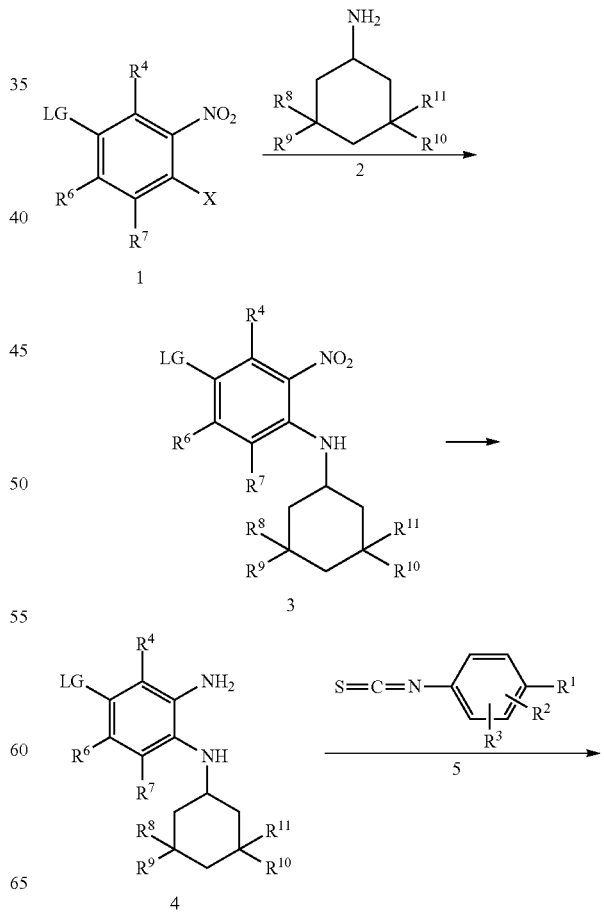

-continued

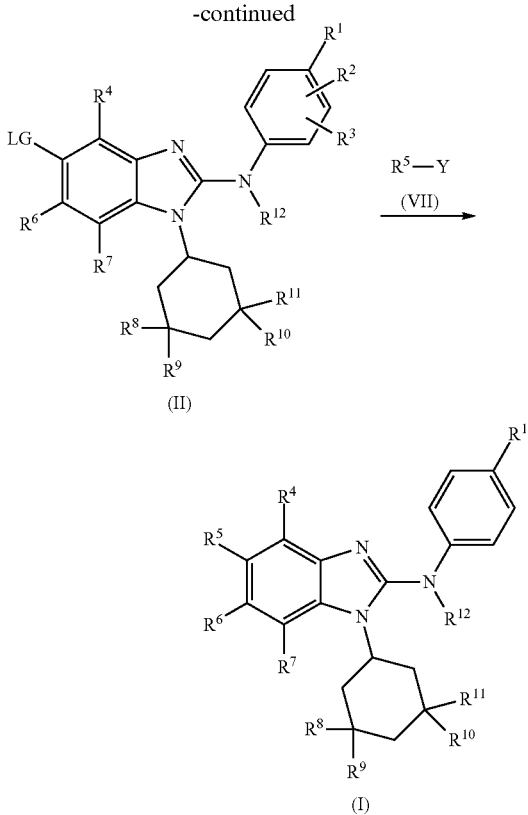

in which $R^1$, $R^2$, $R^3$, $R^4$, $R^5$, $R^6$, $R^7$, $R^8$, $R^9$, $R^{10}$, $R^{11}$ and $R^{12}$ are as defined supra, LG represents a leaving group such as a halogen atom, X represents a halogen atom, and Y represents boronic acid or a boronic ester or a trifluoroborate such as potassium fluoro borate.

Suitably functionalized compounds of formula (II) may be reacted with boronic acids or the corresponding pinacol esters or the corresponding trifluoroborates of general formula (VII) in a suitable solvent such as for example dioxane and the help of Pd catalysts such as for example ferrocen at temperatures between 0° C. and 70° C. Boronic acids or the corresponding pinacol esters or the corresponding trifluoroborates (VII) are either commercially available, known compounds or may be formed from known compounds by known methods by a person skilled in the art.

Suitably functionalized diamines of formula 4 may be reacted with thioisocyanates of general formula 5 in a suitable solvent such as for example tetrahydrofurane and in the presence of a carbodiimide such as for example diisopropylcarbodiimide or EDC at temperatures between 0° C. and the boiling point of the solvent, typically at 70° C. Thioisocyanates 5 are either commercially available, known compounds or may be formed from known compounds by known methods by a person skilled in the art.

Diamines of general formula 4 in turn may be obtained from nitroanilines of general formula 3 by reduction. For reduction, all processes that are known to the person skilled in the art may be applied. Nitroanilines 3 may be hydrogenated under an atmosphere of hydrogen at pressures between 1 bar and 100 bar in a suitable solvent such as for example ethyl acetate, tetrahydrofurane, methanol or ethanol and in the presence of a metal catalyst such as for example palladium on charcoal at temperatures between 0° C. and the boiling point of the solvent, typically at room temperature.

The addition of a suitable acid such as for example hydrochloric acid or acetic acid may be necessary. Alternatively, nitroanilines of general formula 3 may be reduced with iron/NH$_4$Cl or tin(II) chloride in a suitable solvent such as for example water, methanol or ethanol or mixtures thereof at temperatures between room temperature and the boiling point of the solvent, typically at 70° C. Nitroanilines of general formula 3 can be obtained from nitroarenes of general formula 1 by nucleophilic substitution with amines of general formula 2 in a suitable solvent such as for example tetrahydrofurane and in the presence of a suitable base such as for example potassium carbonate or triethylamine at temperatures between room temperature and the boiling point of the solvent, typically at 50-70° C. Instead of using amines of general formula 2 their corresponding ammonium salts can be used as well. Nitroarenes 1 and amines 2 or their corresponding ammonium salts are either commercially available, known compounds or may be formed from known compounds by known methods by a person skilled in the art.

Scheme 2:

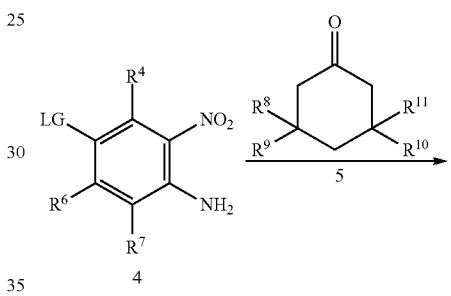

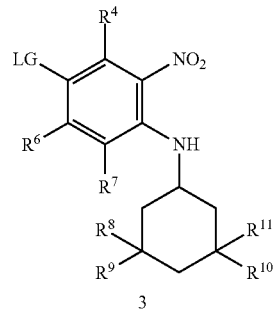

in which $R^4$, $R^6$, $R^7$, $R^8$, $R^9$, $R^{10}$, $R^{11}$ and LG are as defined supra.

An alternative route to nitroanilines of general formula 3 via reductive amination is outlined in Scheme 2. Nitroanilines 4 may be reacted with cyclohexanones 5 in a suitable solvent such as for example dichloromethane or dichloroethane and in the presence of a reducing agent such as for example sodium borohydride or sodium triacetoxyborohydride at temperatures between 0° C. and the boiling point of the solvent, typically at room temperature. It might be necessary to add an acid such as for example trifluoroacetic acid to the reaction mixture. Nitroanilines 4 and cyclohexanones 5 are either commercially available, known compounds or may be formed from known compounds by known methods by a person skilled in the art.

Scheme 3:

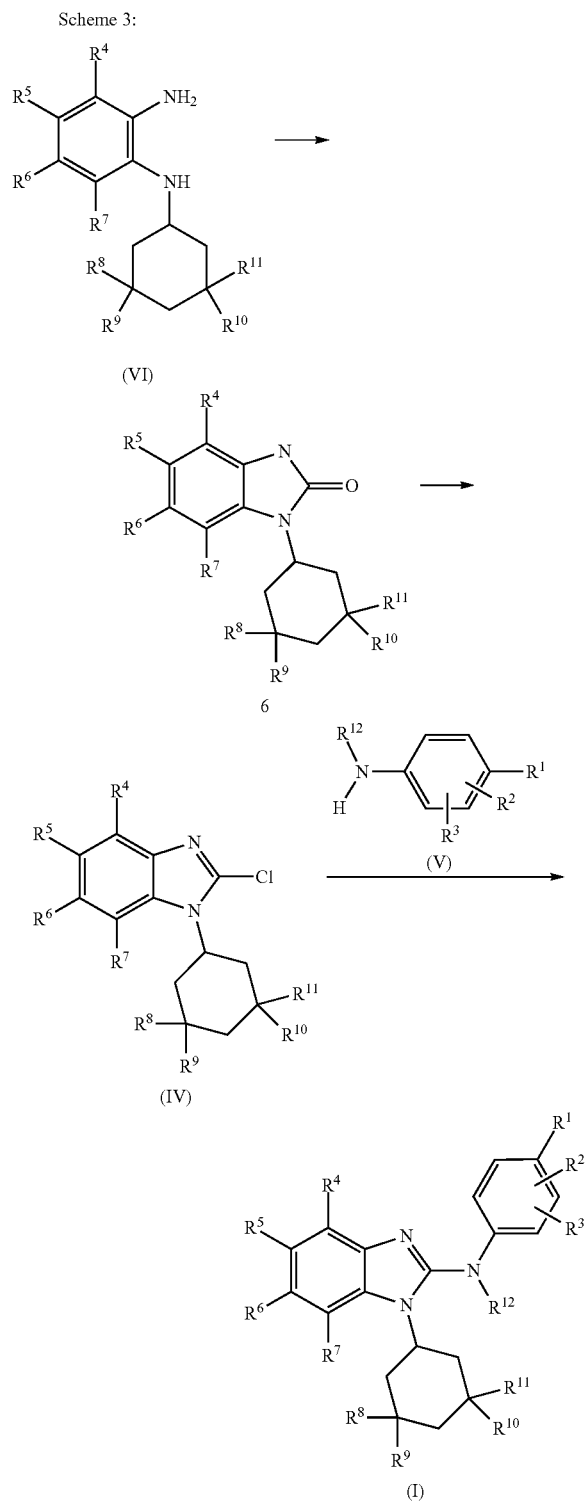

in which $R^1$, $R^2$, $R^3$, $R^4$, $R^5$, $R^6$, $R^7$, $R^8$, $R^9$, $R^{10}$, $R^{11}$ and $R^{12}$ are as defined supra.

Suitably functionalized chlorobenzimidazoles (IV) may be reacted with anilines of general formula (V) in a suitable solvent such as for example NMP at temperatures between room temperature and the boiling point of the solvent, typically at 110° C. Anilines (V) are either commercially available, known compounds or may be formed from known compounds by known methods by a person skilled in the art. Chlorobenzimidazoles (IV) in turn can be obtained from benzimidazolones of general formula 6 by reaction in chlorinating agents such as for example phosphoric trichloride at temperatures between room temperature and the boiling point of the reagent, typically at 105° C. Benzimidazolones of general formula 6 may be synthesized from suitably functionalized diamines of general formula (VI) by reaction with carbonic acid equivalents such as for example CDI, phosgene or phosgene derivatives in a suitable solvent such as for example DMF or tetrahydrofurane at temperatures between room temperature and the boiling point of the solvent, typically at 50° C.

General Part

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP-NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the persion skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

UPLC-MS Standard Procedures

Analytical UPLC-MS was performed as described below. The masses (m/z) are reported from the positive mode electrospray ionisation unless the negative mode is indicated (ES−).

In most of the cases method A is used. If not, it is indicated.

UPLC-MS Method A

Instrument: Waters Acquity UPLC-MS SQD 3001; Column: Acquity UPLC BEH C18 1.7 50×2.1 mm; Eluent A: water+0.1% formic acid, Eluent B: acetonitrile; Gradient:

0-1.6 min 1-99% B, 1.6-2.0 min 99% B; Flow rate 0.8 mL/min; Temperature: 60° C.; Injection: 2 μL; DAD scan: 210-400 nm.

UPLC-MS Method B

Instrument: Waters Acquity UPLC-MS SQD 3001; Column: Acquity UPLC BEH C18 1.7 50×2.1 mm; Eluent A: water+0.2% ammonia, Eluent B: acetonitrile; Gradient: 0-1.6 min 1-99% B, 1.6-2.0 min 99% B; Flow rate 0.8 mL/min; Temperature: 60° C.; Injection: 2 μL; DAD scan: 210-400 nm; ELSD.

UPLC-MS Method C

Instrument: Waters Acquity UPLC-MS ZQ4000; Column: Acquity UPLC BEH C18 1.7 50×2.1 mm; Eluent A: water+0.05% formic acid, Eluent B: acetonitrile+0.05% formic acid; Gradient: 0-1.6 min 1-99% B, 1.6-2.0 min 99% B; Flow rate 0.8 mL/min; Temperature: 60° C.; Injection: 2 μL; DAD scan: 210-400 nm.

UPLC-MS Method D

Instrument: Waters Acquity UPLC-MS ZQ4000; Column: Acquity UPLC BEH C18 1.7 50×2.1 mm; Eluent A: water+0.2% ammonia, Eluent B: acetonitrile; Gradient: 0-1.6 min 1-99% B, 1.6-2.0 min 99% B; Flow rate 0.8 mL/min; Temperature: 60° C.; Injection: 2 μL; DAD scan: 210-400 nm; ELSD.

UPLC-MS Method E

Instrument: Waters Acquity UPLC-MS; Column: XBridge BEH C18 2.5 μm 2.1×50 mm; Eluent A: 10 mM ammonium bicarbonate pH 10, Eluent B: acetonitrile; Gradient: 50-98% B in 0.80 min, hold at 98% B to 1.30 min; Flow rate 0.8 mL/min; Detection: Waters Acquity Autosampler (UPLC LG 500 nm).

UPLC-MS Method F

Instrument: Waters Acquity UPLC-MS; Column: XBridge BEH C18 2.5 μm 2.1×50 mm; Eluent A: 10 mM ammonium bicarbonate pH 10, Eluent B: acetonitrile; Gradient: 2-98% B in 0.80 min, hold at 98% B to 1.30 min; Flow rate 0.8 mL/min; Detection: Waters Acquity Autosampler (UPLC LG 500 nm).

UPLC-MS Method G

Instrument: Waters Acquity UPLC-MS; Column: XBridge BEH C18 2.5 μm 2.1×50 mm; Eluent A: 10 mM ammonium bicarbonate pH 10, Eluent B: acetonitrile; Gradient: 60-98% B in 0.80 min, hold at 98% B to 1.30 min; Flow rate 0.8 mL/min; Detection: Waters Acquity Autosampler (UPLC LG 500 nm).

UPLC-MS Method H

Instrument: Waters Acquity UPLC-MS; Column: XBridge BEH C18 2.5 μm 2.1×50 mm; Eluent A: 10 mM ammonium bicarbonate pH 10, Eluent B: acetonitrile; Gradient: 2-98% B in 4.00 min, hold at 98% B to 4.70 min; Flow rate 0.8 mL/min; Detection: Waters Acquity Autosampler (UPLC LG 500 nm).

LC-MS Standard Procedures

Analytical LC-MS was performed as described below. The masses (m/z) are reported from the positive mode electrospray ionisation unless the negative mode is indicated (ES−).

LC-MS Method A

Instrument: Water Alliance 2695 HPLC Pump; Column: XBridge C18 2.5 μm 2.1×20 mm; Eluent A: 10 mM ammonium bicarbonate pH 10, Eluent B: acetonitrile; Gradient: hold at 50% B to 0.18 min, 50-95% B to 2.00 min, hold at 95% B to 2.60 min; Flow rate 1 mL/min; Detection: Waters 996 PDA 215-350 nm; Run Time: 3.10 min.

LC-MS Method B

Instrument: Water Alliance 2695 HPLC Pump; Column: XBridge C18 2.5 μm 2.1×20 mm; Eluent A: 10 mM ammonium bicarbonate pH 10, Eluent B: acetonitrile; Gradient: 0% B to 0.18 min, 0-95% B to 2.00 min, hold at 95% B to 2.60 min; Flow rate 1 mL/min; Detection: Waters 996 PDA 215-350 nm; Run Time: 3.10 min.

LC-MS Method C

Instrument: Water Alliance 2695 HPLC Pump; Column: XBridge C18 2.5 μm 2.1×20 mm; Eluent A: 10 mM ammonium bicarbonate pH 10, Eluent B: acetonitrile; Gradient: 20-70% B in 2.00 min, 70-95% B to 2.10, hold at 95% B to 2.60 min; Flow rate 1 mL/min; Detection: Waters 996 PDA 215-350 nm; Run Time: 3.10 min.

NMR peak forms are stated as they appear in the spectra, possible higher order effects have not been considered.

The obtained benzimidazoles of general formula (I) may be chiral and may be separated into their diastereomers and/or enantiomers by chiral HPLC.

Intermediates

Intermediate 1-1

(±) 5-bromo-N-[4-(trifluoromethoxy)phenyl]-1-[(cis)-3,3,5-trimethylcyclohexyl]-1H-benzimidazol-2-amine

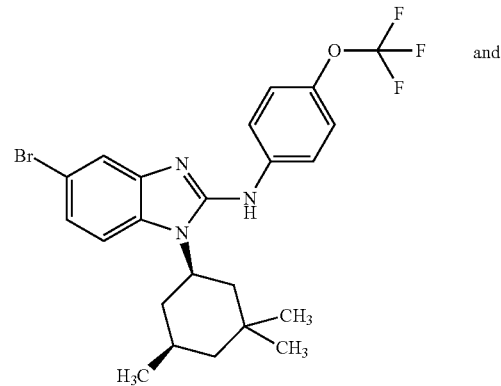

and

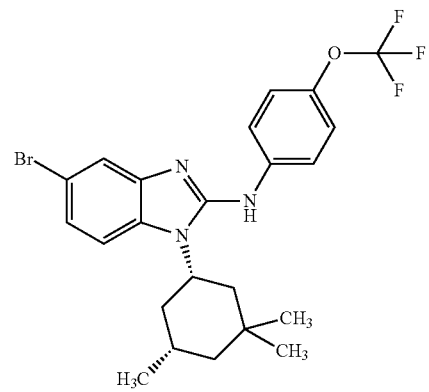

Step 1: (±) 4-bromo-2-nitro-N-(3,3,5-trimethylcyclohexyl)aniline 17 g (77.27 mmol) 4-Bromo-1-fluoro-2-nitrobenzene (commercially available, CAS-RN: 364-73-8)) were given in 308 mL tetrahydrofurane. After addition of 11.75 g (84.99 mmol) potassium carbonate the reaction mixture was stirred for 10 min at room temperature. 10.92 g (77.27 mmol) 3,3,5-trimethylcyclohexanamine (mixture of stereoisomers, commercially available, CAS-RN: 15901-42-5) were added and the reaction mixture was heated at 50° C. over night. The reaction mixture was diluted with ethyl acetate and water. The aqueous phase was reextracted twice with ethyl acetate and the combined organic extracts were dried (sodium sulfate). The solvent was evaporated yielding 28.3 g (97%) of the desired product as a mixture of stereoisomers. UPLC-MS: $R_t$=1.78 min; m/z=341 (ES+, M+1).

$^1$H-NMR (400 MHz, DMSO-$d_6$): δ [ppm]=0.72-1.03 (m, 11H), 1.13 (t, 1H), 1.29-1.39 (m, 1H), 1.59-1.89 (m, 2H), 1.91-2.05 (m, 1H), 3.70-3.90 (m, 1H), 7.12 (d, 1H), 7.64 (dd, 1H), 7.82 (d, 1H), 8.15 (d, 1H).

Step 2: (±) 4-bromo-$N^1$-[(cis)-3,3,5-trimethylcyclohexyl]benzene-1,2-diamine 28.3 g (82.93 mmol) (±) 4-Bromo-2-nitro-N-(3,3,5-trimethylcyclohexyl)aniline, described in step 1, were dissolved in methanol (366 mL). After addition of 66.83 g (290 mmol) tin(II)chloride dihydrate the reaction mixture was stirred for 12 hours at 70° C. The reaction mixture was evaporated to dryness and the residue was diluted with ethyl acetate. After washing with water and brine the organic phase was dried and the solvent was removed. Purification of the residue by column chromatography (eluents: hexane/ethyl acetate) yielded 27 g (99%) of a single stereoisomer (cis diastereoisomer as racemate).

UPLC-MS: $R_t$=1.54 min; m/z=311 (ES+, M+1).

$^1$H-NMR (300 MHz, DMSO-$d_6$): δ [ppm]=0.72-1.02 (m, 11H), 1.09-1.21 (m, 1H), 1.29-1.39 (m, 1H), 1.54-1.75 (m, 2H), 1.85-2.02 (m, 1H), 3.40-3.60 (m, 1H), 6.74-6.92 (m, 2H), 6.99 (d, 1H).

Step 3: (±) 5-bromo-N-[4-(trifluoromethoxy)phenyl]-1-[(cis)-3,3,5-trimethylcyclohexyl]-1H-benzimidazol-2-amine 5.00 g (16.06 mmol) (±) 4-Bromo-$N^1$-[(cis)-3,3,5-trimethylcyclohexyl]benzene-1,2-diamine, intermediate 1-1, step 2, were dissolved in 320 mL tetrahydrofurane. After addition of 3.52 g (16.06 mmol) 4-(trifluoromethoxy)-phenylisothiocyanate (commercially available, CAS-RN: 64285-95-6) and 4.05 g (32.13 mmol) N,N'-diisopropylcarbodiimide the reaction mixture was stirred at 70° C. for two hours. The reaction mixture was evaporated to dryness and the residue was diluted with dichloromethane. After washing with brine and water the organic phase was dried ($Na_2SO_4$) and filtered. The solvent was removed and the residue purified by column chromatography to yield 1.41 g (16.8%) of the title compound.

UPLC-MS: $R_t$=1.69 min; m/z=496.1 (ES+, M+1).

$^1$H-NMR (300 MHz, DMSO-$d_6$): δ [ppm]=0.91-1.21 (m, 10H), 1.32-1.50 (m, 2H), 1.65-2.09 (m, 4H), 4.58-4.73 (m, 1H), 7.08-7.18 (m, 1H), 7.27-7.38 (m, 2H), 7.46-7.58 (m, 2H), 7.75-7.86 (m, 2H), 9.12 (s, 1H).

Intermediate 1-2

(±) 5-bromo-N-{4-[(trifluoromethyl)sulfanyl]phenyl}-1-[(cis)-3,3,5-trimethylcyclo-hexyl]-1H-benzimidazol-2-amine

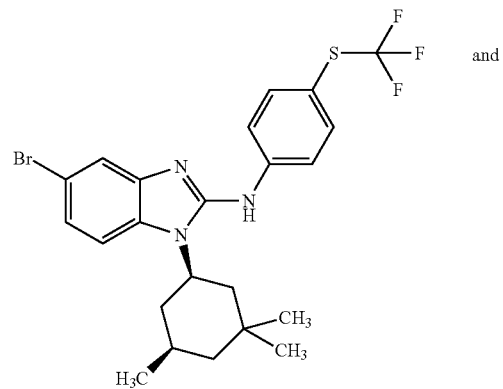

and

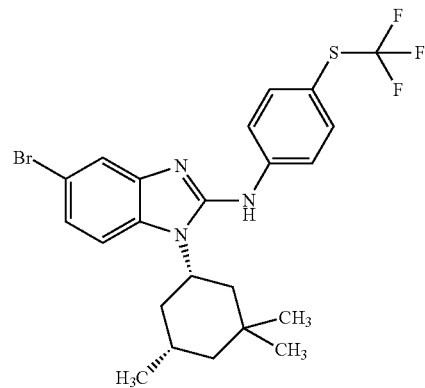

1.5 g (4.82 mmol) (±) 4-Bromo-$N^1$-[(cis)-3,3,5-trimethylcyclohexyl]benzene-1,2-diamine, intermediate 1-1, step 2, were dissolved in 96 mL tetrahydrofurane. After addition of 1.13 g (4.82 mmol) 1-isothiocyanato-4-[(trifluoromethyl)sulfanyl]benzene (commercially available, CAS-RN: 189281-95-6) and 1.22 g (9.64 mmol) N,N'-diisopropylcarbodiimide the reaction mixture was stirred at 70° C. for two hours. The reaction mixture was evaporated to dryness and the residue was diluted with dichloromethane. After washing with brine and water the organic phase was dried ($Na_2SO_4$) and filtered. The solvent was removed and the residue purified by column chromatography yielding 1.06 g (40.8%) of the title compound.

UPLC-MS: $R_t$=1.81 min; m/z=512.10 (ES+, M+1).

$^1$H-NMR (400 MHz, DMSO-$d_6$): δ [ppm]=0.90-1.18 (m, 10H), 1.32-1.48 (m, 2H), 1.68-1.80 (m, 1H), 1.80-1.93 (m, 2H), 2.01 (t, 1H), 4.68 (t, 1H), 7.12-7.20 (m, 1H), 7.52-7.62 (m, 2H), 7.65 (d, 2H), 7.83 (d, 2H), 9.35 (s, 1H).

Intermediate 1-3

(±) 5-bromo-N-{4-[(trifluoromethyl)]phenyl}-1-[(cis)-3,3,5-trimethylcyclohexyl]-1H-benzimidazol-2-amine

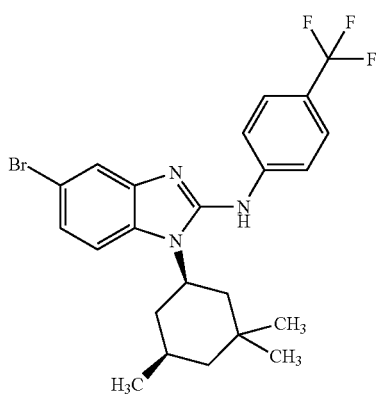

and

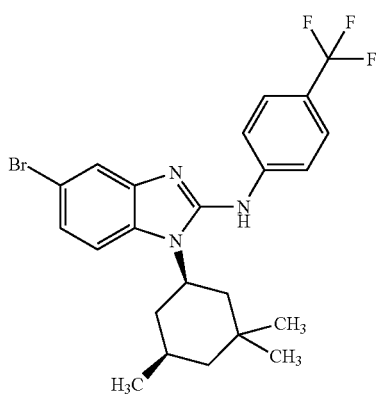

1.5 g (4.82 mmol) (±) 4-Bromo-N$^1$-[(cis)-3,3,5-trimethylcyclohexyl]benzene-1,2-diamine, intermediate 1-1, step 2, were dissolved in 96 mL tetrahydrofurane. After addition of 0.98 g (4.82 mmol) 1-isothiocyanato-4-(trifluoromethyl) benzene (commercially available, CAS-RN: 1645-65-4) and 1.22 g (9.64 mmol) N,N'-diisopropylcarbodiimide the reaction mixture was stirred at 70° C. for two hours. The reaction mixture was evaporated to dryness and the residue was diluted with dichloromethane. After washing with brine and water the organic phase was dried (Na$_2$SO$_4$) and filtered. The solvent was removed and the residue purified by column chromatography yielding 0.88 g (34.4%) of the title compound.

UPLC-MS: R$_t$=1.77 min; m/z=480.1 (ES+, M+1).

$^1$H-NMR (300 MHz, DMSO-d$_6$): δ [ppm]=0.82-1.19 (m, 10H), 1.31-1.50 (m, 2H), 1.63-2.09 (m, 4H), 4.68 (t, 1H), 7.09-7.19 (m, 1H), 7.52-7.62 (m, 2H), 7.68 (d, 2H), 7.90 (d, 2H), 9.38 (s, 1H).

Intermediate 1-4

5-bromo-6-methyl-1-(3,3,5,5-tetramethylcyclohexyl)-N-[4-(trifluoromethoxy)phenyl]-1H-benzimidazol-2-amine

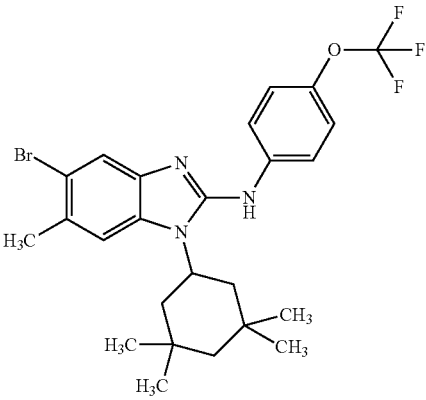 [SMILES: Cc1cc2c(cc1Br)nc(Nc1ccc(OC(F)(F)F)cc1)n2C1CC(C)(C)CC(C)(C)C1]

Step 1: 4-bromo-5-methyl-2-nitro-N-(3,3,5,5-tetramethylcyclohexyl)aniline

To a solution of 1-bromo-4-fluoro-2-methyl-5-nitrobenzene (CAS No. [170098-98-3]; 1.99 g, 8.49 mmol) in DMF (20 mL) with N,N-diisopropylethylamine (4.43 mL, 25.47 mmol) was added 3,3,5,5-tetramethylcyclohexanamine (CAS No. [32939-18-7]; 1.45 g, 9.34 mmol). The reaction was heated at 60° C. for 4 h. The reaction mixture was poured into water (100 mL) and extracted with diethyl ether (3×40 mL). The combined organics were washed with saturated brine solution (20 mL), dried over solid sodium sulfate and concentrated under vacuum to give the title compound (3.0 g, 91%) as an orange solid.

UPLC-MS (Method E): R$_t$=2.49 min; m/z=369/371 (M+H)$^+$.

$^1$H-NMR (300 MHz, CDCl$_3$): δ [ppm]=0.96 (s, 6H), 1.13 (s, 6H), 0.96-1.35 (m, 4H), 1.84 (s, 2H), 2.38 (s, 3H), 6.71 (s, 1H), 7.92 (d, 1H), 8.32 (s, 1H).

Step 2: 4-bromo-5-methyl-N-(3,3,5,5-tetramethylcyclohexyl)benzene-1,2-diamine To a solution of 4-bromo-5-methyl-2-nitro-N-(3,3,5,5-tetramethylcyclohexyl)aniline (3.04 g, 8.23 mmol) from step 1 in water (35 mL) and ethanol (72 mL) were added iron powder (2.29 g, 41.2 mmol) and ammonium chloride (2.20 g, 41.2 mmol) and the reaction was heated at 60° C. for 1.5 h. The reaction was cooled and diluted with ethyl acetate (50 mL) and water (50 mL). The mixture was filtered through celite washing with ethyl acetate (6×50 mL). The filtrate was further diluted with water (100 mL). The layers were split and the aqueous extracted into ethyl acetate (2×50 mL). The combined organics were dried over solid sodium sulfate then concentrated under vacuum. The crude material was purified by flash silica column chromatography (ethyl acetate/hepane) to give the title compound (2.64 g, 94%) as a brown solid. LC-MS (Method A): R$_t$=1.84 (91%); m/z=339/341 (M+H)$^+$.

$^1$H-NMR (300 MHz, CDCl$_3$): δ [ppm]=0.91 (s, 6H), 1.06 (s, 6H), 0.99-1.24 (m, 4H), 1.82 (d, 2H), 2.27 (s, 3H), 3.61(br s, 2H), 6.83-6.97 (m, 2H).

Step 3: 5-bromo-6-methyl-1-(3,3,5,5-tetramethylcyclohexyl)-N-[4-(trifluoromethoxy)phenyl]-1H-benzimidazol-2-amine To a solution of 4-bromo-5-methyl-N-(3,3,5,5-tetramethylcyclohexyl)benzene-1,2-diamine (1.47 g, 4.33 mmol) from step 2 in tetrahydrofuran (32 mL) was added 4-(trifluoromethoxy)phenylisothiocyanate (CAS No. [64285-95-6]; 0.65 mL, 4.33 mmol) and the reaction was stirred at room temperature for 1 h 45 min. 1-(3-Dimethylaminopropyl)-3-ethylcarbodiimide hydrochloride (0.96 g, 4.98 mmol) was added and the reaction was heated at 70° C. for 1 h. The reaction was cooled and poured into a saturated sodium bicarbonate solution (20 mL) then extracted with ethyl acetate (3×20 mL). The combined organics were washed with brine (20 mL), dried over solid sodium sulfate and concentrated under vacuum. The crude material was purified by flash silica column chromatography (ethyl acetate/heptane) to give the title compound (1.83 g, 81%) as a brown solid.

UPLC-MS (Method F): $R_f$=1.20 min; m/z=524/526 (M+H)$^+$.
$^1$H-NMR (300 MHz, CDCl$_3$): δ [ppm]=0.93 (s, 6H), 0.98 (s, 6H), 1.21-1.29 (m, 2H), 1.61 (d, 2H), 1.89 (t, 2H), 2.51 (s, 3H), 4.38 (t, 1H), 7.10-7.30 (m, 6H), 7.73 (s, 1H).

Intermediate 1-5

N-[(1E)-1-(dimethylamino)ethylidene]-6-methyl-1-(3,3,5,5-tetramethylcyclohexyl)-2-{[4-(trifluoromethoxy)phenyl]amino}-1H-benzimidazole-5-carboxamide

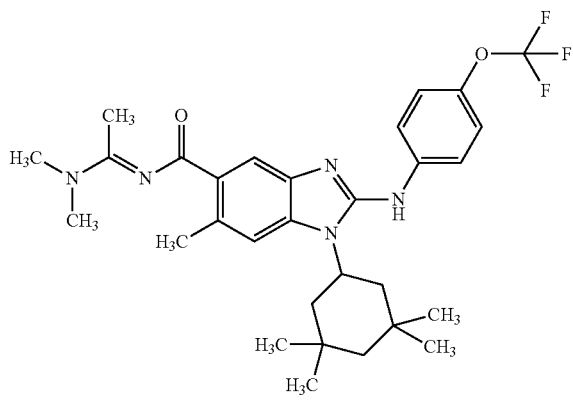 [SMILES: C/C(=N\C(=O)c1cc2nc(Nc3ccc(OC(F)(F)F)cc3)n(C3CC(C)(C)CC(C)(C)C3)c2cc1C)N(C)C]

Step 1: methyl 2-methyl-5-nitro-4-[(3,3,5,5-tetramethylcyclohexyl)amino]benzoate To a solution of methyl 4-fluoro-2-methyl-5-nitrobenzoate (CAS No. [1163287-01-1]; 7.80 g, 36.6 mmol) in DMF (80 mL) were added N,N-diisopropylethylamine (19.11 mL, 109.77 mmol) and 3,3,5,5-tetramethylcyclohexanamine (CAS No. [32939-18-7]; 6.25 g 40.2 mmol). A further 20 mL of DMF was added to fully mobilise the solids, then the reaction was heated for 2.5 h at 60° C. The reaction mixture was poured into water (100 mL) and extracted with ethyl acetate (4×60 mL). The combined organics were washed with saturated brine solution, dried over solid sodium sulfate, concentrated under vacuum and azeotroped with toluene to give the title compound (12.56 g, 98%) as a yellow solid.

UPLC-MS (Method F): $R_f$=1.15 min; m/z=349 (M+H)$^+$.
$^1$H-NMR (300 MHz, CDCl$_3$): δ [ppm]=0.97 (s, 6H), 1.17 (s, 6H), 0.97-1.36 (m, 4H), 1.84 (d, 2H), 2.62 (s, 3H), 3.83 (s, 3H), 3.75-3.90 (m, 1H), 6.62 (s, 1H), 8.17 (d, 1H), 8.87 (s, 1H).

Step 2: methyl 5-amino-2-methyl-4-[(3,3,5,5-tetramethylcyclohexyl)amino]benzoate To a solution of methyl 2-methyl-5-nitro-4-[(3,3,5,5-tetramethylcyclohexyl)amino]benzoate (3.04 g, 8.23 mmol) from step 1 in water (140 mL) and ethanol (288 mL) were added iron powder (10.06 g, 180.2 mmol) and ammonium chloride (9.64 g, 180 mmol). The reaction was heated at 60° C. for 4 h. The reaction mixture was cooled and diluted with ethyl acetate (100 mL) and water (100 mL). The mixture was filtered through celite washing with ethyl acetate (6×75 mL). The filtrate was further diluted with water (100 mL). The layers were split and the aqueous extracted into ethyl acetate (3×100 mL). The combined organics were dried with sodium sulfate then concentrated under vacuum. The crude material was purified by flash silica column chromatography (ethyl acetate/heptane) to give the title compound (10.2 g, 89%) as a brown solid.

LC-MS (Method A): $R_f$=1.33 min; m/z=319 (M+H)$^+$.
$^1$H-NMR (300 MHz, CDCl$_3$): δ [ppm]=0.93 (s, 6H), 1.12 (s, 6H), 0.93-1.33 (m, 2H), 1.87 (d, 2H), 2.53 (s, 3H), 3.65 (t, 2H), 3.81 (s, 3H), 6.42 (s, 1H), 7.39 (s, 3H).

Step 3: methyl 6-methyl-1-(3,3,5,5-tetramethylcyclohexyl)-2-{[4-(trifluoromethoxy)phenyl]amino}-1H-benzimidazole-5-carboxylate To a solution of methyl 5-amino-2-methyl-4-[(3,3,5,5-tetramethylcyclohexyl)amino]benzoate (10.2 g, 32.1 mmol) from step 2 in tetrahydrofuran (200 mL) was added 4-(trifluoromethoxy)phenylisothiocyanate (CAS No. [64285-95-6]; 6.52 g, 32.1 mmol). The reaction was stirred at room temperature for 50 min. 1-(3-Dimethylaminopropyl)-3-ethylcarbodiimide hydrochloride (7.07 g, 36.91 mmol) was then added and the reaction heated at 75° C. for 18 h. The reaction was cooled and poured into a saturated solution of sodium bicarbonate (100 mL) then extracted with ethyl acetate (3×100 mL). The combined organics were washed with brine, dried over sodium sulfate, filtered and concentrated under vacuum. The crude material was purified by flash silica column chromatography (ethyl acetate/heptane) to give the desired ester (15.3 g, 94%) as a sandy yellow foam.

UPLC-MS (Method F): $R_f$=1.12 min; m/z=504 (M+H)$^+$.
$^1$H-NMR (300 MHz, CDCl$_3$): δ [ppm]=0.92 (s, 6H), 0.99 (s, 6H), 1.10-1.30 (m, 2H), 1.65 (d, 2H), 1.92 (t, 2H), 2.72 (s, 3H), 3.90 (s, 3H), 4.42 (t, 1H), 7.12-7.30 (m, 6H), 8.16 (s, 1H).

Step 4: 6-methyl-1-(3,3,5,5-tetramethylcyclohexyl)-2-{[4-(trifluoromethoxy)phenyl]amino}-1H-benzimidazole-5-carboxylic acid To a solution of methyl 6-methyl-1-(3,3,5,5-tetramethylcyclohexyl)-2-{[4-(trifluoromethoxy)phenyl]amino}-1H-benzimidazole-5-carboxylate (2.00 g, 3.97 mmol) from step 3 in methanol (30 mL) and water (3 mL) was added sodium hydroxide (318 mg, 7.94 mmol). The reaction was stirred at 70° C. overnight. The mixture was cooled and acidified with saturated ammonium chloride solution to pH 5. The precipitate was collected by filtration and washed with water (300 mL). The material was then air dried to give the desired acid (1.80 g, 93%) as a colourless solid.

LC-MS (Method B): $R_f$=1.94 min; m/z=490 (M+H)$^+$.

$^1$H-NMR (300 MHz, DMSO-d$_6$): δ [ppm]=0.95 (s, 6H), 1.07 (s, 6H), 1.20-1.37 (m, 2H), 1.52 (d, 2H), 2.02 (t, 2H), 2.60 (s, 3H), 4.57 (t, 1H), 7.30 (d, 2H), 7.44 (s, 1H), 7.61 (d, 2H), 7.85 (s, 1H), 9.00 (s, 1H).

Step 5: 6-methyl-1-(3,3,5,5-tetramethylcyclohexyl)-2-{[4-(trifluoromethoxy)phenyl]amino}-1H-benzimidazole-5-carboxamide 1,1'-Carbonyldiimidazole (331 mg, 2.04 mmol) was added to a solution of 6-methyl-1-(3,3,5,5-tetramethylcyclohexyl)-2-{[4-(trifluoromethoxy)phenyl]amino}-1H-benzimidazole-5-carboxylic acid (500 mg, 1.02 mmol) from step 4 in DMF (25 mL). The reaction was stirred for 3 h at room temperature upon which ammonium carbonate (1.47 g, 15.30 mmol) was added. The reaction was stirred at room temperature for 3 days and at 50° C. for 2 days. The reaction was cooled and water (100 mL) and ethyl acetate (300 mL) were added. The layers were separated and the organics were washed with brine (50 mL). The organic layer was dried over solid sodium sulfate and concentrated under vacuum. The product was then triturated with diethyl ether to give the title compound (550 mg, 97%) as a colourless solid.

UPLC-MS (Method G): R$_t$=0.57 min; m/z=489 (M+H)$^+$.

$^1$H-NMR (300 MHz, CDCl$_3$): δ [ppm]=0.99 (s, 6H), 1.00 (s, 6H), 1.20-1.40 (m, 2H), 1.60-1.67 (m, 4H), 1.94 (t, 2H), 2.64 (s, 3H), 4.40 (m, 1H), 7.20-7.30 (m, 5H), 7.70 (s, 1H).

Step 6: N-[(1E)-1-(dimethylamino)ethylidene]-6-methyl-1-(3,3,5,5-tetramethylcyclohexyl)-2-{[4-(trifluoromethoxy)phenyl]amino}-1H-benzimidazole-5-carboxamide To a solution of 6-methyl-1-(3,3,5,5-tetramethylcyclohexyl)-2-{[4-(trifluoromethoxy)phenyl]amino}-1H-benzimidazole-5-carboxamide (50 mg, 0.10 mmol) from step 5 in toluene (10 mL) N,N-dimethylacetamidedimethyl acetal (136 mg, 1.02 mmol) was added. The reaction mixture was stirred at 50° C. for 5 h, then concentrated under vacuum to give the title compound (50 mg, 88%) as a pale yellow solid. The obtained material was used without further purification.

LC-MS (Method A): R$_t$=1.57 min; m/z=558 (M+H)$^+$.

Intermediate 1-6

N'-Acetyl-1-(3,3,5,5-tetramethylcyclohexyl)-2-{[4-(trifluoromethoxy)phenyl]amino}-1H-benzimidazole-5-carbohydrazide

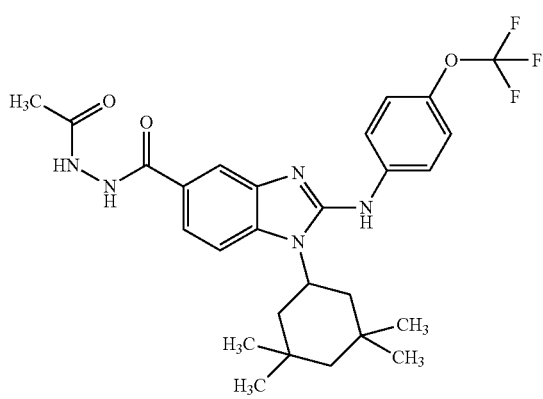 [SMILES: CC(=O)NNC(=O)c1ccc2c(c1)nc(Nc1ccc(OC(F)(F)F)cc1)n2C1CC(C)(C)CC(C)(C)C1]

Step 1: Methyl 3-nitro-4-[(3,3,5,5-tetramethylcyclohexyl)amino]benzoate 0.7 g (3.52 mmol) Methyl-4-fluoro-3-nitrobenzoate (commercially available) and 0.674 g (3.52 mmol) 3,3,5,5-tetramethylcyclohexanamine hydrochloride (commercially available) were given in 7.0 mL tetrahydrofuran. After addition of 0.38 g (2.76 mmol) potassium carbonate the reaction mixture was heated at 50° C. for 24 hours. The reaction mixture was diluted with water The aqueous phase was washed with ethyl acetate and dichloromethane. The combined organic extracts were dired over sodium sulfate. After removal of the solvent 1.19 g of crude product was used without prior purification in the next step.

Step 2: Methyl-3-amino-4-{[3,3,5,5-tetramethylcyclohexyl]amino}benzoate 1.8 g (5.4 mmol) Methyl 3-nitro-4-[(3,3,5,5-tetramethylcyclohexyl)amino]benzoate were dissolved in ethyl acetate (120 mL). After addition of 115 mg (1.10 mmol) Pd/C the reaction mixture was stirred under a hydrogen atmosphere for 20 h at room temperature. After the catalyst was filtered off and removal of solvent the crude product was used without prior purifications.

Step 3: Methyl-2-{[4-(trifluoromethoxy)phenyl]amino}-1-(3,3,5,5-tetramethylcyclohexyl)-1H-benzimidazole-5-carboxylate To a solution of methyl-3-amino-4-{[3,3,5,5-tetramethylcyclohexyl]amino}benzoate (0.2 g, 0.66 mmol) from step 2 in tetrahydrofuran (5.0 mL) was added 4-(trifluoromethoxy)phenylisothiocyanate (CAS No. [64285-95-6]; 117 mg, 0.66 mmol). The reaction was stirred at room temperature for 50 min. N,N'-diisopropylcarbodiimide (166 mg, 1.31 mmol) was then added and the reaction heated at 70° C. for 24 h. After cooling to room temperature, removal of the solvent and subsequent purification of the crude product, 250 mg (80%) of the desired product was obtained.

$^1$H NMR (300 MHz, DMSO-d$_6$) δ ppm 0.97 (s, 6H), 1.12 (s, 6H), 1.22-1.38 (m, 2H), 1.55-1.59 (m, 2H), 2.00-2.09 (m, 2H), 3.83 (s, 3H), 4.52-4.77 (m, 1H), 7.33 (d, 2H), 7.63-7.79 (m, 4H), 7.94 (s, 1H), 9.13 (s, 1H) MS: (ESI+, M+1): 490.

Step 4: 2-{[4-(Trifluoromethoxy)phenyl]amino}-1-(3,3,5,5-tetramethylcyclohexyl)-1H-benzimidazole-5-carboxylic acid Methyl 2-{[4-(trifluoromethoxy)phenyl]amino}-1-(3,3,5,5-tetramethylcyclohexyl)-1H-benzimidazole-5-carboxylate (100 mg, 0.20 mmol) was dissolved in 0.9 mL dioxane. After addition of 9.78 mg (0.41 mmol) LiOH and 0.3 mL water the reaction mixture was stirred at 70° C. for 2.5 hours and then evaporated to dryness. The residue was treated with water (10 mL) and acidified with HCl (1N) to pH4. After stirring at room temperature for two hours the crystals were sucked off and washed with water yielding 100 mg (>100%) of the desired compound which was used in the next step without further purification.

Step 5: N'-Acetyl-1-(3,3,5,5-tetramethylcyclohexyl)-2-{[4-(trifluoromethoxy)phenyl]-amino}-1H-benzimidazole-5-carbohydrazide To a solution of 2-{[4-(trifluoromethoxy)phenyl]amino}-1-(3,3,5,5-tetramethylcyclohexyl)-1H-benzimidazole-5-carboxylic acid (100 mg, 0.21 mmol), step 1, in tetrahydrofuran (5.0 mL) was added aceto hydrazide (18 mg, 0.23 mmol) in the presence of HATU (88 mg, 0.23 mmol) and N,N-diisopropylethylamine (80 µL, 0.44 mmol). The reaction mixture was stirred at 60° C. for 24 h. After removal of the solvent the crude product (330 mg) was used in the next step without further purification.

Intermediate 1-7

N'-Hydroxy-1-(3,3,5,5-tetramethylcyclohexyl)-2-{[4-(trifluoromethoxy)phenyl]-amino}-1H-benzimidazole-5-carboximidamide

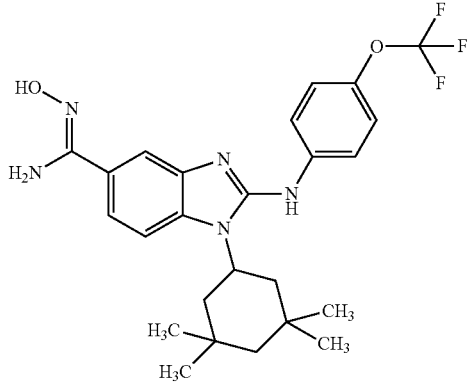 [SMILES: CC1(C)CC(n2c(Nc3ccc(OC(F)(F)F)cc3)nc3cc(/C(N)=N/O)ccc32)CC(C)(C)C1]

Step 1: 3-Nitro-4-[(3,3,5,5-tetramethylcyclohexyl)amino]benzonitrile 0.348 g (2.09 mmol) 4-Fluoro-3-nitrobenzonitrile (commercially available) and 0.402 g (2.09 mmol) 3,3,5,5-tetramethylcyclohexanamine hydrochloride (commercially available) were given in 7.0 mL tetrahydrofuran. After addition of 0.608 g (4.40 mmol) potassium carbonate the reaction mixture was heated at 50° C. for 20 hours. The reaction mixture was diluted with saturated aqueous sodium chloride solution. The aqueous phase was washed with ethyl acetate and dichloromethane. The combined organic extracts were dried over sodium sulfate. After removal of the solvent 0.630 g (98%) of crude product was used without prior purification in the next step.
$^1$H NMR (300 MHz, DMSO-$d_6$) δ ppm 0.91 (s, 6H) 1.03-1.39 (m, 10H) 1.72-1.76 (m, 2H) 3.79-4.07 (m, 1H) 7.19 (d, 1H) 7.84 (dd, 1H) 8.14 (d, 1H) 8.51 (d 1H)

Step 2: 3-Amino-4-{[3,3,5,5-tetramethylcyclohexyl]amino}benzonitrile 0.1 g (0.33 mmol) 3-nitro-4-[(3,3,5,5-tetramethylcyclohexyl)amino]benzonitrile were dissolved in tetrahydrofurane (5.0 mL). After addition of 7 mg (0.07 mmol) Pd/C the reaction mixture was stirred under a hydrogen atmosphere for 3 days at room temperature. After the catalyst was filtered off and removal of solvent the crude product was used without prior purifications.

Step 3: 1-(3,3,5,5-Tetramethylcyclohexyl)-2-{[4-(trifluoromethoxy)phenyl]amino}-1H-benzimidazole-5-carbonitrile 105 mg (0.33 mmol) 3-Amino-4-(3,3,5,5-tetramethylcyclohexylamino)benzonitrile were dissolved in 1.9 mL tetrahydrofurane. 72.9 mg (0.33 mmol) 4-Isothiocyanatophenyl trifluoromethyl ether and 84 mg N,N'-diisopropylcarbodiimide were added and the reaction mixture was stirred at 70° C. for 17 hours. The solvent was removed yielding 211 mg (>100%) of the desired compound which was used in the next step without further purification.

Step 4: N'-Hydroxy-1-(3,3,5,5-tetramethylcyclohexyl)-2-{[4-(trifluoromethoxy)phenyl]-amino}-1H-benzimidazole-5-carboximidamide To a solution of 1-(3,3,5,5-tetramethylcyclohexyl)-2-{[4-(trifluoromethoxy)phenyl]amino}-1H-benzimidazole-5-carbonitrile, (211 mg, step 3) in ethanol (3 mL), was added hydroxylamine (85 µL, 1.4 mmol, 50% solution in water). The reaction was stirred at room temperature for 20 h. After removal of the solvent 245 mg of the compound were obtained as crude product which was used without further purification in the next step.

Intermediate 1-8

(±) 2-{[4-(trifluoromethoxy)phenyl]amino}-1-[(trans)-3,3,5-trimethylcyclohexyl]-1H-benzimidazole-5-carbonitrile

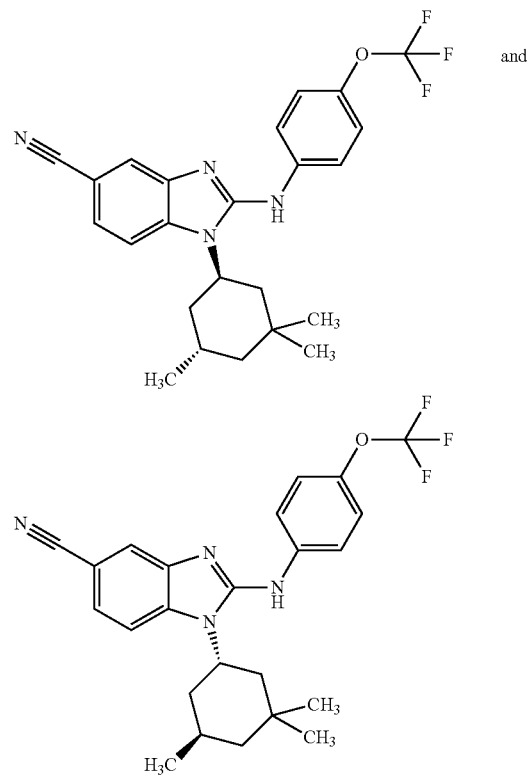

Step 1: (±) 3-nitro-4-{[(trans)-3,3,5-trimethylcyclohexyl]amino}benzonitrile 300 mg (1.8 mmol) 4-Fluor-3-nitrobenzonitril (commercially available) and 255 mg (1.8 mmol) 3,3,5-trimethylcyclohexanamine (mixture of stereoisomers, commercially available) were dissolved in 5 mL tetrahydrofurane. After addition of 524 mg (138 mmol) potassium carbonate the reaction mixture was heated at 50° C. for 45 hours. The solvent was removed and the residue submitted to column chromatography (Biotage SNAP, KP-SIL, eluents: hexane/ethyl acetate) yielding 0.27 g (52%) of the trans diastereomer (as racemate).

$^{1}$H-NMR (300 MHz, CDCl$_3$): δ [ppm]=0.94-1.03 (m, 6H), 1.09 (s, 3H), 1.25-1.38 (m, 2H), 1.45-1.56 (m, 2H), 1.75 (m, 1H), 1.90 (m, 2H), 4.0 (m, 1H), 6.93 (d, 1H), 7.60 (m, 1H), 8.3 (m, 1H).

UPLC-MS (Method A): R$_t$=1.56 min; MS (ES+, M+1) 288.1; MS (ES−, M−1) 286.1.

Step 2: (±) 3-amino-4-{[(trans)-3,3,5-trimethylcyclohexyl]amino}benzonitrile 200 mg (0.69 mmol) (±) 3-Nitro-4-{[(trans)-3,3,5-trimethylcyclohexyl]amino}benzonitrile, step 1, were dissolved in ethyl acetate (10 mL). After addition of 20 mg Pd/C (10% Pd) the reaction mixture was stirred under a hydrogen atmosphere for two hours at room temperature. The catalyst was filtered off via a glass fibre filter and washed with ethyl acetate. The solvent was evaporated and the crude product, (175 mg, 97% yield, trans diastereomer as racemate) was used in the next step without further purification.

$^{1}$H-NMR (300 MHz, DMSO-d$_6$): δ [ppm]=0.86 (s, 3H), 0.92 (m, 6H), 1.20-1.41 (m, 4H), 1.65 (m, 2H), 2.06 (m, 1H), 3.71 (m, 1H), 4.89 (d, 1H), 5.01 (s, 2H), 6.43 (d, 1H), 6.91 (dd, 1H).

UPLC-MS (Method B): R$_t$=1.58 min; MS (ES+, M+1) 443.3; MS (ES−, M−1) 441.3.

Step 3: (±) 2-{[4-(trifluoromethoxy)phenyl]amino}-1-[(trans)-3,3,5-trimethylcyclohexyl]-1H-benzimidazole-5-carbonitrile 225 mg (0.87 mmol) (±) 3-Amino-4-{[(trans)-3,3,5-trimethylcyclohexyl]-amino}benzonitrile, step 2, and 191 mg of 1-isothiocyanato-4-(trifluoromethoxy)benzene were reacted in an analogous manner to Intermediate 1-7 step 1, yielding 168 mg (41%) of the desired compound.

$^{1}$H-NMR (300 MHz, DMSO-d$_6$): δ [ppm]=0.98 (s, 3H), 1.06-1.15 (s, 6H), 1.20-1.30 (m, 2H) 1.40-1.53 (m, 2H), 1.42-1.55 (m, 2H), 1.64 (br., m, 1H), 2.19-2.37 (m, 2H), 4.74 (br. m, 1H), 7.34 (s, 1H), 7.37 (s, 1H), 7.41(dd, 1H), 7.73 (d, 1H) 7.70-7.82 (m, 3H), 9.23 (s, 1H).

UPLC-MS (Method A): R$_t$=1.60 min; MS (ES+, M+1) 288.1; MS (ES−, M−1) 286.1.

Intermediate 1-9

5-(4,4,5,5-tetramethyl-1,3,2-dioxaborolan-2-yl)-N-[4-(trifluoromethoxy)phenyl]-1-(3,3,5-trimethylcyclohexyl)-1H-benzimidazol-2-amine

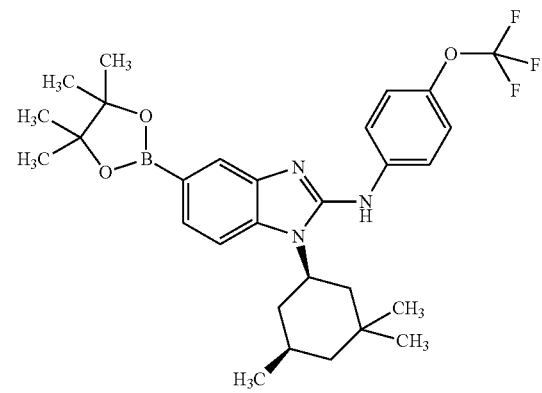

and

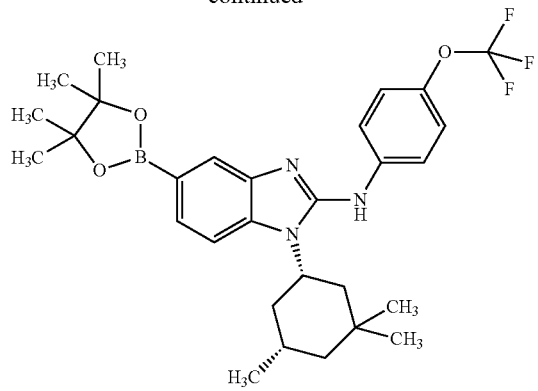

3 g (6.04 mmol) (±) 5-Bromo-N-[4-(trifluoromethoxy)phenyl]-1-[(cis)-3,3,5-trimethylcyclohexyl]-1H-benzimidazol-2-amine, intermediate 1-1, 2.3 g (9.07 mmol) bis(pinacolato)diboron, 1.78 g (19.13 mmol) potassium acetate and 0.49 g (0.60 mmol) 1,1'-(bisdiphenylphosphino)ferrocenedichloropalladium(II) were heated in 35 mL THF (degassed) at 80° C. for three hours. Due to an incomplete reaction additional catalyst was added and heating was continued at 100° C. for four hours. The reaction mixture was cooled, diluted with water and extracted three times with dichloromethane. The combined organic extracts were washed with brine and dried (Na$_2$SO$_4$). The solvent was evaporated and the residue (2.62 g=71.2%) was used without further purification.

UPLC-MS: R$_t$=1.60 min; m/z=544.3 (M+1).

$^{1}$H-NMR (400 MHz, DMSO-d$_6$): δ [ppm]=0.91-1.10 (m, 10H), 1.29 (s, 12H), 1.40 (d, 2H), 1.68-1.95 (m, 3H), 2.02 (t, 1H), 4.65 (t, 1H), 7.28-7.39 (m, 3H), 7.53 (d, 1H), 7.66 (s, 1H), 7.79 (d, 2H), 9.04 (s, 1H).

Intermediate 1-10 ethyl [5-(2,4-dioxo-1,3-oxazolidin-5-yl)-6-methyl-1-(3,3,5,5-tetramethylcyclohexyl)-1H-benzimidazol-2-yl][4-(trifluoromethoxy)phenyl]carbamate

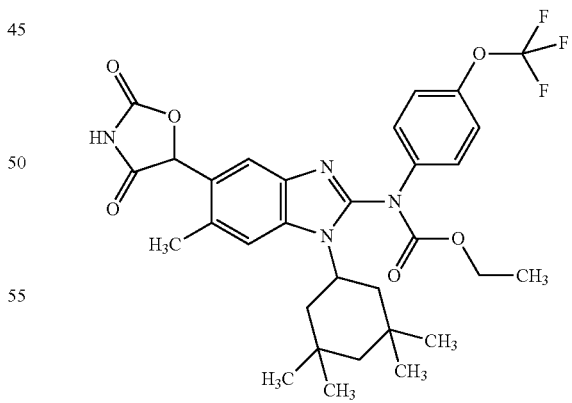

Step 1: [6-methyl-1-(3,3,5,5-tetramethylcyclohexyl)-2-{[4-(trifluoromethoxy)phenyl]amino}-1H-benzimidazol-5-yl]methanol Lithium aluminium hydride (151 mg, 3.90 mmol) was suspended in tetrahydrofuran (15 mL) under argon then cooled to 0° C. A solution of methyl 6-methyl-1-(3,3,5,5-tetramethylcyclohexyl)-2-{[4-(trifluoromethoxy)phenyl]amino}-1H-benzimidazole-5-carboxylate (1.0 g, 1.98 mmol) from step 3 of intermediate 1-5 in tetrahydrofuran (10 mL) was added drop-wise. The reaction was stirred at 0° C. for 30 min then at room temperate for 1 h. Sodium sulfate decahydrate was added until evolution of gas ceased. The mixture was then filtered through celite, washing with ethyl acetate. The filtrate was evaporated to give a pale brown waxy solid, which was triturated with dichloromethane to give the title compound (0.69 g, 73%) as a white powder.

UPLC-MS (Method F) $R_t$=1.02 min; m/z=476 (M+H)$^+$.

$^1$H-NMR (300 MHz, CDCl$_3$): δ [ppm]=0.91 (s, 6H), 0.97 (s, 6H), 1.28 (m, 2H), 1.60 (d, 2H), 1.98 (m, 4H), 2.49 (s, 3H), 4.41 (tt, 1H), 4.75 (s, 2H), 7.17 (m, 4H), 7.20 (s, 1H), 7.56 (s, 1H)

Step 2: 6-methyl-1-(3,3,5,5-tetramethylcyclohexyl)-2-{[4-(trifluoromethoxy)phenyl]-amino}-1H-benzimidazole-5-carbaldehyde

[6-Methyl-1-(3,3,5,5-tetramethylcyclohexyl)-2-{[4-(trifluoromethoxy)phenyl]amino}-1H-benzimidazol-5-yl]methanol (690 mg, 1.40 mmol) from step 1 was dissolved in tetrahydrofuran (15 mL), stabilised 2-iodoxybenzoic acid (1.08 g, 1.70 mmol, 45 wt. %) was added and the flask was wrapped in foil. The reaction was stirred at room temperature for 8 h. The purple solution was diluted with ethyl acetate then washed twice with a saturated sodium bicarbonate solution. The aqueous layer was extracted with ethyl acetate and the combined organic layers were washed with brine, dried over sodium sulfate and concentrated under vacuum to give an indigo solid. The crude was triturated with heptane, filtered and washed with heptane to give the title compound (415 mg, 60%) as a pale reddish solid.

UPLC-MS (Method G): $R_t$=0.86 min; m/z=474 (M+H)$^+$.

$^1$H-NMR (300 MHz, CDCl$_3$): δ [ppm]=1.00 (s, 12H), 1.21 (d, 1H), 1.34 (d, 1H), 1.68 (d, 2H), 1.97 (d, 2H), 2.79 (s, 3H), 4.47 (m, 1H), 7.17 (m, 3H), 7.32 (m, 2H), 7.96 (s, 1H) 10.24 (s, 1H).

Step 3: cyano[2-{(ethoxycarbonyl)[4-(trifluoromethoxy)phenyl]amino}-6-methyl-1-(3,3,5,5-tetramethylcyclohexyl)-1H-benzimidazol-5-yl]methyl ethyl carbonate To a solution of 6-methyl-1-(3,3,5,5-tetramethylcyclohexyl)-2-{[4-(trifluoromethoxy)-phenyl]amino}-1H-benzimidazole-5-carbaldehyde (50 mg, 0.11 mmol) from step 2 in acetonitrile (4 mL), ethyl cyanoformate (13 mg, 0.13 mmol) and 4-dimethyl-aminopyridine (2 mg, 0.02 mmol) were added. The reaction mixture was stirred at room temperature for 3 h then additional ethyl cyanoformate (13 mg, 0.13 mmol) was added. After a further 6 h the reaction was quenched by addition of brine (20 mL) and the mixture was extracted with ethyl acetate (3×20 mL). The combined organic layers were dried over solid sodium sulfate and concentrated under vacuum to give the title compound (51 mg, 75%) as a yellow oil, which was used without further purification.

UPLC-MS (Method G): $R_t$=0.96 min; m/z=645 (M+H)$^+$.

$^1$H-NMR (300 MHz, CDCl$_3$): δ [ppm]=0.85-1.10 (m, 12H), 1.10-1.70 (m, 10H), 1.85-2.00 (m, 2H), 2.56 (s, 3H), 4-00-4.20 (m, 5H), 6.47 (s, 1H), 7.22 (d, 2H), 7.40 (d, 2H), 7.99 (s, 1H), 8.26 (m, 1H).

Step 4: 2-amino-1-[2-{(ethoxycarbonyl)[4-(trifluoromethoxy)phenyl]amino}-6-methyl-1-(3,3,5,5-tetramethylcyclohexyl)-1H-benzimidazol-5-yl]-2-oxoethyl ethyl carbonate Cyano[2-{(ethoxycarbonyl)[4-(trifluoromethoxy)phenyl]amino}-6-methyl-1-(3,3,5,5-tetra-methylcyclohexyl)-1H-benzimidazol-5-yl]methyl ethyl carbonate (51 mg, 0.08 mmol) from step 3 was dissolved in hydrochloric acid (5 mL, 20 mmol, 4 M in dioxane), aqueous hydrochloric acid (5 mL, 55 mmol, 11 M) was added at 0° C. and the reaction was stirred at this temperature for 30 min and at room temperature for 4 h. The reaction was quenched by addition of water (100 mL) and the resulting precipitate was collected by filtration. The solid was washed with water (50 mL) then azeotroped with toluene (3×15 mL) to give the title compound (56 mg, 89%) as a colourless solid.

UPLC-MS (Method G): $R_t$=0.76 min; m/z=663 (M+H)$^+$.

$^1$H-NMR (300 MHz, CDCl$_3$): δ [ppm]=0.85-1.10 (m, 12H), 1.10-1.70 (m, 10H), 1.85-2.00 (m, 2H), 2.67 (s, 3H), 4-00-4.20 (m, 5H), 5.64 (s, 1H) 6.28 (s, 1H), 6.47 (s, 1H), 7.20-8.00 (m, 6H).

Step 5: ethyl [5-(2,4-dioxo-1,3-oxazolidin-5-yl)-6-methyl-1-(3,3,5,5-tetramethylcyclohexyl)-1H-benzimidazol-2-yl][4-(trifluoromethoxy)phenyl]carbamate 2-Amino-1-[2-{(ethoxycarbonyl)[4-(trifluoromethoxy)phenyl]amino}-6-methyl-1-(3,3,5,5-tetramethylcyclohexyl)-1H-benzimidazol-5-yl]-2-oxoethyl ethyl carbonate (56 mg, 0.07 mmol) from step 4 was dissolved in acetonitrile (5 mL), 1,8-diazabicyclo(5.4.0)undec-7-ene (13 mg, 0.08 mmol) was added and the reaction stirred at room temperature for 5 h. The solvent was removed by evaporation and the residue dissolved in ethyl acetate (50 mL). The organic layer was washed with water (15 mL) and brine (15 mL), dried over solid sodium sulfate and concentrated under vacuum to give the title compound (42 mg, 94%) as yellow oil, which was used without further purification.

UPLC-MS (Method F): $R_t$=0.78 min; m/z=617 (M+H)$^+$.

$^1$H-NMR (300 MHz, CDCl$_3$): δ [ppm]=0.85-1.60 (m, 17H), 1.60-180 (m, 2H), 1.94 (t, 2H), 2.61 (s, 3H), 4.16 (t, 2H), 4.40 (m, 1H), 6.22 (br s, NH), 6.80 (m, 3H), 6.99 (d, 1H), 7.07 (d, 2H), 7.45 (d, 1H).

Intermediate 1-11

N-hydroxy-2-{2-[6-methyl-1-(3,3,5,5-tetramethylcyclohexyl)-2-{[4-(trifluoromethoxy)phenyl]amino}-1H-benzimidazol-5-yl]-1,3-dioxolan-2-yl}acetamide

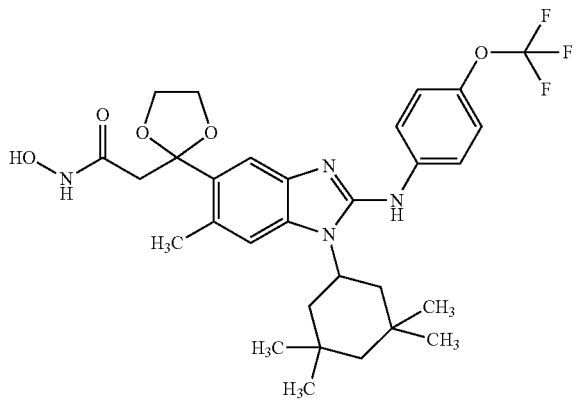 [SMILES: Cc1cc2c(cc1C1(CC(=O)NO)OCCO1)nc(Nc1ccc(OC(F)(F)F)cc1)n2C1CC(C)(C)CC(C)(C)C1]

Step 1: ethyl 3-[6-methyl-1-(3,3,5,5-tetramethylcyclohexyl)-2-{[4-(trifluoromethoxy)-phenyl]amino}-1H-benzimidazol-5-yl]-3-oxopropanoate 6-Methyl-1-(3,3,5,5-tetramethylcyclohexyl)-2-{[4-(trifluoromethoxy)phenyl]amino}-1H-benzimidazole-5-carboxylic acid (200 mg, 0.98 mmol) from step 4 of intermediate 1-5 was added to a suspension of 1,1'-carbonyldiimidazole (166 mg, 0.41 mmol) in N,N-dimethylformamide (15 mL). The resulting mixture was stirred for 4 h at 50° C. Magnesium chloride (93 mg, 0.98 mmol) and ethyl potassium malonate (167 mg, 0.98 mmol) were added and the solution stirred at 110° C. overnight. The reaction was quenched by addition of water (100 mL) and the resulting precipitate was collected by vacuum filtration. The solid was dissolved in ethyl acetate (100 mL) and washed twice with aqueous hydrochloridic acid (1 M, 50 mL). The organic layer was then dried over solid sodium sulfate and concentrated under vacuum. The crude material was purified by flash silica column chromatography (dichloromethane) to give the title compound (210 mg, 92%) as a pale yellow solid.

UPLC-MS (Method F): $R_t$=1.08 min; m/z=560 (M+H)$^+$.
$^1$H-NMR (300 MHz, CDCl$_3$): δ [ppm]=1.03 (s, 6H), 1.21 (s, 6H), 1.10-1.40 (m, 5H), 1.60-1.70 (m, 2H), 1.85-2.00 (m, 2H), 2.56 (s, 3H), 4.03 (s, 2H), 4.21 (q, 2H, 4.38 (m, 1H), 7.10-7.30 (m, 5H), 7.95 (s, 1H).

Step 2: ethyl {2-[6-methyl-1-(3,3,5,5-tetramethylcyclohexyl)-2-{[4-(trifluoromethoxy)phenyl]amino}-1H-benzimidazol-5-yl]-1,3-dioxolan-2-yl}acetate and 2-hydroxyethyl{2-[6-methyl-1-(3,3,5,5-tetramethylcyclohexyl)-2-{[4-(trifluoromethoxy)phenyl]amino}-1H-benzimidazol-5-yl]-1,3-dioxolan-2-yl}acetate Ethyl 3-[6-methyl-1-(3,3,5,5-tetramethylcyclohexyl)-2-{[4-(trifluoromethoxy)phenyl]amino}-1H-benzimidazol-5-yl]-3-oxopropanoate (100 mg, 0.18 mmol) from step 1 was dissolved in 1,2-ethanediol (5 mL) followed by addition of methanesulfonic acid (0.001 mL, 0.02 mmol) and stirred at 30° C. for 5 h. The reaction was quenched by addition of ammonia (30 mL, 28% in water) and the resulting precipitate was collected by vacuum filtration. The solid was dissolved in ethyl acetate (50 mL) and washed with water (2×20 mL). The organic layer was dried over solid sodium sulfate and concentrated under vacuum to give a mixture of ethyl 3-[6-methyl-1-(3,3,5,5-tetramethylcyclohexyl)-2-{[4-(trifluoromethoxy)phenyl]amino}-1H-benzimidazol-5-yl]-3-oxopropanoate, ethyl {2-[6-methyl-1-(3,3,5,5-tetramethylcyclohexyl)-2-{[4-(trifluoromethoxy)phenyl]amino}-1H-benzimidazol-5-yl]-1,3-dioxolan-2-yl}acetate and 2-hydroxyethyl {2-[6-methyl-1-(3,3,5,5-tetramethylcyclohexyl)-2-{[4-(trifluoromethoxy)phenyl]amino}-1H-benzimidazol-5-yl]-1,3-dioxolan-2-yl}acetate (112 mg) as pale yellow oil, which was used in the next step without further purification.

UPLC-MS (Method G): $R_t$=0.89 min; m/z=560 (M+H)$^+$; $R_t$=0.92 min; m/z=604 (M+H)$^+$; $R_t$=0.73 min; m/z=620 (M+H)$^+$.

Step 3: {2-[6-methyl-1-(3,3,5,5-tetramethylcyclohexyl)-2-{[4-(trifluoromethoxy)-phenyl]amino}-1H-benzimidazol-5-yl]-1,3-dioxolan-2-yl}acetic acid A mixture of ethyl 3-[6-methyl-1-(3,3,5,5-tetramethylcyclohexyl)-2-{[4-(trifluoromethoxy)phenyl]amino}-1H-benzimidazol-5-yl]-3-oxopropanoate, ethyl {2-[6-methyl-1-(3,3,5,5-tetramethylcyclohexyl)-2-{[4-(trifluoromethoxy)phenyl]amino}-1H-benzimidazol-5-yl]-1,3-dioxolan-2-yl}acetate and 2-hydroxyethyl {2-[6-methyl-1-(3,3,5,5-tetramethylcyclohexyl)-2-{[4-(trifluoromethoxy)phenyl]amino}-1H-benzimidazol-5-yl]-1,3-dioxolan-2-yl}acetate (112 mg) from step 2 were dissolved in a mixture of methanol (4 mL) and water (1 mL). Sodium hydroxide (12 mg, 0.23 mmol) was added and the reaction was stirred at room temperature overnight. The methanol was removed by evaporation and the residual mixture was acidified with aqueous hydrochloric acid (1 M) and then extracted with ethyl acetate (3×50 mL). The combined organic layers were dried over solid sodium sulfate and concentrated under vacuum to give the title compound (60 mg, 58% yield over two steps) as a colourless solid which was used without further purification.

UPLC-MS (Method F): $R_t$=0.89 min; m/z=574 (M+H)$^+$.
$^1$H-NMR (300 MHz, CDCl$_3$): δ [ppm]=0.57 (s, 6H), 0.90 (s, 6H), 1.00-1.24 (m, 2H), 1.40-1.50 (d, 2H), 1.85 (t, 2H), 2.64 (s, 3H), 3.18 (s, 2H), 3.78 (s, 2H), 4.14 (m, 1H), 6.98 (d, 2H), 7.12 (m, 3H), 8.14 (s, 1H).

Step 4: N-hydroxy-2-{2-[6-methyl-1-(3,3,5,5-tetramethylcyclohexyl)-2-{[4-(trifluoromethoxy)phenyl]amino}-1H-benzimidazol-5-yl]-1,3-dioxolan-2-yl}acetamide To a solution of 1,1'-carbonyldiimidazole (34 mg, 0.21 mmol) in N,N-dimethylformamide (5 mL), {2-[6-methyl-1-(3,3,5,5-tetramethylcyclohexyl)-2-{[4-(trifluoromethoxy)phenyl]amino}-1H-benzimidazol-5-yl]-1,3-dioxolan-2-yl}acetic acid (60 mg, 0.10 mmol) from step 3 was added. The resulting mixture was stirred at 50° C. for 4 h. After the addition of hydroxylamine hydrochloride (15 mg, 0.21 mmol) the mixture was stirred at 50° C. for a further 4 h. The reaction was then quenched by addition of water (20 mL) and extracted with ethyl acetate (3×50 mL). The combined organic layers were dried over solid sodium sulfate and concentrated under vacuum to give intermediate 1-11 (68 mg, 51%) as a colourless solid which was used without further purification.

LCMS (Method C): $R_t$=2.28 min; m/z=591 (M+H)$^+$.

EXAMPLES

Example 2-1 (±) 5-(3,5-dimethyl-1,2-oxazol-4-yl)-N-[4-(trifluoromethoxy)phenyl]-1-[(cis)-3,3,5-trimethylcyclohexyl]-1H-benzimidazol-2-amine

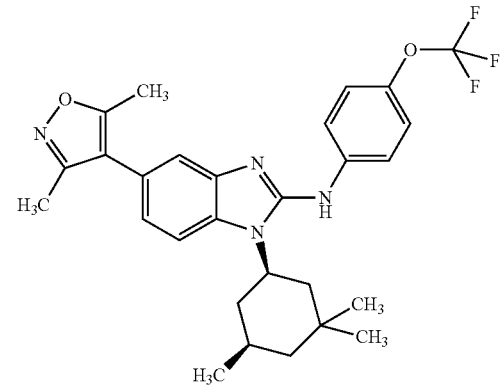

and

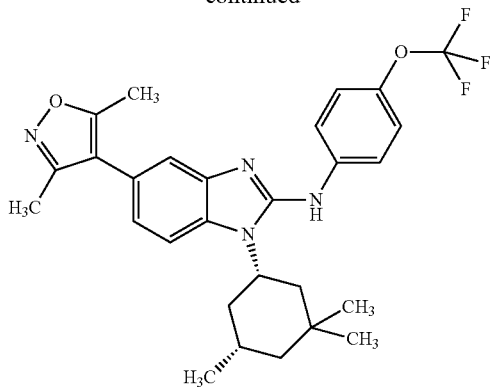

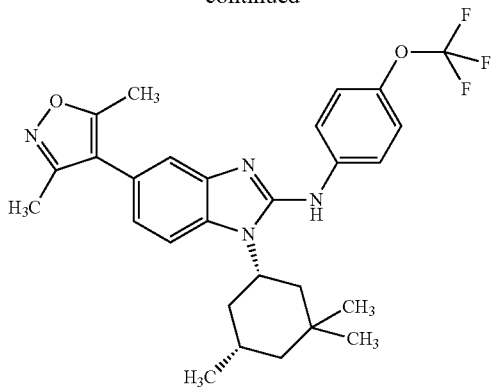

150 mg (0.30 mmol) (±) 5-Bromo-N-[4-(trifluoromethoxy)phenyl]-1-[(cis)-3,3,5-trimethylcyclohexyl]-1H-benzimidazol-2-amine (intermediate 1-1), 85.2 mg (0.60 mmol) (3,5-dimethyl-1,2-oxazol-4-yl)boronic acid (commercially available, CAS-RN: 16114-47-9), 24.7 mg (0.03 mmol) 1,1'-(bisdiphenylphosphino)ferrocenedichloropalladium(II) and 96.1 mg (0.91 mmol) $Na_2CO_3$ in 3.2 mL dioxane and 0.46 mL water (both solvents have been degassed) were heated in the microwave oven at 110° C. for 60 min. The reaction mixture was given on a flash column and was washed with ethyl acetate (250 mL) to remove the catalyst and the salts. The filtrate was evaporated to dryness and the residue was purified by column chromatography to yield 103.1 mg (66.6%) of the title compound.

UPLC-MS: $R_t$=1.53 min; m/z=513.2 (ES+, M+1).

$^1$H-NMR (400 MHz, DMSO-$d_6$): δ [ppm]=0.92-1.02 (m, 6H), 1.02-1.22 (m, 4H), 1.34-1.50 (m, 2H), 1.72-1.97 (m, 3H), 2.07 (t, 1H), 2.22 (s, 3H), 2.41 (s, 3H), 4.68 (t, 1H), 6.93-7.03 (m, 1H), 7.26-7.40 (m, 3H), 7.61 (d, 1H), 7.82 (d, 2H), 9.07 (s, 1H).

The racemic compound (±) 5-(3,5-dimethyl-1,2-oxazol-4-yl)-N-[4-(trifluoromethoxy)-phenyl]-1-[(cis)-3,3,5-trimethylcyclohexyl]-1H-benzimidazol-2-amine (example 2-1; 67 mg) was separated via chiral HPLC (system: Agilent Prep 1200, 2×Prep Pump, DLA, MWD, Prep FC; column: Chiralpak IA, 5 μM 250×20 mm; injection: 67 mg in 4×0.5 mL acetone/DMSO; solvent: hexane, 2-propanol, diethylamine (70:30:0.1); flow: 25 mL/min; detection: UV 254 nm) into its enantiomers yielding 20 mg of the title compound (enantiomer A, retention time range: 4.8-7.0 min) and 25 mg of enantiomer B, described in example 2-1-2.

$^1$H-NMR (400 MHz, CDCl$_3$): δ [ppm]=0.90-1.02 (m, 6H), 1.02-1.17 (m, 4H), 1.34-1.52 (m, 2H), 1.72-1.96 (m, 3H), 2.07 (t, 1H), 2.22 (s, 3H), 2.39 (s, 3H), 4.68 (t, 1H), 6.98 (dd, 1H), 7.27-7.40 (m, 3H), 7.61 (d, 1H), 7.77-7.88 (m, 2H), 9.07 (s, 1H).

Example 2-1-1 5-(3,5-dimethyl-1,2-oxazol-4-yl)-N-[4-(trifluoromethoxy)phenyl]-1-[(cis)-3,3,5-trimethylcyclohexyl]-1H-benzimidazol-2-amine, enantiomer A Example 2-1-2 5-(3,5-dimethyl-1,2-oxazol-4-yl)-N-[4-(trifluoromethoxy)phenyl]-1-[(cis)-3,3,5-trimethylcyclohexyl]-1H-benzimidazol-2-amine, enantiomer B

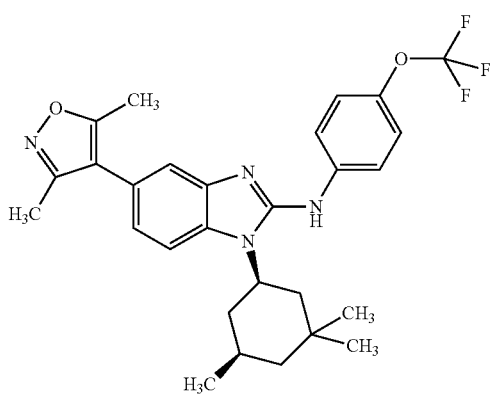

or

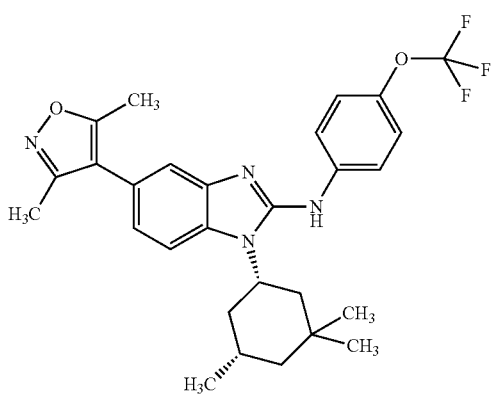

or

-continued

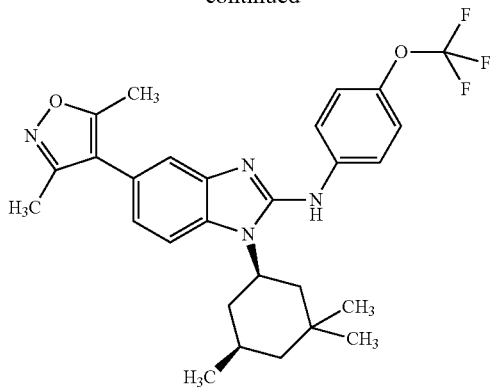

The racemic compound (±) 5-(3,5-dimethyl-1,2-oxazol-4-yl)-N-[4-(trifluoromethoxy)-phenyl]-1-[(cis)-3,3,5-trimethylcyclohexyl]-1H-benzimidazol-2-amine (example 2-1; 67 mg) was separated via chiral HPLC (system: Agilent Prep 1200, 2×Prep Pump, DLA, MWD, Prep FC; column: Chiralpak IA, 5 μM 250×20 mm; injection: 67 mg in 4×0.5 mL acetone/DMSO; solvent: hexane, 2-propanol, diethylamine (70:30:0.1); flow: 25 mL/min; detection: UV 254 nm) into its enantiomers yielding 25 mg of the title compound (enantiomer B, retention time range: 10.5-13.8 min) and 20 mg of enantiomer A, described in example 2-1-1.

$^1$H-NMR (400 MHz, DMSO-d$_6$): δ [ppm]=0.89-1.02 (m, 6H), 1.02-1.19 (m, 4H), 1.32-1.54 (m, 2H), 1.70-1.97 (m, 3H), 2.07 (t, 1H), 2.22 (s, 3H), 2.39 (s, 3H), 4.68 (br. s., 1H), 6.98 (dd, 1H), 7.25-7.43 (m, 3H), 7.61 (d, 1H), 7.72-7.92 (m, 2H), 9.07 (s, 1H).

Example 2-2 (±) 3-(2-{[4-(trifluoromethoxy)phenyl]amino}-1-[(cis)-3,3,5-trimethylcyclohexyl]-1H-benzimidazol-5-yl)benzoic acid

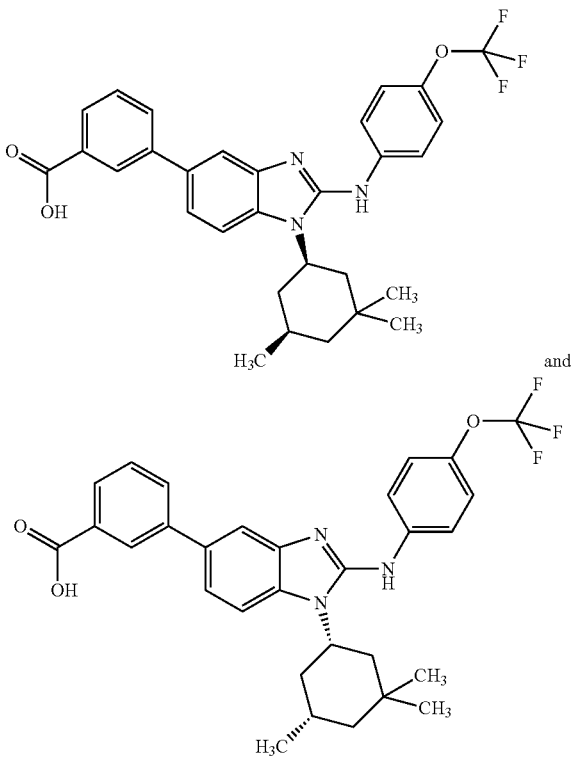

and 100 mg (0.18 mmol) (±) Methyl 3-(2-{[4-(trifluoromethoxy)phenyl]amino}-1-[(cis)-3,3,5-trimethylcyclohexyl]-1H-benzimidazol-5-yl)benzoate (example 2-15) were dissolved in 0.8 mL dioxane. 8.7 mg (0.36 mml) LiOH and 0.26 mL water were added and the reaction mixture was stirred at 70° C. for 2.5 hours. The reaction mixture was evaporated to dryness and the residue was suspended in water (10 mL). After acidification of the mixture to pH 4 (1N HCl) the reaction mixture was stirred for two hours at room temperature. The solid was filtered off, washed with water and dried overnight yielding 75.8 mg (73.9%) of the title compound.

UPLC-MS: R$_t$=1.37 min; m/z=538.2 (ES+, M+1).

$^1$H-NMR (400 MHz, DMSO-d$_6$): δ [ppm]=0.88-1.18 (m, 10H), 1.38-1.56 (m, 2H), 1.72-1.98 (m, 3H), 2.08 (t, 1H), 4.71 (br., 1H), 7.30-7.43 (m, 3H), 7.57 (t, 1H), 7.63-7.73 (m, 2H), 7.82 (d, 2H), 7.85-7.98 (m, 2H), 8.17 (s, 1H), 9.32 (br., 1H), 12.99 (br., 1H).

Example 2-3 (±) 4-(2-{[4-(trifluoromethoxy)phenyl]amino}-1-[(cis)-3,3,5-trimethylcyclohexyl]-1H-benzimidazol-5-yl)benzoic acid

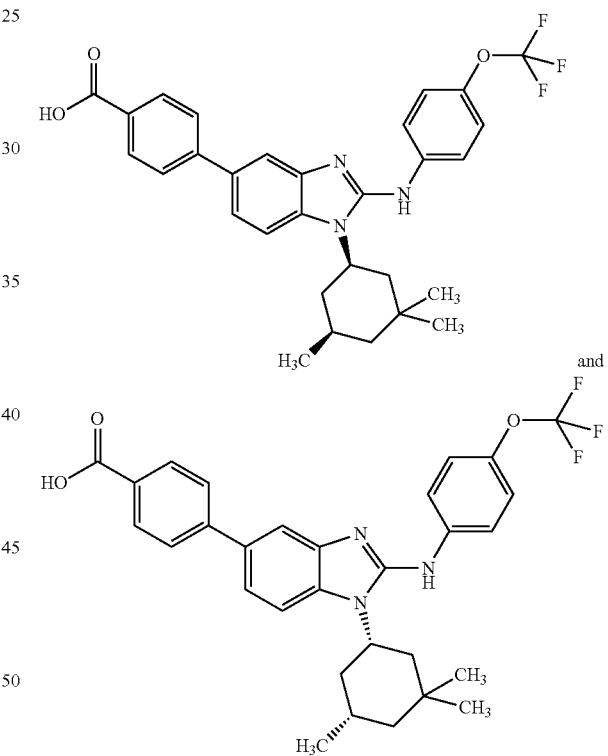

100 mg (0.18 mmol) (±) Methyl 4-(2-{[4-(trifluoromethoxy)phenyl]amino}-1-[(cis)-3,3,5-trimethylcyclohexyl]-1H-benzimidazol-5-yl)benzoate (example 2-18) were dissolved in 0.8 mL dioxane. 8.7 mg (0.36 mml) LiOH and 0.26 mL water were added and the reaction mixture was stirred at 70° C. for 2.5 hours. The reaction mixture was evaporated to dryness and the residue was suspended in water (10 mL). After acidification of the mixture to pH 4 (1N HCl) the reaction mixture was stirred for two hours at room temperature. The solid was filtered off, washed with water and dried overnight yielding 80.5 mg (78.5%) of the title compound.

UPLC-MS: R$_t$=1.43 min; m/z=538.2 (ES+, M+1).

¹H-NMR (400 MHz, DMSO-d₆): δ [ppm]=0.92-1.18 (m, 10H), 1.32-1.47 (m, 1H), 1.53 (d, 1H), 1.70-2.02 (m, 3H), 2.09 (t, 1H), 4.77 (t, 1H), 7.23-7.44 (m, 2H), 7.47 (d, 1H), 7.70 (s, 1H), 7.72-7.84 (m, 5H), 7.92-8.14 (m, 2H), 9.85 (br. 1H), 12.87 (br., 1H).

The examples in Table 1 were prepared in an analogous manner to example 2-1, by reacting the corresponding intermediates and the correponding boronic acids and—where appropriate—separated into their enantiomers as described.

TABLE 1

| Example, (intermediate; boronic acid: CAS-RN) | Structure/Name | Methods/analytical data |
|---|---|---|
| 2-4, (1-1, 1188405-87-9) | 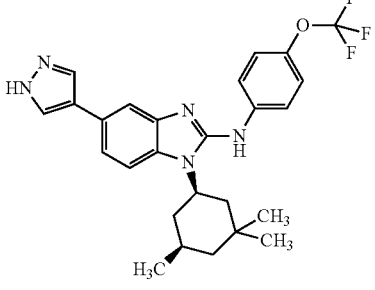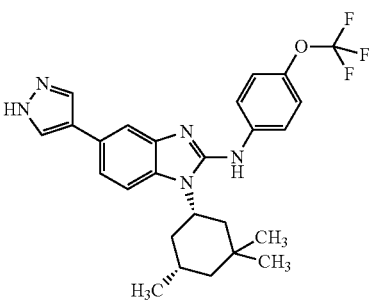<br>(±)5-(1H-pyrazol-4-yl)-N-[4-(trifluoromethoxy)phenyl]-1-[(cis)-3,3,5-trimethylcyclohexyl]-1H-benzimidazol-2-amine | UPLC-MS: R$_t$ = 1.29 min; m/z = 484.2 (ES+, M + 1). ¹H-NMR (400 MHz, DMSO-d₆): δ [ppm] = 0.93-1.01 (m, 6H), 1.01-1.24 (m, 4H), 1.31-1.49 (m, 2H), 1.67-1.96 (m, 3H), 2.05 (t, 1H), 4.64 (t, 1H), 7.16-7.36 (m, 3H) 7.48 (d, 1H), 7.60-7.70 (m, 1H), 7.75-7.95 (m, 3H), 8.09 (br., 1H), 9.01 (s, 1H), 12.79 (br., 1H). |
| 2-4-1 | 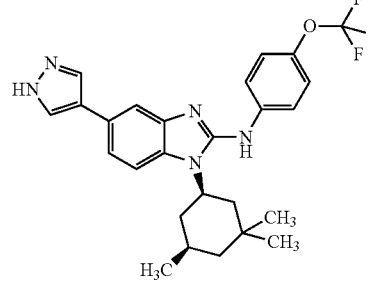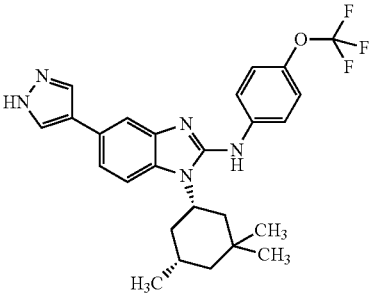<br>5-(1H-pyrazol-4-yl)-N-[4-(trifluoromethoxy)phenyl]-1-[(cis)-3,3,5-trimethylcyclohexyl]-1H-benzimidazol-2-amine, enantiomer A | System: Agilent Prep 1200, 2xPrep Pump, DLA, MWD, Prep FC; column: Chiralpak ID, 5 μM 250 × 30 mm; injection: 25 mg in 1 × 4 mL dichloromethane/methanol (1:1); solvent: hexane/2-propanol/diethylamine (70:30:0.1); flow: 50 mL/min; detection: UV 254 nm; R$_t$ = 21.6-28.0 min. ¹H-NMR (300 MHz, DMSO-d₆): δ [ppm] = 0.91-1.01 (m, 6H), 1.01-1.18 (m, 4H), 1.28-1.51 (m, 2H), 1.66-1.94 (m, 3H), 2.05 (t, 1H), 4.64 (br., 1H), 7.19-7.40 (m, 3H), 7.48 (d, 1H), 7.63 (d, 1H), 7.82 (d, H), 7.75-8.19 (very br., 2H), 9.00 (s, 1H), 12.78 (br., 1H). |

| Example, (intermediate; boronic acid: CAS-RN) | Structure/Name | Methods/analytical data |
|---|---|---|
| 2-4-2 | 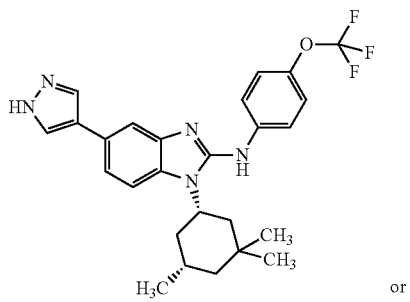 [SMILES: C[C@@H]1C[C@H](n2c(Nc3ccc(OC(F)(F)F)cc3)nc3cc(-c4cn[nH]c4)ccc32)CC(C)(C)C1] or 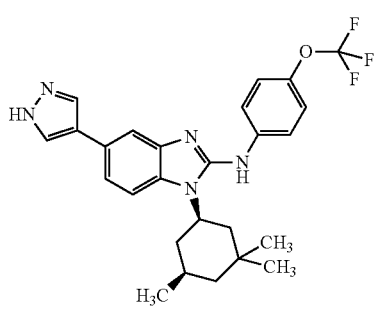<br>5-(1H-pyrazol-4-yl)-N-[4-(trifluoromethoxy)phenyl]-1-[(cis)-3,3,5-trimethylcyclohexyl]-1H-benzimidazol-2-amine, enantiomer B | System: Agilent Prep 1200, 2xPrep Pump, DLA, MWD, Prep FC; column: Chiralpak ID, 5 μM 250 × 30 mm; injection: 25 mg in 1 × 4 mL dichloromethane/methanol (1:1); solvent: hexane/2-propanol/diethylamine (70:30:0.1); flow: 50 mL/min; detection: UV 254 nm; $R_t$ = 28.0-34.1 min.<br>$^1$H-NMR (300 MHz, DMSO-$d_6$): δ [ppm] = 0.91-1.01 (m, 6H), 1.01-1.18 (m, 4H), 1.28-1.51 (m, 2H), 1.68-1.97 (m, 3H), 2.05 (t, 1H), 4.62 (br., 1H), 7.19-7.40 (m, 3H), 7.48 (d, 1H), 7.63 (d, 1H), 7.82 (d, H), 7.75-8.19 (very br., 2H), 9.00 (s, 1H), 12.78 (br., 1H). |
| 2-5, (1-1; 947533-31-5) | 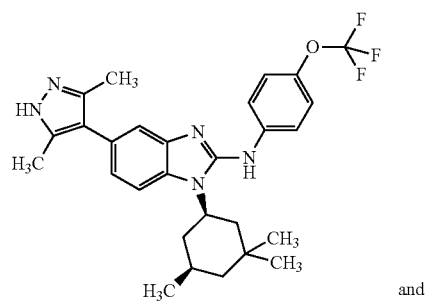 [SMILES: Cc1n[nH]c(C)c1-c1ccc2c(c1)nc(Nc1ccc(OC(F)(F)F)cc1)n2[C@@H]1C[C@H](C)CC(C)(C)C1] and 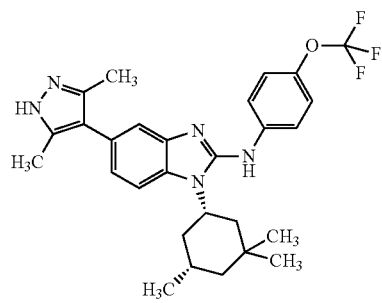<br>(±)5-(3,5-dimethyl-1H-pyrazol-4-yl)-N-[4-(trifluoromethoxy)phenyl]-1-[(cis)-3,3,5-trimethylcyclohexyl]-1H-benzimidazol-2-amine | UPLC-MS: $R_t$ = 1.31 min; m/z = 512.3 (ES+, M + 1).<br>$^1$H-NMR (300 MHz, DMSO-$d_6$): δ [ppm] = 0.90-1.02 (m, 6H), 1.02-1.17 (m, 4H), 1.42 (t, 2H), 1.72-1.95 (m, 3H), 2.00-2.22 (m, 7H), 4.66 (br. s., 1H), 6.92 (dd, 1H), 7.19-7.37 (m, 3H), 7.54 (d, 1H), 7.81 (d, 2H), 9.03 (s, 1H), 12.20 (br., 1H). |

TABLE 1-continued

| Example, (intermediate; boronic acid: CAS-RN) | Structure/Name | Methods/analytical data |
|---|---|---|
| 2-5-1 | 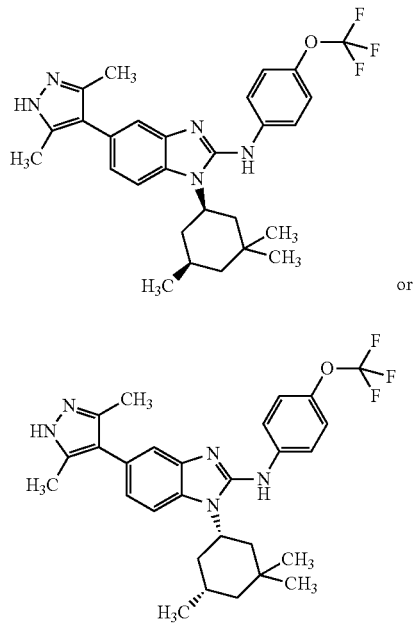<br><br>or<br><br>5-(3,5-dimethyl-1H-pyrazol-4-yl)-N-[4-(trifluoromethoxy)phenyl]-1-[(cis)-3,3,5-trimethylcyclohexyl]-1H-benzimidazol-2-amine, enantiomer A | System: Agilent Prep 1200, 2xPrep Pump, DLA, MWD, Prep FC; column: Chiralpak ID, 5 µM 250 × 20 mm; injection: 45 mg in 3 × 0.5 mL dichloromethane/methanol (1:1); solvent: hexane/2-propanol/diethylamine (70:30:0.1); flow: 20 mL/min; detection: UV 254 nm; $R_t$ = 4.5-5.4 min.<br>$^1$H-NMR (300 MHz, DMSO-$d_6$): δ [ppm] = 0.87-1.02 (m, 6H), 1.02-1.17 (m, 4H), 1.42 (t, 2H), 1.73-1.97 (m, 3H), 2.01-2.22 (m, 7H), 4.66 (br., 1H), 6.92 (d, 1H), 7.19-7.37 (m, 3H), 7.54 (d, 1H), 7.81 (d, 2H), 9.02 (s, 1H), 12.16 (br. s., 1H). |
| 2-5-2 | 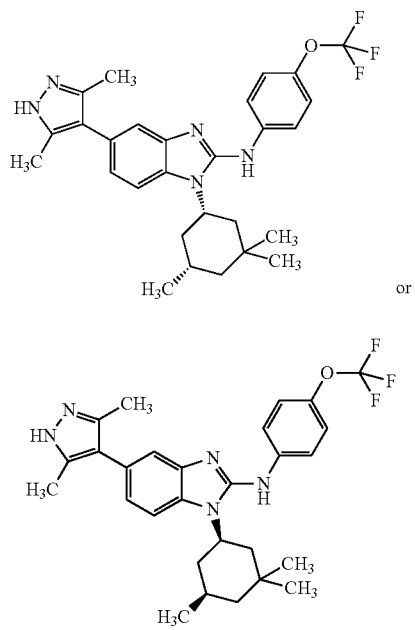<br><br>or<br><br>5-(3,5-dimethyl-1H-pyrazol-4-yl)-N-[4-(trifluoromethoxy)phenyl]-1-[(cis)-3,3,5-trimethylcyclohexyl]-1H-benzimidazol-2-amine, enantiomer B | System: Agilent Prep 1200, 2xPrep Pump, DLA, MWD, Prep FC; column: Chiralpak ID, 5 µM 250 × 20 mm; injection: 45 mg in 3 × 0.5 mL dichloromethane/methanol (1:1); solvent: hexane/2-propanol/diethylamine (70:30:0.1); flow: 20 mL/min; detection: UV 254 nm; $R_t$ = 7.4-8.6 min.<br>$^1$H-NMR (400 MHz, DMSO-$d_6$): δ [ppm] = 0.90-1.02 (m, 6H), 1.02-1.20 (m, 4H), 1.33-1.51 (m, 2H), 1.73-1.94 (m, 3H), 2.01-2.13 (m, 1H), 2.18 (s, 6H), 4.66 (br., 1H), 6.92 (dd, 1H), 7.24 (d, 1H), 7.31 (d, 2H), 7.54 (d, 1H), 7.76-7.85 (m, 2H), 9.00 (s, 1H), 12.15 (br. s., 1H). |

TABLE 1-continued

| Example, (intermediate; boronic acid: CAS-RN) | Structure/Name | Methods/analytical data |
|---|---|---|
| 2-7 (1-1; 1009071-34-4) | 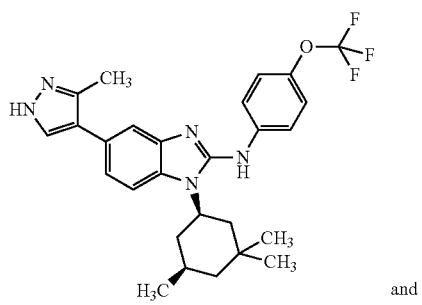 [SMILES: Cc1n[nH]cc1-c1ccc2c(c1)nc(Nc1ccc(OC(F)(F)F)cc1)n2[C@@H]1C[C@H](C)CC(C)(C)C1] and 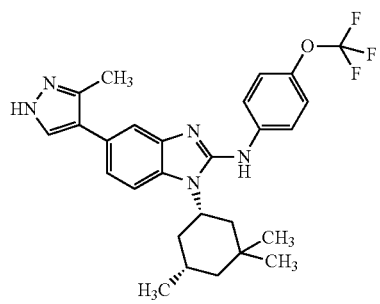<br>(±)5-(3-methyl-1H-pyrazol-4-yl)-N-[4-(trifluoromethoxy)phenyl]-1-[(cis)-3,3,5-trimethylcyclohexyl]-1H-benzimidazol-2-amine | UPLC-MS (method B): $R_t$ = 1.55 min; m/z = 498.2 (ES+, M + 1). $^1$H-NMR (400 MHz, DMSO-$d_6$): δ [ppm] = 0.86-1.01 (m, 6H), 1.01-1.20 (m, 4H), 1.41 (t, 2H), 1.69-1.96 (m, 3H), 1.97-2.14 (m, 1H), 2.33 (br., 3H), 4.65 (t, 1H), 7.08 (d, 1H), 7.31 (d, 2H), 7.41 (s, 1H), 7.48-7.70 (m, 2H), 7.81 (d, 2H), 9.01 (s, 1H), 12.52 (br., 1H). |
| 2-8 (1-1; 1217500-54-3) | 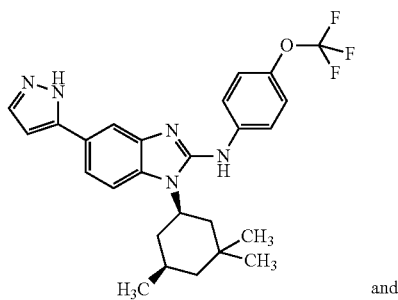 [SMILES: C[C@H]1C[C@@H](n2c(Nc3ccc(OC(F)(F)F)cc3)nc3cc(-c4ccn[nH]4)ccc32)CC(C)(C)C1] and 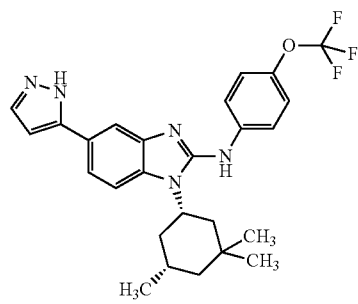<br>(±)5-(1H-pyrazol-5-yl)-N-[4-(trifluoromethoxy)phenyl]-1-[(cis)-3,3,5-trimethylcyclohexyl]-1H-benzimidazol-2-amine | UPLC-MS $R_t$ = 1.32 min; m/z = 484.2 (ES+, M + 1). $^1$H-NMR (400 MHz, DMSO-$d_6$): δ [ppm] = 0.93-1.02 (m, 6H), 1.02-1.16 (m, 4H), 1.32-1.50 (m, 2H), 1.68-1.97 (m, 3H), 2.08 (t, 1H), 4.66 (t, 1H), 6.65 (s, 1H), 7.25-7.38 (m, 2H), 7.45-7.72 (m, 3H), 7.72-7.89 (m, 3H), 9.05 (s, 1H), 12.70 (br., 1H). |

TABLE 1-continued

| Example, (intermediate; boronic acid: CAS-RN) | Structure/Name | Methods/analytical data |
|---|---|---|
| 2-9 (1-1; 1008139-25-0) | 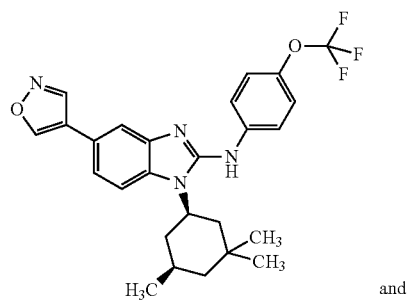 [SMILES: C[C@H]1C[C@@H](n2c(Nc3ccc(OC(F)(F)F)cc3)nc3cc(-c4cnoc4)ccc32)CC(C)(C)C1]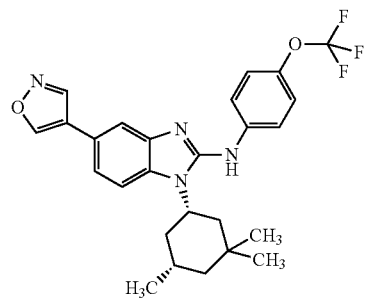 and (±)5-(1,2-oxazol-4-yl)-N-[4-(trifluoromethoxy)phenyl]-1-[(cis)-3,3,5-trimethylcyclohexyl]-1H-benzimidazol-2-amine | UPLC-MS $R_t$ = 1.43 min; m/z = 485.2 (ES+, M + 1). $^1$H-NMR (400 MHz, DMSO-$d_6$): δ [ppm] = 0.91-1.01 (m, 6H), 1.01-1.18 (m, 4H), 1.32-1.49 (m, 2H), 1.69-1.96 (m, 3H), 2.05 (t, 1H), 4.66 (t, 1H), 7.29-7.40 (m, 3H), 7.57 (d, 1H), 7.73-7.91 (m, 3H), 9.08 (s, 1H), 9.14 (s, 1H), 9.36 (s, 1H). |
| 2-10 (1-2; 947533-31-5) | 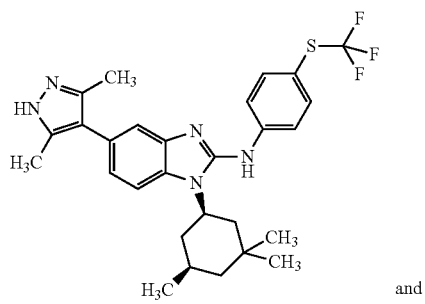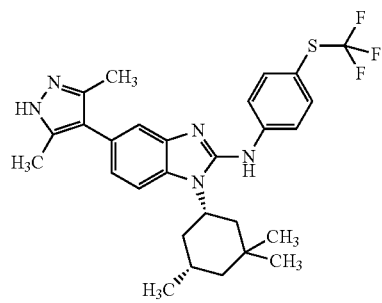 and (±)5-(3,5-dimethyl-1H-pyrazol-4-yl)-N-{4-[(trifluoromethyl)sulfanyl]phenyl}-1-[(cis)-3,3,5-trimethylcyclohexyl]-1H-benzimidazol-2-amine | UPLC-MS (method B): $R_t$ = 1.66 min; m/z = 528.2 (ES+, M + 1). $^1$H-NMR (400 MHz, DMSO-$d_6$): δ [ppm] = 0.92-1.01 (m, 6H), 1.01-1.28 (m, 4H), 1.34-1.52 (m, 2H), 1.72-1.96 (m, 3H), 2.09 (t, 1H), 2.20 (br., s, 6H), 4.67 (t, 1H), 6.96 (dd, 1H), 7.29 (d, 1H), 7.51-7.69 (m, 3H), 7.76-7.94 (m, 2H), 9.25 (s, 1H), 12.19 (br., 1H). |

TABLE 1-continued

| Example, (intermediate; boronic acid: CAS-RN) | Structure/Name | Methods/analytical data |
|---|---|---|
| 2-10-1 | 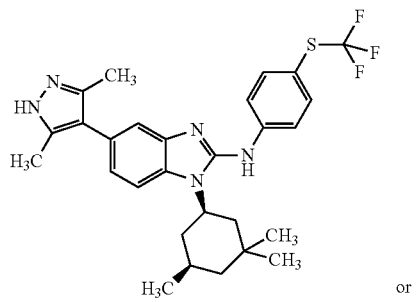 [SMILES: Cc1n[nH]c(C)c1-c1ccc2c(c1)nc(Nc1ccc(SC(F)(F)F)cc1)n2[C@@H]1C[C@H](C)CC(C)(C)C1] or 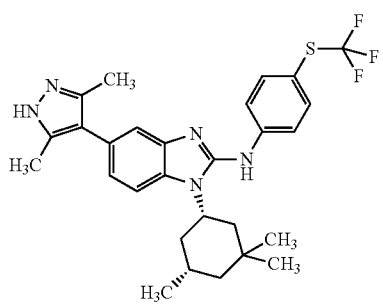<br>5-(3,5-dimethyl-1H-pyrazol-4-yl)-N-{4-[(trifluoromethyl)sulfanyl]phenyl}-1-[(cis)-3,3,5-trimethylcyclohexyl]-1H-benzimidazol-2-amine, enantiomer A | System: Agilent Prep 1200, 2xPrep Pump, DLA, MWD, Prep FC; column: Chiralpak IA, 5 μM 250 × 20 mm; injection: 22 mg in 2 × 0.5 mL dichloromethane/methanol (1:1); solvent: hexane/ethanol/diethylamine (70:30:0.1); flow: 20 mL/min; detection: UV 254 nm; $R_t$ = 2-2.98 min.<br>$^1$H-NMR (300 MHz, DMSO-$d_6$): δ [ppm] = 0.91-1.31 (m, 10H), 1.33-1.53 (m, 2H), 1.72-1.94 (m, 3H), 2.07 (t, 1H), 2.18 (s, 6H), 4.67 (t, 1H), 6.95 (dd, 1H), 7.29 (d, 1H), 7.51-7.71 (m, 3H), 7.83 (d, 2H), 9.26 (s, 1H), 12.19 (br. s., 1H). |
| 2-10-2 | 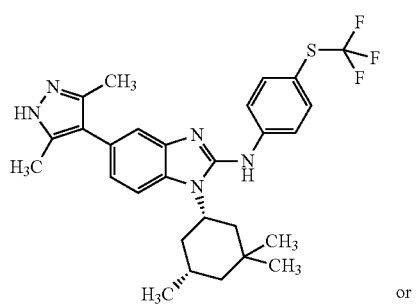 [SMILES: Cc1n[nH]c(C)c1-c1ccc2c(c1)nc(Nc1ccc(SC(F)(F)F)cc1)n2[C@H]1C[C@@H](C)CC(C)(C)C1] or 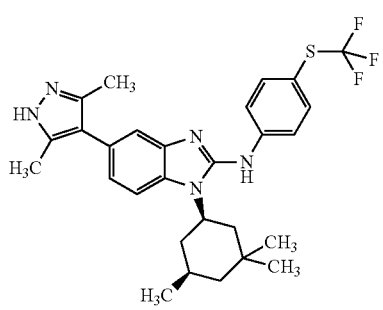<br>5-(3,5-dimethyl-1H-pyrazol-4-yl)-N-{4-[(trifluoromethyl)sulfanyl]phenyl}-1-[(cis)-3,3,5-trimethylcyclohexyl]-1H-benzimidazol-2-amine, enantiomer B | System: Agilent Prep 1200, 2xPrep Pump, DLA, MWD, Prep FC; column: Chiralpak IA, 5 μM 250 × 20 mm; injection: 22 mg in 2 × 0.5 mL dichloromethane/methanol (1:1); solvent: hexane/ethanol/diethylamine (70:30:0.1); flow: 20 mL/min; detection: UV 254 nm; $R_t$ = 5-5.73 min.<br>$^1$H-NMR (300 MHz, DMSO-$d_6$): δ [ppm] = 0.88-1.27 (m, 10H), 1.33-1.52 (m, 2H), 1.73-1.97 (m, 3H), 1.99-2.15 (m, 2H), 2.18 (s, 6H), 2.26 (d, 1H), 4.67 (br., 1H), 6.95 (dd, 1H), 7.29 (d, 1H), 7.53-7.70 (m, 3H), 7.83 (d, 2H), 9.26 (s, 1H), 12.19 (br. s., 1H). |

TABLE 1-continued

| Example, (intermediate; boronic acid: CAS-RN) | Structure/Name | Methods/analytical data |
|---|---|---|
| 2-11 (1-1; 351422-73-6) | 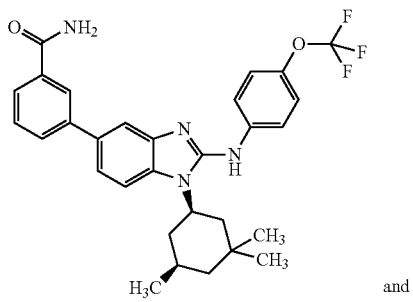 [SMILES: C[C@H]1C[C@@H](n2c(Nc3ccc(OC(F)(F)F)cc3)nc3cc(-c4cccc(C(N)=O)c4)ccc32)CC(C)(C)C1] and 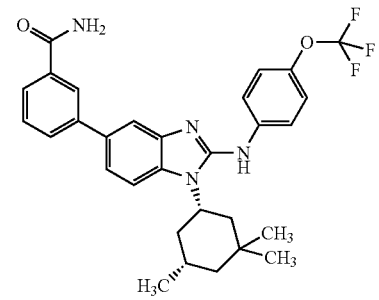<br>(±)3-(2-{[4-(trifluoromethoxy)phenyl]amino}-1-[(cis)-3,3,5-trimethylcyclohexyl]-1H-benzimidazol-5-yl)benzamide | UPLC-MS: $R_t$ = 1.29 min; m/z = 537.2 (ES+, M + 1). $^1$H-NMR (300 MHz, DMSO-$d_6$): δ [ppm] = 0.86-1.02 (m, 6H), 1.02-1.22 (m, 4H), 1.33-1.50 (m, 2H), 1.70-1.95 (m, 3H), 2.08 (t, 1H), 4.69 (br. s., 1H), 7.26-7.45 (m, 4H), 7.45-7.58 (m, 1H), 7.63 (d, 1H), 7.73-7.91 (m, 5H), 8.04-8.23 (m, 2H), 9.11 (s, 1H). |
| 2-12 (1-1; 847818-68-2) | 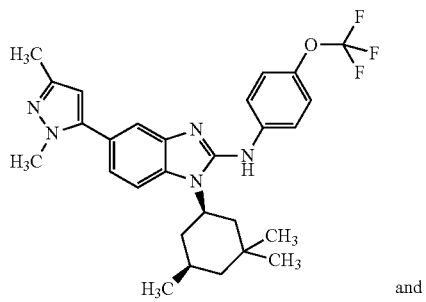 [SMILES: Cc1cc(-c2ccc3c(c2)nc(Nc2ccc(OC(F)(F)F)cc2)n3[C@@H]2C[C@H](C)CC(C)(C)C2)n(C)n1] and 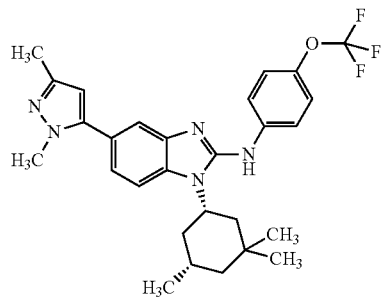<br>(±)-5-(1,3-dimethyl-1H-pyrazol-5-yl)-N-[4-(trifluoromethoxy)phenyl]-1-[(cis)-3,3,5-trimethylcyclohexyl]-1H-benzimidazol-2-amine | UPLC-MS: $R_t$ = 1.48 min; m/z = 512.3 (ES+, M + 1). $^1$H-NMR (300 MHz, DMSO-$d_6$): δ [ppm] = 0.97-0.99 (m, 6H), 1.06-1.15 (m, 4H), 1.43 (t, 2H), 1.73-1.91 (m, 3H), 2.08 (t, 1H), 2.16 (s, 3H), 3.76 (s, 3H), 4.65-4.74 (m, 1H), 6.11 (s, 1H), 7.11 (dd, 1H), 7.32-7.35 (m, 2H), 7.47 (d, 1H), 7.64 (d, 1H), 7.81-7.86 (m, 2H), 9.13 (s, 1H). |

TABLE 1-continued

| Example, (intermediate; boronic acid: CAS-RN) | Structure/Name | Methods/analytical data |
|---|---|---|
| 2-12-1 | 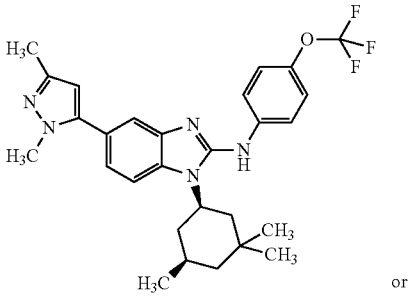 [SMILES: Cc1cc(-c2ccc3c(c2)nc(Nc2ccc(OC(F)(F)F)cc2)n3[C@@H]2C[C@H](C)CC(C)(C)C2)n(C)n1]   5-(1,3-dimethyl-1H-pyrazol-5-yl)-N-[4-(trifluoromethoxy)phenyl]-1-[(cis)-3,3,5-trimethylcyclohexyl]-1H-benzimidazol-2-amine, enantiomer A | System: Agilent: Prep 1200, 2xPrep Pump, DLA, MWD, Gilson: Liquid Handler 215; column: Chiralpak ID 5 μM 250 × 30 mm; solvent: hexane/2-propanol/diethylamine (70:30:0.1); flow: 50 mL/min; temperature: RT; solution: 32 mg/1.6 mL DCM/MeOH; injection: 2 × 0.8 mL; detection: UV 254 nm; $R_t$ = 11.5-13.5 min. |
| 2-12-2 | 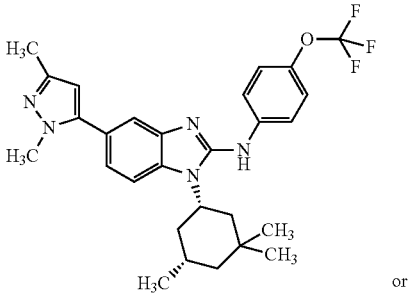 [SMILES: Cc1cc(-c2ccc3c(c2)nc(Nc2ccc(OC(F)(F)F)cc2)n3[C@H]2C[C@@H](C)CC(C)(C)C2)n(C)n1]   5-(1,3-dimethyl-1H-pyrazol-5-yl)-N-[4-(trifluoromethoxy)phenyl]-1-[(cis)-3,3,5-trimethylcyclohexyl]-1H-benzimidazol-2-amine, enantiomer B | System: Agilent: Prep 1200, 2xPrep Pump, DLA, MWD, Gilson: Liquid Handler 215; column: Chiralpak ID 5 μM 250 × 30 mm; solvent: hexane/2-propanol/diethylamine (70:30:0.1); flow: 50 mL/min; temperature: RT; solution: 32 mg/1.6 mL DCM/MeOH; injection: 2 × 0.8 mL; detection: UV 254 nm; $R_t$ = 23.4-27.2 min. |

TABLE 1-continued

| Example, (intermediate; boronic acid: CAS-RN) | Structure/Name | Methods/analytical data |
|---|---|---|
| 2-13 (1-1; 847818-55-7) | 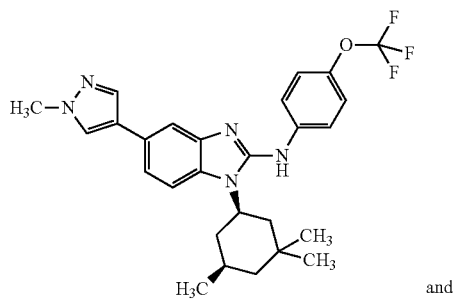 [SMILES: C[C@H]1C[C@@H](n2c(Nc3ccc(OC(F)(F)F)cc3)nc3cc(-c4cnn(C)c4)ccc32)CC(C)(C)C1] and 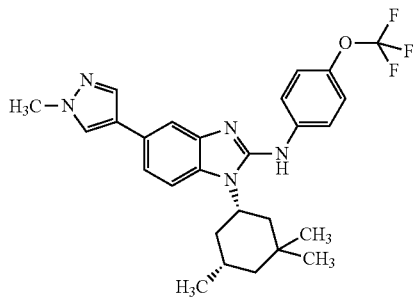<br>(±)-5-(1-methyl-1H-pyrazol-4-yl)-N-[4-(trifluoromethoxy)phenyl]-1-[(cis)-3,3,5-trimethylcyclohexyl]-1H-benzimidazol-2-amine | UPLC-MS: $R_t$ = 1.28 min; m/z = 498.2 (ES+, M + 1). $^1$H-NMR (400 MHz, DMSO-$d_6$): δ [ppm] = 0.90-1.16 (m, 10H), 1.33-1.49 (m, 2H), 1.67-1.96 (m, 3H), 2.04 (t, 1H), 3.85 (s, 3H), 4.63 (t, 1H), 7.20 (dd, 1H), 7.31 (d, 2H), 7.48 (d, 1H), 7.58 (d, 1H), 7.73-7.89 (m, 3H), 8.03 (s, 1H), 9.01 (s, 1H). |
| 2-13-1 | 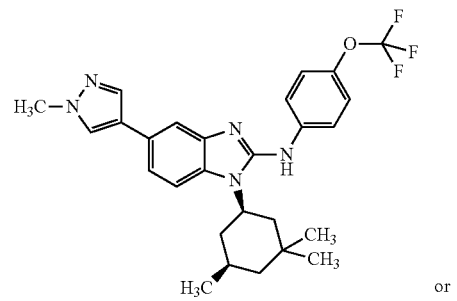 [SMILES: C[C@H]1C[C@@H](n2c(Nc3ccc(OC(F)(F)F)cc3)nc3cc(-c4cnn(C)c4)ccc32)CC(C)(C)C1] or 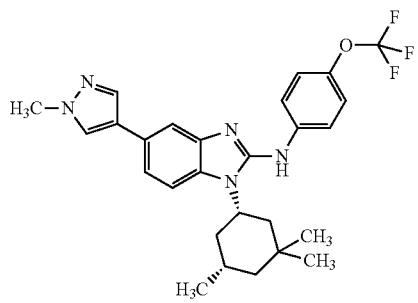<br>5-(1-methyl-1H-pyrazol-4-yl)-N-[4-(trifluoromethoxy)phenyl]-1-[(cis)-3,3,5-trimethylcyclohexyl]-1H-benzimidazol-2-amine, enantiomer A | System: Agilent Prep 1200, 2xPrep Pump, DLA, MWD, Prep FC; column: Chiralpak ID, 5 μM 250 × 30 mm; injection: 50 mg in 2 × 1 mL dichloromethane; solvent: hexane/ethanol/diethylamine (70:30:0.1); flow: 50 mL/min; detection: UV 254 nm; $R_t$ = 7.3-8.5 min. $^1$H-NMR (300 MHz, DMSO-$d_6$): δ [ppm] = 0.90-1.17 (m, 10H), 1.32-1.48 (m, 2H), 1.69-1.96 (m, 3H), 2.04 (t, 1H), 3.85 (s, 3H), 4.64 (br., 1H), 7.20 (dd, 1H), 7.31 (d, 2H), 7.49 (d, 1H), 7.58 (d, 1H), 7.75-7.88 (m, 3H), 8.04 (s, 1H), 9.02 (s, 1H). |

TABLE 1-continued

| Example, (intermediate; boronic acid: CAS-RN) | Structure/Name | Methods/analytical data |
|---|---|---|
| 2-13-2 | 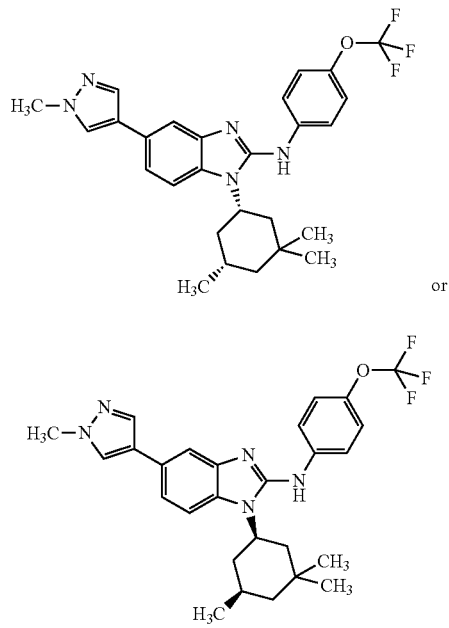<br>5-(1-methyl-1H-pyrazol-4-yl)-N-[4-(trifluoromethoxy)phenyl]-1-[(cis)-3,3,5-trimethylcyclohexyl]-1H-benzimidazol-2-amine, enantiomer B | System: Agilent Prep 1200, 2xPrep Pump, DLA, MWD, Prep FC; column: Chiralpak ID, 5 μM 250 × 30 mm; injection: 50 mg in 2 × 1 mL dichloromethane; solvent: hexane/ethanol/diethylamine (70:30:0.1); flow: 50 mL/min; detection: UV 254 nm; $R_t$ = 8.7-10.9 min.<br>$^1$H-NMR (300 MHz, DMSO-$d_6$): δ [ppm] = 0.89-1.18 (m, 10H), 1.31-1.48 (m, 2H), 1.69-1.97 (m, 3H), 2.04 (t, 1H), 3.85 (s, 3H), 4.55-4.71 (m, 1H), 7.20 (dd, 1H), 7.31 (d, 2H), 7.49 (d, 1H), 7.55-7.61 (m, 1H), 7.75-7.88 (m, 3H), 8.04 (s, 1H), 9.02 (s, 1H). |
| 2-14 (1-1; 762262-09-9) | 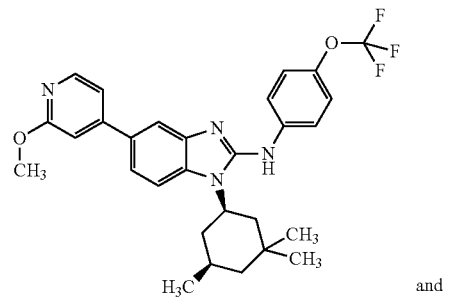 [SMILES: COc1cc(-c2ccc3c(c2)nc(Nc2ccc(OC(F)(F)F)cc2)n3[C@@H]2C[C@H](C)CC(C)(C)C2)ccn1] and<br>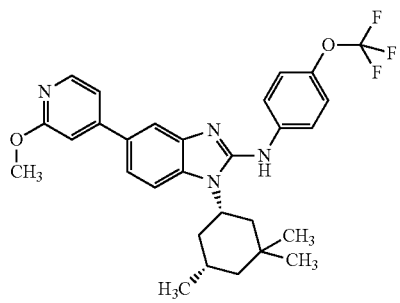<br>(±)5-(2-methoxypyridin-4-yl)-N-[4-(trifluoromethoxy)phenyl]-1-[(cis)-3,3,5-trimethylcyclohexyl]-1H-benzimidazol-2-amine | UPLC-MS: $R_t$ = 1.58 min; m/z = 525.2 (ES+, M + 1).<br>$^1$H-NMR (400 MHz, DMSO-$d_6$): δ [ppm] = 0.93-1.02 (m, 6H), 1.02-1.22 (m, 4H), 1.42 (t, 2H), 1.70-1.97 (m, 3H), 2.09 (t, 1H), 3.88 (s, 3H), 4.68 (t, 1H), 7.08 (s, 1H), 7.23-7.38 (m, 3H), 7.42 (dd, 1H), 7.64 (d, 1H), 7.77-7.88 (m, 3H), 8.09-8.22 (m, 1H), 9.11 (s, 1H). |

TABLE 1-continued

| Example, (intermediate; boronic acid: CAS-RN) | Structure/Name | Methods/analytical data |
|---|---|---|
| 2-15 (1-1; 99769-19-4) | 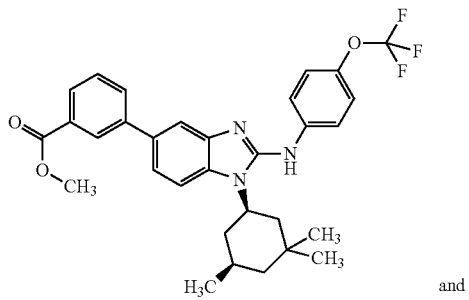 [SMILES: COC(=O)c1cccc(-c2ccc3c(c2)nc(Nc2ccc(OC(F)(F)F)cc2)n3[C@@H]2C[C@H](C)CC(C)(C)C2)c1] and 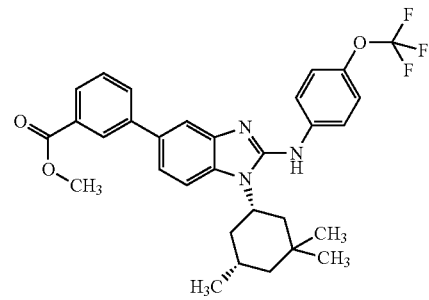<br>(±)methyl 3-(2-{[4-(trifluoromethoxy)phenyl]amino}-1-[(cis)-3,3,5-trimethylcyclohexyl]-1H-benzimidazol-5-yl)benzoate | UPLC-MS: $R_t$ = 1.62 min; m/z = 552.2 (ES+, M + 1). $^1$H-NMR (400 MHz, DMSO-$d_6$): δ [ppm] = 0.90-1.02 (m, 6H), 1.02-1.20 (m, 4H), 1.36-1.51 (m, 2H), 1.72-1.95 (m, 3H), 2.08 (t, 1H), 3.89 (s, 3H), 4.69 (br., 1H), 7.26-7.41 (m, 3H), 7.55-7.71 (m, 3H), 7.80-7.99 (m, 4H), 8.19 (s, 1H), 9.10 (s, 1H). |
| 2-16 (1-1; 1138450-30-2) | 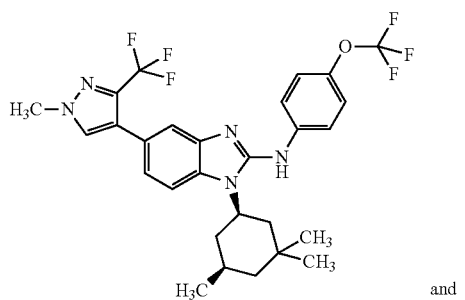 [SMILES: C[C@H]1C[C@@H](n2c(Nc3ccc(OC(F)(F)F)cc3)nc3cc(-c4cn(C)nc4C(F)(F)F)ccc32)CC(C)(C)C1] and 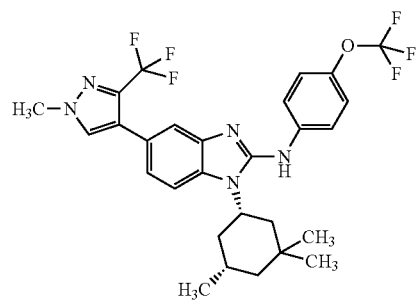<br>(±)5-[1-methyl-3-(trifluoromethyl)-1H-pyrazol-4-yl]-N-[4-(trifluoromethoxy)phenyl]-1-[(cis)-3,3,5-trimethylcyclohexyl]-1H-benzimidazol-2-amine | UPLC-MS: $R_t$ = 1.49 min; m/z = 566.2 (ES+, M + 1). $^1$H-NMR (300 MHz, DMSO-$d_6$): δ [ppm] = 0.89-1.20 (m, 10H), 1.33-1.52 (m, 2H), 1.68-1.93 (m, 3H), 2.07 (t, 1H), 3.95 (s, 3H), 4.67 (br., 1H), 7.00-7.09 (m, 1H), 7.27-7.43 (m, 3H), 7.59 (d, 1H), 7.82 (d, 2H), 8.07 (s, 1H), 9.08 (s, 1H). |

TABLE 1-continued

| Example, (intermediate; boronic acid: CAS-RN) | Structure/Name | Methods/analytical data |
|---|---|---|
| 2-16-1 | 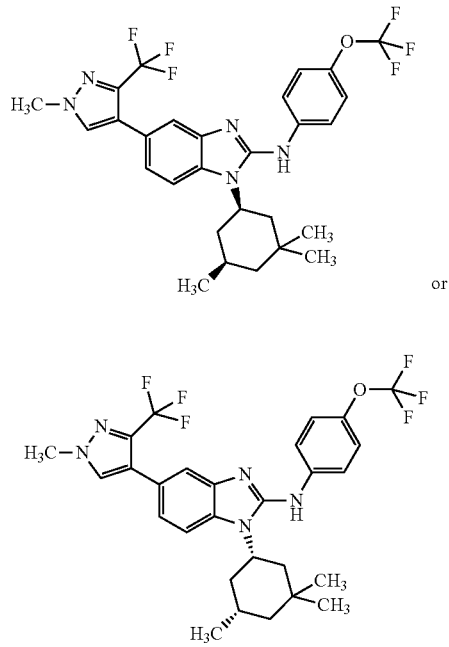

5-[1-methyl-3-(trifluoromethyl)-1H-pyrazol-4-yl]-N-[4-(trifluoromethoxy)phenyl]-1-[(cis)-3,3,5-trimethylcyclohexyl]-1H-benzimidazol-2-amine, enantiomer A | System: Agilent Prep 1200, 2xPrep Pump, DLA, MWD, Prep FC; column: Chiralpak IA, 5 μM 250 × 20 mm; injection: 50 mg in 3 × 0.5 mL dichloromethane/methanol (1:1); solvent: hexane/isopropanol/diethylamine (70:30:0.1); flow: 20 mL/min; detection: UV 254 nm; $R_t$ = 5.7-6.9 min. $^1$H-NMR (400 MHz, DMSO-$d_6$): δ [ppm] = 0.91-1.01 (m, 6H), 1.01-1.16 (m, 4H), 1.32-1.48 (m, 2H), 1.73-1.93 (m, 3H), 2.07 (t, 1H), 3.95 (s, 3H), 4.66 (br., 1H), 7.04 (dd, 1H), 7.32 (d, 2H), 7.38 (d, 1H), 7.59 (d, 1H), 7.78-7.85 (m, 2H), 8.07 (s, 1H), 9.06 (s, 1H). |
| 2-16-2 | 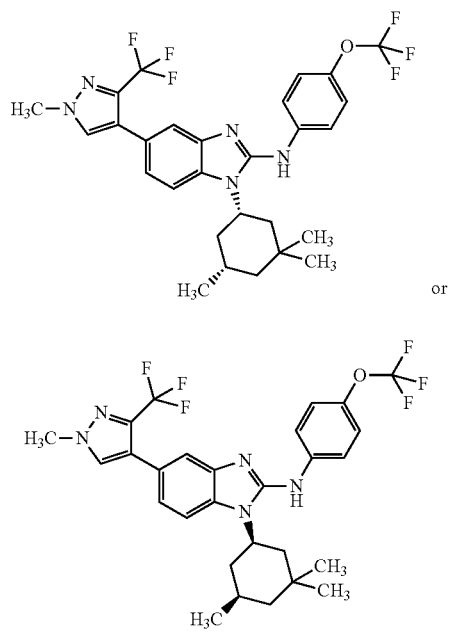

5-[1-methyl-3-(trifluoromethyl)-1H-pyrazol-4-yl]-N-[4-(trifluoromethoxy)phenyl]-1-[(cis)-3,3,5-trimethylcyclohexyl]-1H-benzimidazol-2-amine, enantiomer B | System: Agilent Prep 1200, 2xPrep Pump, DLA, MWD, Prep FC; column: Chiralpak IA, 5 μM 250 × 20 mm; injection: 50 mg in 3 × 0.5 mL dichloromethane/methanol (1:1); solvent: hexane/isopropanol/diethylamine (70:30:0.1); flow: 20 mL/min; detection: UV 254 nm; $R_t$ = 9.7-11.5 min. $^1$H-NMR (400 MHz, DMSO-$d_6$): δ [ppm] = 0.91-1.01 (m, 6H), 1.01-1.17 (m, 4H), 1.35-1.49 (m, 2H), 1.70-1.94 (m, 3H), 2.07 (t, 1H), 3.95 (s, 3H), 4.66 (t, 1H), 7.00-7.08 (m, 1H), 7.32 (d, 2H), 7.36-7.40 (m, 1H), 7.59 (d, 1H), 7.76-7.85 (m, 2H), 8.07 (s, 1H), 9.06 (s, 1H). |

TABLE 1-continued

| Example, (intermediate; boronic acid: CAS-RN) | Structure/Name | Methods/analytical data |
|---|---|---|
| 2-17 (1-1; 123088-59-5) | 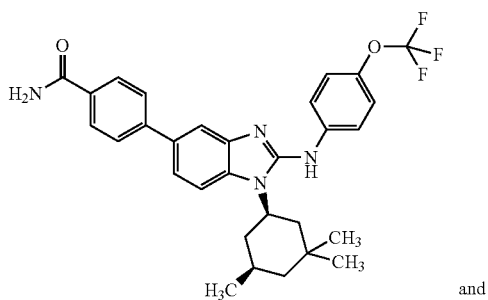 [SMILES: C[C@H]1C[C@@H](n2c(Nc3ccc(OC(F)(F)F)cc3)nc3cc(-c4ccc(C(N)=O)cc4)ccc32)CC(C)(C)C1]<br>(±)4-(2-{[4-(trifluoromethoxy)phenyl]amino}-1-[(cis)-3,3,5-trimethylcyclohexyl]-1H-benzimidazol-5-yl)benzamide | UPLC-MS: $R_t$ = 1.32 min; m/z = 537.2 (ES+, M + 1). $^1$H-NMR (300 MHz, DMSO-$d_6$): δ [ppm] = 0.88-1.19 (m, 10H), 1.32-1.52 (m, 2H), 1.70-1.98 (m, 3H), 2.08 (t, 1H), 4.68 (br., 1H), 7.27-7.43 (m, 4H), 7.63 (d, 1H), 7.70-7.80 (m, 3H), 7.86 (d, 2H), 7.90-8.07 (m, 3H), 9.11 (s, 1H). |
| 2-18 (1-1; 99768-12-4) | 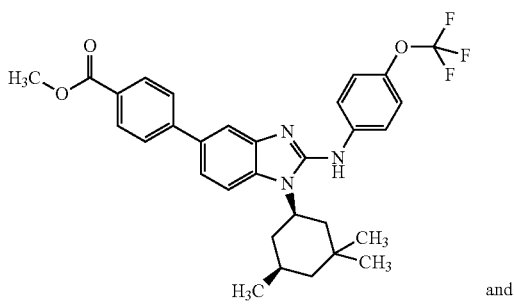 [SMILES: COC(=O)c1ccc(-c2ccc3c(c2)nc(Nc2ccc(OC(F)(F)F)cc2)n3[C@@H]2C[C@H](C)CC(C)(C)C2)cc1]<br>(±)methyl -4-(2-{[4-(trifluoromethoxy)phenyl]amino}-1-[(cis)-3,3,5-trimethylcyclohexyl]-1H-benzimidazol-5-yl)benzoate | UPLC-MS: $R_t$ = 1.60 min; m/z = 552.2 (ES+, M + 1). $^1$H-NMR (400 MHz, DMSO-$d_6$): δ [ppm] = 0.86-1.01 (m, 6H), 1.01-1.22 (m, 4H), 1.33-1.52 (m, 2H), 1.72-1.96 (m, 3H), 2.07 (t, 1H), 3.86 (s, 3H), 4.68 (br., 1H), 7.27-7.43 (m, 3H), 7.64 (d, 1H), 7.70-7.91 (m, 5H), 7.93-8.09 (m, 2H), 9.10 (s, 1H). |

TABLE 1-continued

| Example, (intermediate; boronic acid: CAS-RN) | Structure/Name | Methods/analytical data |
|---|---|---|
| 2-19 (1-1; 847818-62-6) | 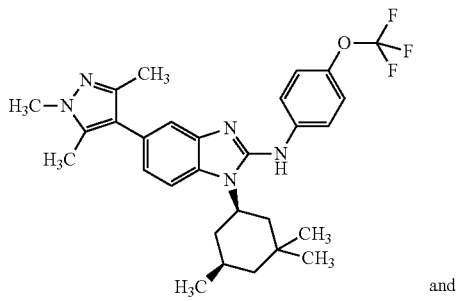 [SMILES: Cc1nn(C)c(C)c1-c1ccc2c(c1)nc(Nc1ccc(OC(F)(F)F)cc1)n2[C@@H]1C[C@H](C)CC(C)(C)C1]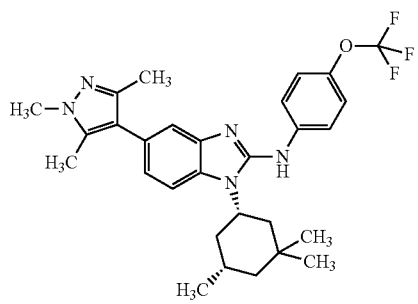 and (±)N-[4-(trifluoromethoxy)phenyl]-1-[(cis)-3,3,5-trimethylcyclohexyl]-5-(1,3,5-trimethyl-1H-pyrazol-4-yl)-1H-benzimidazol-2-amine | UPLC-MS: $R_t$ = 1.31 min; m/z = 526.3 (ES+, M + 1). $^1$H-NMR (400 MHz, DMSO-$d_6$): δ [ppm] = 0.93-1.18 (m, 10H), 1.32-1.50 (m, 2H), 1.70-1.98 (m, 3H), 2.00-2.16 (m, 4H), 2.20 (s, 3H), 3.70 (s, 3H), 4.66 (t, 1H), 6.82-6.93 (m, 1H), 7.21 (d, 1H), 7.28-7.38 (m, 2H), 7.49-7.61 (m, 1H), 7.78-7.88 (m, 2H), 9.02 (s, 1H). |
| 2-20 (1-1; 720702-41-0) | 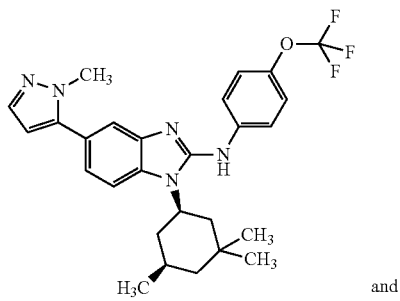 [SMILES: C[C@H]1C[C@@H](n2c(Nc3ccc(OC(F)(F)F)cc3)nc3cc(-c4ccnn4C)ccc32)CC(C)(C)C1]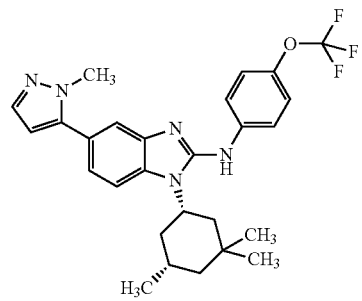 and (±)5-(1-methyl-1H-pyrazol-5-yl)-N-[4-(trifluoromethoxy)phenyl]-1-[(cis)-3,3,5-trimethylcyclohexyl]-1H-benzimidazol-2-amine | UPLC-MS: $R_t$ = 1.44 min; m/z = 498.2 (ES+, M + 1). $^1$H-NMR (300 MHz, DMSO-$d_6$): δ [ppm] = 0.90-1.22 (m, 10H), 1.27-1.51 (m, 2H), 1.72-1.99 (m, 3H), 2.08 (t, 1H), 3.85 (s, 3H), 4.61-4.78 (m, 1H), 7.13 (dd, 1H), 7.33 (d, 2H), 7.45 (d, 1H), 7.52 (d, 1H), 7.64 (d, 1H), 7.83 (d, 2H), 9.12 (s, 1H). |

TABLE 1-continued

| Example, (intermediate; boronic acid: CAS-RN) | Structure/Name | Methods/analytical data |
|---|---|---|
| 2-21 (1-2; 16114-47-9) | 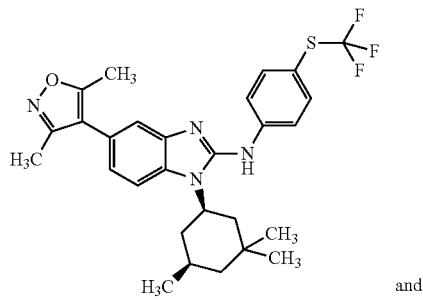 [SMILES: Cc1noc(C)c1-c1ccc2c(c1)nc(Nc1ccc(SC(F)(F)F)cc1)n2[C@@H]1C[C@H](C)CC(C)(C)C1] and 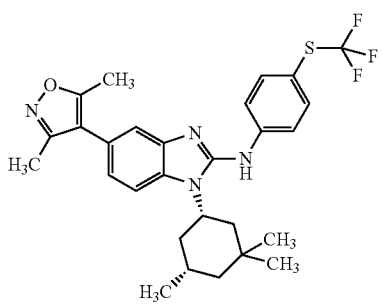<br>(±)5-(3,5-dimethyl-1,2-oxazol-4-yl)-N-{4-[(trifluoromethyl)sulfanyl]phenyl}-1-[(cis)-3,3,5-trimethylcyclohexyl]-1H-benzimidazol-2-amine | UPLC-MS: $R_t$ = 1.68 min; m/z = 529.2 (ES+, M + 1). $^1$H-NMR (400 MHz, DMSO-$d_6$): δ [ppm] = 0.90-1.18 (m, 10H), 1.36-1.51 (m, 2H), 1.70-1.97 (m, 3H), 2.07 (t, 1H), 2.21 (s, 3H), 2.40 (s, 3H), 4.69 (t, 1H), 7.02 (dd, 1H), 7.41 (d, 1H), 7.59-7.71 (m, 3H), 7.85 (d, 2H), 9.30 (s, 1H). |
| 2-21-1 | 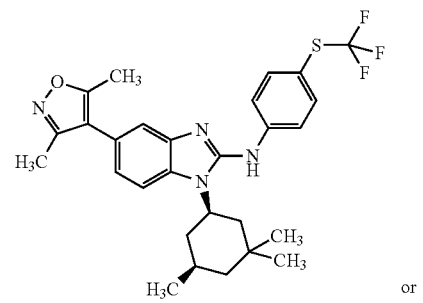 [SMILES: Cc1noc(C)c1-c1ccc2c(c1)nc(Nc1ccc(SC(F)(F)F)cc1)n2[C@@H]1C[C@H](C)CC(C)(C)C1] or 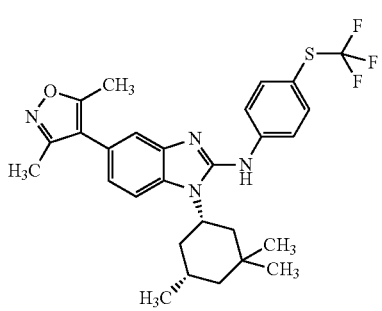<br>5-(3,5-dimethyl-1,2-oxazol-4-yl)-N-{4-[(trifluoromethyl)sulfanyl]phenyl}-1[(cis)-3,3,5-trimethylcyclohexyl]-1H-benzimidazol-2-amine, enantiomer A | System: Agilent Prep 1200, 2xPrep Pump, DLA, MWD, Prep FC; column: Chiralpak IA, 5 μM 250 × 20 mm; injection: 55 mg in 3 × 0.5 mL dichloromethane/methanol (1:1); solvent: hexane/ethanol/diethylamine (70:30:0.1); flow: 20 mL/min; detection: UV 254 nm; $R_t$ = 10.0-11.9 min. $^1$H-NMR (400 MHz, DMSO-$d_6$): δ [ppm] = 0.91-1.01 (m, 6H), 1.01-1.20 (m, 4H), 1.35-1.50 (m, 2H), 1.75-1.94 (m, 3H), 2.07 (t, 1H), 2.22 (s, 3H), 2.39 (s, 3H), 4.69 (br., 1H), 7.02 (dd, 1H), 7.41 (d, 1H), 7.60-7.70 (m, 3H), 7.85 (d, 2H), 9.30 (s, 1H). |

| Example, (intermediate; boronic acid: CAS-RN) | Structure/Name | Methods/analytical data |
|---|---|---|
| 2-21-2 | 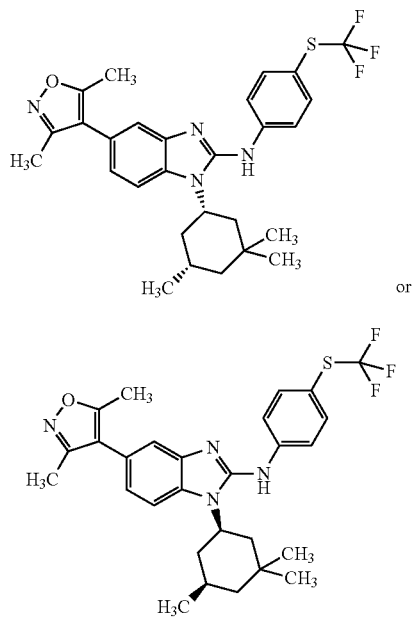<br>5-(3,5-dimethyl-1,2-oxazol-4-yl)-N-{4-[(trifluoromethyl)sulfanyl]phenyl}-1-[(cis)-3,3,5-trimethylcyclohexyl]-1H-benzimidazol-2-amine, enantiomer B | System: Agilent Prep 1200, 2xPrep Pump, DLA, MWD, Prep FC; column: Chiralpak IA, 5 μM 250 × 20 mm; injection: 55 mg in 3 × 0.5 mL dichloromethane/methanol (1:1); solvent: hexane/ethanol/diethylamine (70:30:0.1); flow: 20 mL/min; detection: UV 254 nm; $R_t$ = 25.4-28.4 min.<br>$^1$H-NMR (400 MHz, DMSO-$d_6$): δ [ppm] = 0.90-1.20 (m, 10H), 1.34-1.53 (m, 2H), 1.75-1.94 (m, 3H), 2.00-2.13 (m, 1H), 2.22 (s, 3H), 2.39 (s, 3H), 4.69 (br., 1H), 7.02 (dd, 1H), 7.41 (d, 1H), 7.60-7.70 (m, 3H), 7.85 (d, 2H), 9.31 (s, 1H). |
| 2-22<br>(1-2;<br>1217500-54-3) | 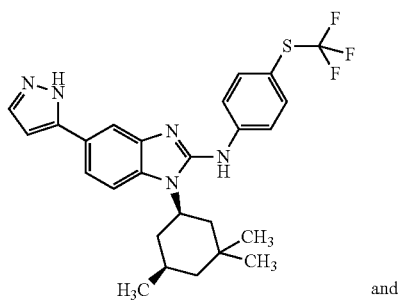 and 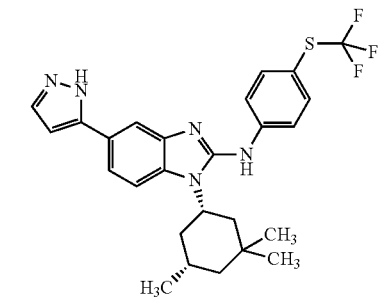<br>(±)5-(1H-pyrazol-5-yl)-N-{4-[(trifluoromethyl)sulfanyl]phenyl}-1-[(cis)-3,3,5-trimethylcyclohexyl]-1H-benzimidazol-2-amine | UPLC-MS (method B): $R_t$ = 1.63 min; m/z = 500.2 (ES+, M + 1).<br>$^1$H-NMR (400 MHz, DMSO-$d_6$): δ [ppm] = 0.89-1.20 (m, 10H), 1.36-1.52 (m, 2H), 1.70-1.97 (m, 3H), 2.06 (t, 1H), 4.66 (br., 1H), 6.61-6.73 (m, 1H), 7.48-7.73 (m, 5H), 7.78-7.92 (m, 3H), 9.28 (s, 1H), 12.7 (very br., 1H). |

| Example, (intermediate; boronic acid: CAS-RN) | Structure/Name | Methods/analytical data |
|---|---|---|
| 2-23 (1-3; 16114-47-9) | 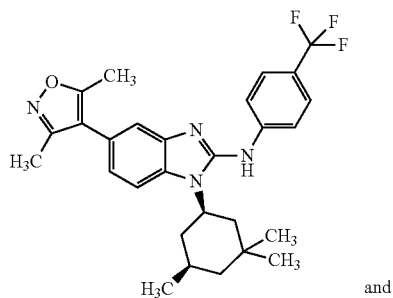 [SMILES: Cc1noc(C)c1-c1ccc2c(c1)nc(Nc1ccc(C(F)(F)F)cc1)n2[C@@H]1C[C@H](C)CC(C)(C)C1]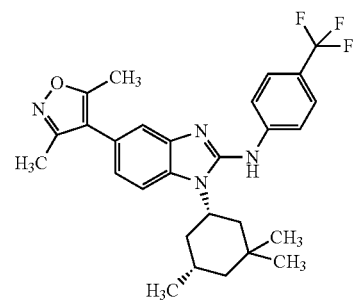<br>(±)5-(3,5-dimethyl-1,2-oxazol-4-yl)-N-[4-(trifluoromethyl)phenyl]-1-[(cis)-3,3,5-trimethylcyclohexyl]-1H-benzimidazol-2-amine | UPLC-MS: $R_t$ = 1.59 min; m/z = 497.2 (ES+, M + 1). $^1$H-NMR (400 MHz, DMSO-$d_6$): δ [ppm] = 0.93-1.17 (m, 10H), 1.29-1.52 (m, 2H), 1.73-1.96 (m, 3H), 2.08 (t, 1H), 2.22 (s, 3H), 2.39 (s, 3H), 4.71 (t, 1H), 7.02 (dd, 1H), 7.42 (d, 1H), 7.60-7.72 (m, 3H), 7.92 (d, 2H), 9.32 (s, 1H). |
| 2-23-1 | 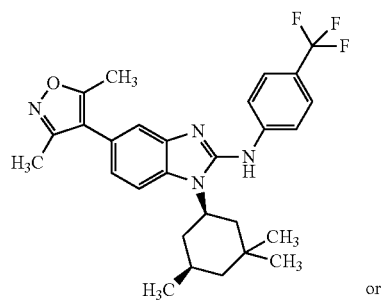 [SMILES: Cc1noc(C)c1-c1ccc2c(c1)nc(Nc1ccc(C(F)(F)F)cc1)n2[C@@H]1C[C@H](C)CC(C)(C)C1]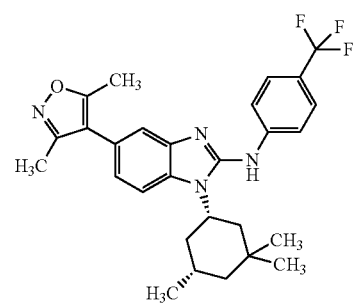<br>5-(3,5-dimethyl-1,2-oxazol-4-yl)-N-[4-(trifluoromethyl)phenyl]-1-[(cis)-3,3,5-trimethylcyclohexyl]-1H-benzimidazol-2-amine, enantiomer A | System: Agilent Prep 1200, 2xPrep Pump, DLA, MWD, Prep FC; column: Chiralpak IA, 5 μM 250 × 20 mm; injection: 65 mg in 3 × 0.5 mL dichloromethane/methanol (1:1); solvent: hexane/ethanol/diethylamine (70:30:0.1); flow: 20 mL/min; detection: UV 254 nm; $R_t$ = 10.1-12.5 min. $^1$H-NMR (400 MHz, DMSO-$d_6$): δ [ppm] = 0.93-1.02 (m, 6H), 1.02-1.15 (m, 4H), 1.35-1.51 (m, 2H), 1.75-1.95 (m, 3H), 2.08 (t, 1H), 2.22 (s, 3H), 2.39 (s, 3H), 4.71 (br., 1H), 7.02 (dd, 1H), 7.42 (d, 1H), 7.66 (dd, 3H), 7.92 (d, 2H), 9.32 (s, 1H). |

TABLE 1-continued

| Example, (intermediate; boronic acid: CAS-RN) | Structure/Name | Methods/analytical data |
|---|---|---|
| 2-23-2 | 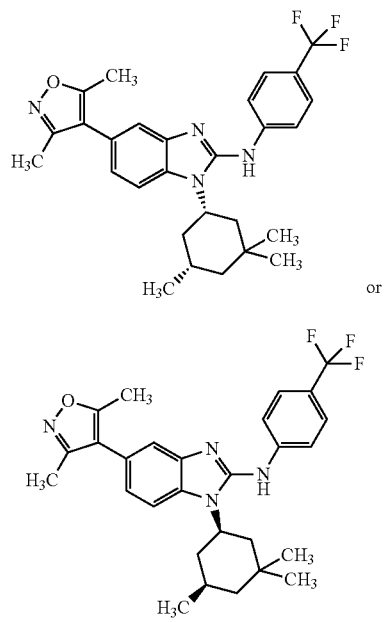<br>5-(3,5-dimethyl-1,2-oxazol-4-yl)-N-[4-(trifluoromethyl)phenyl]-1-[(cis)-3,3,5-trimethylcyclohexyl]-1H-benzimidazol-2-amine, enantiomer B | System: Agilent Prep 1200, 2×Prep Pump, DLA, MWD, Prep FC; column: Chiralpak IA, 5 μM 250 × 20 mm; injection: 65 mg in 3 × 0.5 mL dichloromethane/methanol (1:1); solvent: hexane/ethanol/diethylamine (70:30:0.1); flow: 20 mL/min; detection: UV 254 nm; $R_t$ = 21.4-26.4 min.<br>$^1$H-NMR (400 MHz, DMSO-$d_6$): δ [ppm] = 0.90-1.02 (m, 6H), 1.02-1.16 (m, 4H), 1.35-1.51 (m, 2H), 1.73-1.94 (m, 3H), 2.08 (t, 1H), 2.22 (s, 3H), 2.39 (s, 3H), 4.71 (t, 1H), 7.02 (dd, 1H), 7.42 (d, 1H), 7.66 (dd, 3H), 7.92 (d, 2H), 9.32 (s, 1H). |
| 2-24 (1-3; 947533-31-5) | 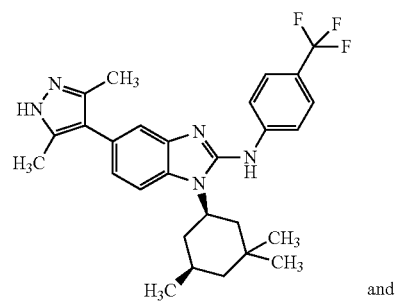 [SMILES: Cc1n[nH]c(C)c1-c1ccc2c(c1)nc(Nc1ccc(C(F)(F)F)cc1)n2[C@@H]1C[C@H](C)CC(C)(C)C1] and 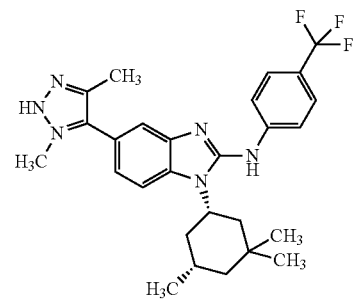<br>(±)5-(3,5-dimethyl-1H-pyrazol-4-yl)-N-[4-(trifluoromethyl)phenyl]-1-[(cis)-3,3,5-trimethylcyclohexyl]-1H-benzimidazol-2-amine | UPLC-MS (method B): $R_t$ = 1.55 min; m/z = 496.3 (ES+, M + 1).<br>$^1$H-NMR (400 MHz, DMSO-$d_6$): δ [ppm] = 0.87-1.20 (m, 10H), 1.32-1.52 (m, 2H), 1.71-1.98 (m, 3H), 2.08 (t, 1H), 2.19 (br., 6H), 4.68 (t, 1H), 6.95 (dd, 1H), 7.29 (d, 1H), 7.52-7.72 (m, 3H), 7.85-7.95 (m, 2H), 9.26 (s, 1H), 12.18 (s, 1H). |

TABLE 1-continued

| Example, (intermediate; boronic acid: CAS-RN) | Structure/Name | Methods/analytical data |
|---|---|---|
| 2-24-1 | 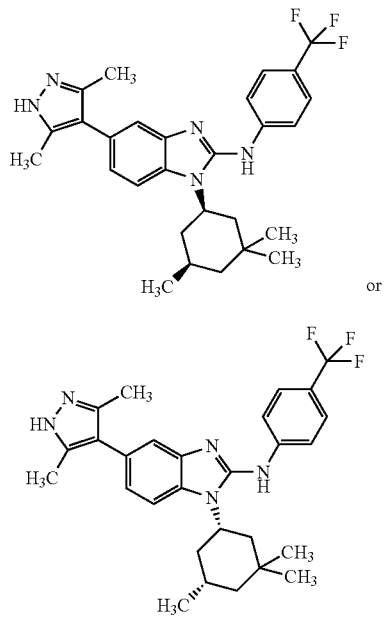 or <br><br>5-(3,5-dimethyl-1H-pyrazol-4-yl)-N-[4-(trifluoromethyl)phenyl]-1-[(cis)-3,3,5-trimethylcyclohexyl]-1H-benzimidazol-2-amine, enantiomer A | System: Agilent Prep 1200, 2xPrep Pump, DLA, MWD, Prep FC; column: Chiralpak IA, 5 µM 250 × 20 mm; injection: 33 mg in 2 × 0.5 mL dichloromethane/methanol (1:1); solvent: hexane/ethanol/diethylamine (70:30:0.1); flow: 20 mL/min; detection: UV 254 nm; $R_t$ = 7.0-8.1 min. <br>$^1$H-NMR (300 MHz, DMSO-$d_6$): δ [ppm] = 0.89-1.18 (m, 10H), 1.33-1.52 (m, 2H), 1.74-1.98 (m, 3H), 2.08 (t, 1H), 2.18 (br., 6H), 4.68 (br., 1H), 6.95 (dd, 1H), 7.28 (d, 1H), 7.52-7.70 (m, 3H), 7.89 (d, 2H), 9.28 (very br., 1H), 12.19 (very br., 1H). |
| 2-24-2 | 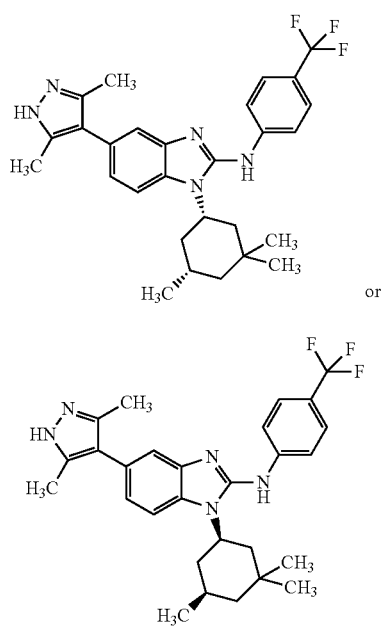 or <br><br>5-(3,5-dimethyl-1H-pyrazol-4-yl)-N-[4-(trifluoromethyl)phenyl]-1-[(cis)-3,3,5-trimethylcyclohexyl]-1H-benzimidazol-2-amine, enantiomer B | System: Agilent Prep 1200, 2xPrep Pump, DLA, MWD, Prep FC; column: Chiralpak IA, 5 µM 250 × 20 mm; injection: 33 mg in 2 × 0.5 mL dichloromethane/methanol (1:1); solvent: hexane/ethanol/diethylamine (70:30:0.1); flow: 20 mL/min; detection: UV 254 nm; $R_t$ = 12.2-14.5 min. <br>$^1$H-NMR (400 MHz, DMSO-$d_6$): δ [ppm] = 0.89-1.01 (m, 6H), 1.01-1.29 (m, 4H), 1.33-1.53 (m, 2H), 1.73-1.96 (m, 3H), 2.08 (t, 1H), 2.18 (br., 6H), 4.69 (br., 1H), 6.95 (dd, 1H), 7.28 (d, 1H), 7.57 (d, 1H), 7.65 (d, 2H), 7.89 (d, 2H), 9.26 (very br., 1H), 12.18 (very br., 1H). |

Example 2-25

5-(5-Methyl-1,3,4-oxadiazol-2-yl)-1-(3,3,5,5-tetramethylcyclohexyl)-N-[4-(trifluoromethoxy)phenyl]-1H-benzimidazol-2-amine

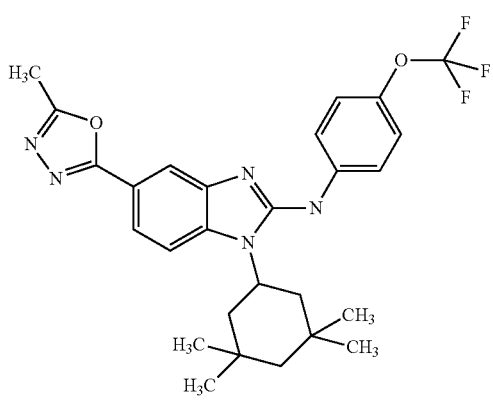 [SMILES: Cc1nnc(-c2ccc3c(c2)nc(Nc2ccc(OC(F)(F)F)cc2)n3C2CC(C)(C)CC(C)(C)C2)o1]

A solution of N'-acetyl-1-(3,3,5,5-tetramethylcyclohexyl)-2-{[4-(trifluoromethoxy)-phenyl]amino}-1H-benzimidazole-5-carbohydrazide (330 mg) (Intermediate 1-6) in phosphoryl chloride (5.0 mL) was stirred at 110° C. for 10 h. After removal of phosphoryl chloride, 10% aqueous NaOH was added (pH 12) followed by extraction with ethyl acetate. The combined organic phases were dried over sodium sulfate. The sovent was removed in vacuo followed by chromatography of the crude product. The desired compound was obtained in 10% yields (over 3 steps, 12 mg).

ESI+: 514 [M+1]

$^1$H-NMR (DMSO-$d_6$): δ [ppm]=0.98 (s, 6H), 1.13 (s, 6H), 1.23-1.42 (m, 2H), 1.55-1.66 (m, 2H), 1.99-2.13 (m, 2H), 2.57 (s, 3H), 4.58-4.76 (m, 1H), 7.34 (d, 2H), 7.65 (dd, 1H), 7.71 (d, 2H), 7.82 (d, 1H), 7.90 (d, 1H), 9.16 (br, 1H).

Example 2-26

5-(5-Methyl-1,2,4-oxadiazol-3-yl)-1-(3,3,5,5-tetramethylcyclohexyl)-N-[4-(trifluoromethoxy)phenyl]-1H-benzimidazol-2-amine

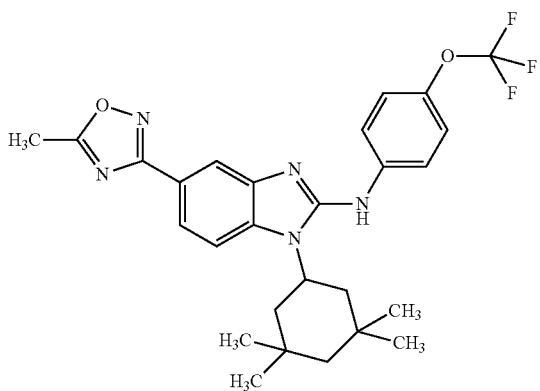 [SMILES: Cc1nc(-c2ccc3c(c2)nc(Nc2ccc(OC(F)(F)F)cc2)n3C2CC(C)(C)CC(C)(C)C2)no1]

To a solution of 5-N'-hydroxy-2-{[4-(trifluoromethoxy)phenyl]amino}-1-(3,3,5,5-tetramethylcyclohexyl)-1H-benzimidazole-5-carboximidamide (245 mg) (Intermediate 1-7) in toluene (5.0 mL) were added acetyl chloride (33 µL, 0.45 mmol) and NEt$_3$ (75 µL, 0.54 mmol). The mixture was stirred at 125° C. for 10 h. After removal of the solvent and subsequent purification by chromatography the desired compound was obtained in 18% yield (32 mg, over 3 steps).

ESI+: 514 [M+1]

$^1$H-NMR (DMSO-$d_6$): δ [ppm]=0.98 (s, 6H), 1.12 (s, 6H), 1.1-20-1.40 (m, 2H), 1.57-1.60 (m, 2H), 2.02-2.12 (m, 2H), 2.65 (s, 3H), 4.55-4.79 (m, 1H), 7.33 (d, 2H), 7.63-7.83 (m, 4H), 7.94 (d, 1H), 9.12 (s, 1H).

Example 2-27

(±) 5-(1H-tetrazol-5-yl)-N-[4-(trifluoromethoxy)phenyl]-1-[(trans)-3,3,5-trimethylcyclohexyl]-1H-benzimidazol-2-amine

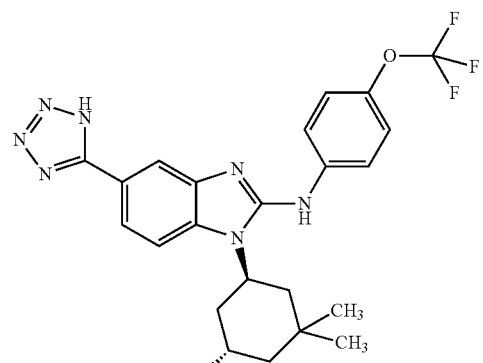

and

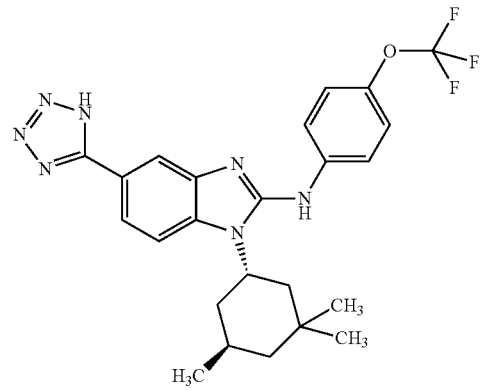

50 mg (0.11 mmol) (±) 2-{[4-(Trifluoromethoxy)phenyl]amino}-1-[(trans)-3,3,5-trimethylcyclohexyl]-1H-benzimidazole-5-carbonitrile (intermediate 1-8) and 6 mg (0.09 mmol) iron(III) acetate were dissolved in N,N-dimethylformamide (4.5 mL) and methanol (0.5 mL). Finally 42 mg (0.36 mmol) trimethylsilylazide was added. Nitrogen was passed through the mixture for 10 minutes; the vial was sealed and heated to 90° C. for 60 h. To the mixture was added water and it was subjected to extraction with ethyl acetate. The organic phases were dried with sodiumsulfate, the solvent was evaporated and purified by HPLC-colum chromatography, yielding 32 mg (55%) of the desired product.

$^1$H-NMR (400 MHz, DMSO-$d_6$): δ [ppm]=0.99 (s, 3H), 1.10 (s, 3H), 1.12 (d, 3H), 1.21-1.31 (m, 2H), 1.42-1.55 (m, 2H), 1.65 (br. m, 1H), 2.23-2.41 (m, 2H), 4.74 (br. m, 1H), 7.34 (m, 2H), 7.72-7.80 (m, 4H), 8.01 (s, 1H), 9.14 (s, 1H).

UPLC-MS (Method A): R$_t$=1.34 min; MS (ES+, M+1) 486.2; MS (ES−, M−1) 484.2.

Example 2-28

1-(3,3,5,5-tetramethylcyclohexyl)-5-(1H-tetrazol-5-yl)-N-[4-(trifluoromethoxy)-phenyl]-1H-benzimidazol-2-amine

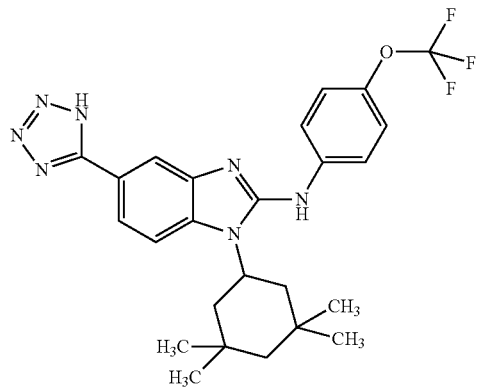 [SMILES: CC1(C)CC(n2c(Nc3ccc(OC(F)(F)F)cc3)nc3cc(-c4nnn[nH]4)ccc32)CC(C)(C)C1]

100 mg (0.22 mmol) 1-(3,3,5,5-tetramethylcyclohexyl)-2-{[4-(trifluoromethoxy)-phenyl]amino}-1H-benzimidazole-5-carbonitrile (Intermediate 1-7, step 1), and 12 mg (0.09 mmol) iron(III) acetate were dissolved in N,N-dimethylformamide (8 mL) and methanol (1 mL). Finally 83 mg (0.72 mmol) trimethylsilylazide were added. Nitrogen was passed through the mixture for 10 minutes, the vial was sealed and heated to 80° C. for 15 h. Due to low conversion, further iron(III) acetate (0.4 eq) and trimethylsilylazide (6 eq.) were added. The mixture was stirred at 90° C. for 67 h. Silica gel was added and the solvent was removed. The residue was directly submitted to flash chromatography with a silica gel cartridge (biotage, KP-SIL, dichloromethane/methanol gradient). Further purification by HPLC-colum chromatography followed, yielding 55 mg (50%) of the desired product.

$^1$H-NMR (300 MHz, DMSO-$d_6$): δ [ppm]=0.98 (s, 6H), 1.13 (s, 6H), 1.23-1.41 (m, 2H), 1.54-1.64 (m, 2H), 2.08 (t, 2H), 4.68 (br. m, 1H), 7.31-7.39 (m, 2H), 7.68-7.76 (m, 3H), 7.80-7.86 (m, 1H), 8.01 (s, 1H), 9.16 (s, 1H).

UPLC-MS (Method A): $R_t$=1.38 min; MS (ES+, M+1) 500.3; MS (ES−, M−1) 498.3.

Example 2-29

5-(3,5-dimethyl-1H-pyrazol-4-yl)-6-methyl-1-(3,3,5,5-tetramethylcyclohexyl)-N-[4-(trifluoromethoxy)phenyl]-1H-benzimidazol-2-amine

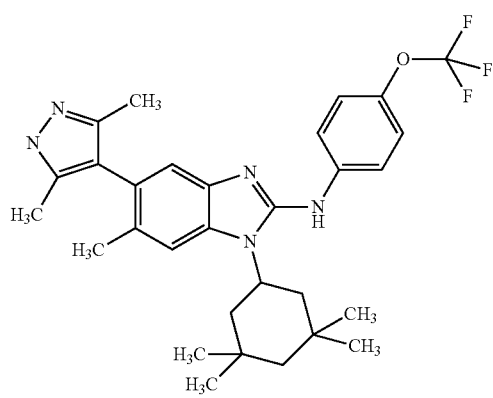 [SMILES: Cc1cc2c(cc1-c1c(C)n[nH]c1C)nc(Nc1ccc(OC(F)(F)F)cc1)n2C1CC(C)(C)CC(C)(C)C1]

A suspension of 5-bromo-6-methyl-1-(3,3,5,5-tetramethylcyclohexyl)-N-[4-(trifluoro-methoxy)phenyl]-1H-benzimidazol-2-amine (intermediate 1-4; 100 mg, 0.19 mmol), sodium carbonate (60 mg, 0.5 mmol) and 3,5-dimethyl-4-(4,4,5,5-tetramethyl-1,3,2-dioxaborolan-2-yl)-1H-pyrazole (CAS No. [857530-80-4]; 84 mg, 0.38 mmol) in 1,4-dioxane (1 mL) and water (0.25 mL) was degassed using argon in a microwave tube for 10 min. [1,1'-bis(diphenylphosphino)ferrocene]dichloropalladium(II) (14 mg, 0.02 mmol) was added and the tube sealed. The reaction was heated by microwave irradiation for 5 h at 140° C. The reaction was diluted with ethyl acetate (10 mL) and water (10 mL). The layers were separated and the aqueous layer was extracted with ethyl acetate (2×10 mL). The combined organics were dried over sodium sulfate and concentrated under vacuum. The crude material was purified by reverse phase chromatography (BIOTAGE SP4, 30 g Biotage cartridge) using acetonitrile and water containing 10 mM ammonium bicarbonate pH 10 buffer (3:97 to 100:0) to give the title compound (5.6 mg, 5.4%) as a pale purple solid.

UPLC-MS (Method H): $R_t$=3.36 min; m/z=540 (M+H)$^+$.

$^1$H-NMR (300 MHz, DMSO-$d_6$): δ [ppm]=0.96 (s, 6H), 1.07 (s, 6H), 1.20-1.30 (m, 2H), 1.52 (d, 2H), 1.94 (br. s, 6H), 2.06 (t, 2H), 2.09 (s, 3H), 4.50 (m, 1H), 7.02 (s, 1H), 7.26 (d, 2H), 7.45 (s, 1H), 7.56 (d, 2H), 8.87 (s, 1H).

Example 2-30

6-methyl-5-(5-methyl-4H-1,2,4-triazol-3-yl)-1-(3,3,5,5-tetramethylcyclohexyl)-N-[4-(trifluoromethoxy)phenyl]-1H-benzimidazol-2-amine

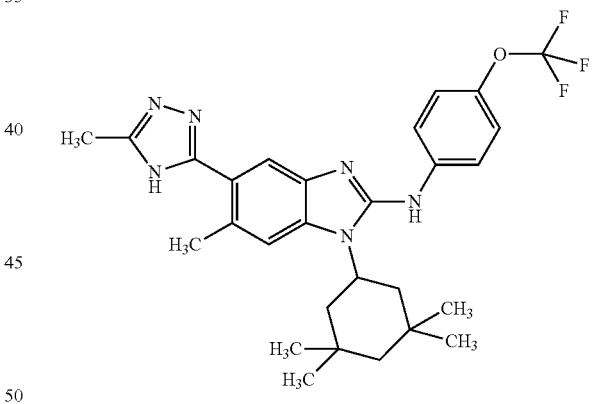

To a solution of N-[(1E)-1-(dimethylamino)ethylidene]-6-methyl-1-(3,3,5,5-tetramethylcyclohexyl)-2-{[4-(trifluoromethoxy)phenyl]amino}-1H-benzimidazole-5-carboxamide (intermediate 1-5; 50 mg, 0.09 mmol) in acetic acid (1 mL), hydrazine hydrate (0.015 mL, 0.31 mmol) was added and the reaction was heated to 90° C. for 30 min. The reaction was cooled, saturated sodium bicarbonate solution (20 mL) was added and the mixture was extracted with ethyl acetate (2×20 mL). The combined organics were dried over solid magnesium sulfate, filtered and concentrated under vacuum. The crude material was purified by flash silica column chromatography (dichloromethane) to give the title compound (19 mg, 39%) as a colourless solid.

UPLC-MS (Method G): $R_t$=0.60 min; m/z=527 (M+H)$^+$.

$^1$H-NMR (300 MHz, CDCl$_3$): δ [ppm]=0.73 (s, 6H), 0.96 (s, 6H), 1.20-1.41 (m, 2H), 1.50-1.70 (m, 2H), 1.95 (t, 2H), 2.54 (s, 3H), 2.87 (s, 3H), 4.45 (m, 1H), 7.04 (d, 2H), 7.19 (d, 2H), 7.25 (s, 1H), 7.41 (s, 1H), 8.23 (s, 1H).

Example 2-31

(±) 5-(5-methyl-1,3,4-oxadiazol-2-yl)-N-[4-(trifluoromethoxy)phenyl]-1-[(cis)-3,3,5-trimethylcyclohexyl]-1H-benzimidazol-2-amine

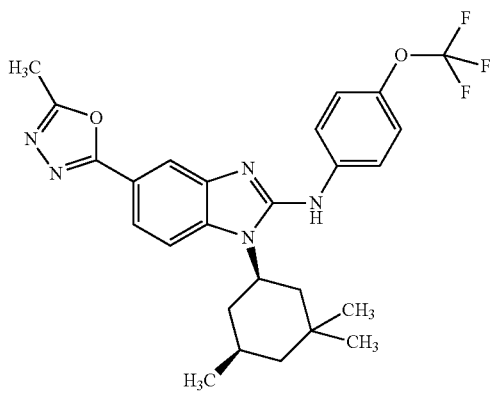

and

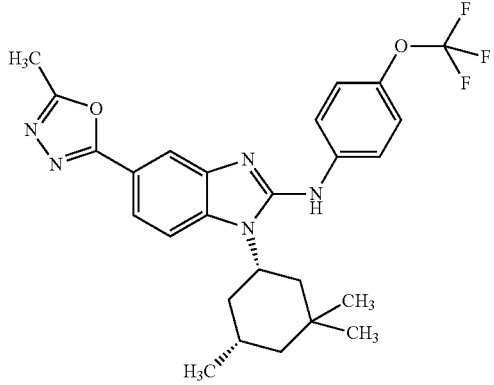

200 mg (0.37 mmol) 5-(4,4,5,5-Tetramethyl-1,3,2-dioxaborolan-2-yl)-N-[4-(trifluoromethoxy)phenyl]-1-(3,3,5-trimethylcyclohexyl)-1H-benzimidazol-2-amine (Intermediate 1-9), 60 mg (0.37 mmol) 2-bromo-5-methyl-1,3,4-oxadiazole (commercially available, CAS-RN: 864750-58-3), 30 mg (0.04 mmol) 1,1'-(bisdiphenylphosphino)ferrocenedichloropalladium(II) and 117 mg (1.1 mmol) sodium carbonate in 3.9 mL dioxane (degassed) and 0.55 mL water (degassed) were heated at 110° C. for 90 min in a microwave oven. Due to an incomplete reaction additional 20 mg catalyst were added and heating was continued at 110° C. for two hours. The reaction mixture was cooled and eluted with ethyl acetate (250 mL) via a FLAS column (20 g). After evaporation of the solvent the residue was purified by HPLC yielding 27.8 mg (14.4%) of the title compound.

UPLC-MS: $R_t$=1.46 min; m/z=500.2 (M+1).

$^1$H-NMR (300 MHz, DMSO-$d_6$): δ [ppm]=0.90-1.18 (m, 10H), 1.31-1.52 (m, 2H), 1.68-1.99 (m, 3H), 2.08 (t, 1H), 2.58 (s, 3H), 4.70 (br., 1H), 7.28-7.41 (m, 2H), 7.65 (d, 1H), 7.75 (d, 1H), 7.78-7.92 (m, 3H), 9.21 (s, 1H).

Example 2-32

(±) 5-(3,5-difluoro-4-methoxyphenyl)-N-[4-(trifluoromethoxy)phenyl]-1-[(cis)-3,3,5-trimethylcyclohexyl]-1H-benzimidazol-2-amine

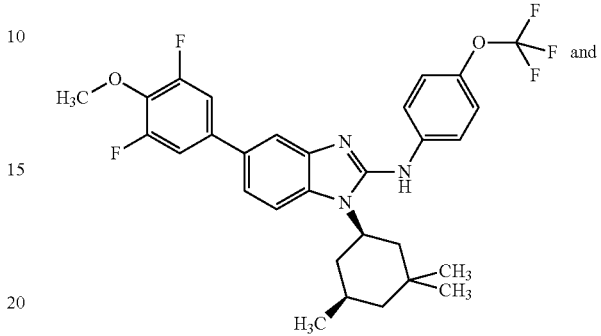

and

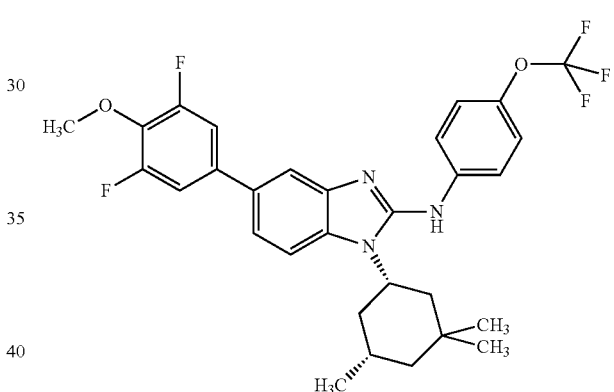

200 mg (0.37 mmol) 5-(4,4,5,5-Tetramethyl-1,3,2-dioxaborolan-2-yl)-N-[4-(trifluoromethoxy)phenyl]-1-(3,3,5-trimethylcyclohexyl)-1H-benzimidazol-2-amine (Intermediate 1-9) 82.1 mg (0.37 mmol) 5-bromo-1,3-difluoro-2-methoxybenzene (commercially available, CAS-RN: 104197-14-0), 30 mg (0.04 mmol) 1,1'-(bisdiphenylphosphino)ferrocenedichloropalladium(II) and 117 mg (1.1 mmol) sodium carbonate in 3.9 mL dioxane (degassed) and 0.55 mL water (degassed) were heated at 110° C. for 90 min in a microwave oven. The reaction mixture was cooled and eluted with ethyl acetate (250 mL) via a FLAS column (20 g). After evaporation of the solvent the residue was purified by HPLC yielding 81.8 mg (37.7%) of the title compound.

UPLC-MS: $R_t$=1.68 min; m/z=560.2 (M+1).

$^1$H-NMR (300 MHz, DMSO-$d_6$): δ [ppm]=0.90-1.18 (m, 10H), 1.32-1.52 (m, 2H), 1.68-2.00 (m, 3H), 2.06 (t, 1H), 3.93 (s, 3H), 4.67 (br., 1H), 7.29-7.40 (m, 3H), 7.41-7.53 (m, 2H), 7.60 (d, 1H), 7.72 (d, 1H), 7.84 (d, 2H), 9.11 (s, 1H).

Example 2-33

(±) 2,6-difluoro-4-(2-{[4-(trifluoromethoxy)phenyl]amino}-1-[(cis)-3,3,5-trimethylcyclohexyl]-1H-benzimidazol-5-yl)phenol

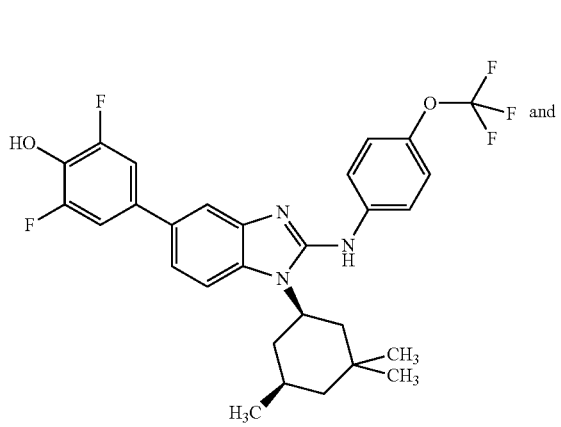

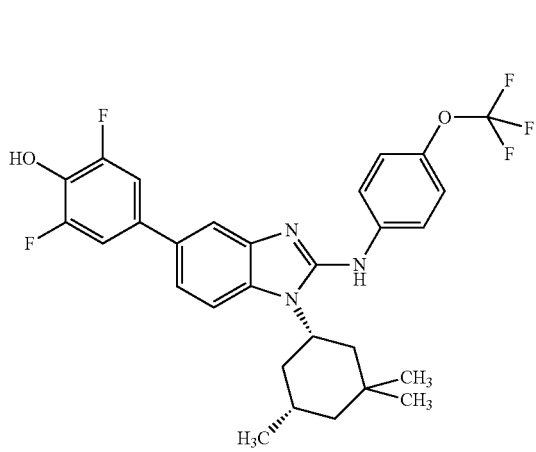

200 mg (0.37 mmol) 5-(4,4,5,5-Tetramethyl-1,3,2-dioxaborolan-2-yl)-N-[4-(trifluoromethoxy)phenyl]-1-(3,3,5-trimethylcyclohexyl)-1H-benzimidazol-2-amine (Intermediate 1-9), 76.9 mg (0.37 mmol) 4-bromo-2,6-difluorophenol (commercially available, CAS-RN: 104197-13-9), 30 mg (0.04 mmol) 1,1'-(bisdiphenylphosphino)ferrocenedichloropalladium(II) and 117 mg (1.1 mmol) sodium carbonate in 3.9 mL dioxane (degassed) and 0.55 mL water (degassed) were heated at 110° C. for 90 min in a microwave oven. The reaction mixture was cooled and eluted with ethyl acetate (250 mL) via a FLAS column (20 g). After evaporation of the solvent the residue was purified by HPLC yielding 30.5 mg (14.4%) of the title compound.

UPLC-MS: $R_t$=1.44 min; m/z=546.2 (M+1).

$^1$H-NMR (300 MHz, DMSO-d$_6$): δ [ppm]=0.90-1.18 (m, 10H), 1.32-1.50 (m, 2H), 1.68-1.99 (m, 3H), 2.05 (t, 1H), 4.66 (br., 1H), 7.22-7.45 (m, 5H), 7.56 (d, 1H), 7.65 (d, 1H), 7.83 (d, 2H), 9.08 (s, 1H), 10.03 (br., 1H).

Example 2-34

(±) 2,6-dimethyl-4-(2-{[4-(trifluoromethoxy)phenyl]amino}-1-[(cis)-3,3,5-trimethylcyclohexyl]-1H-benzimidazol-5-yl)phenol

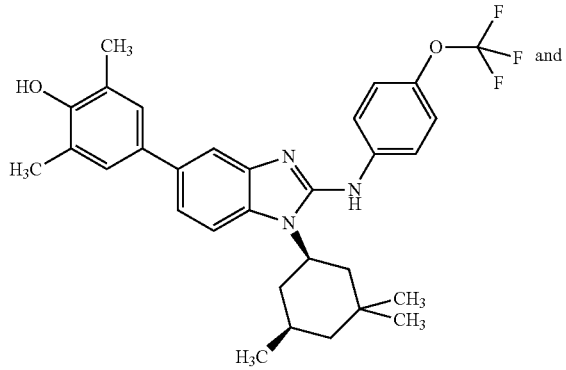

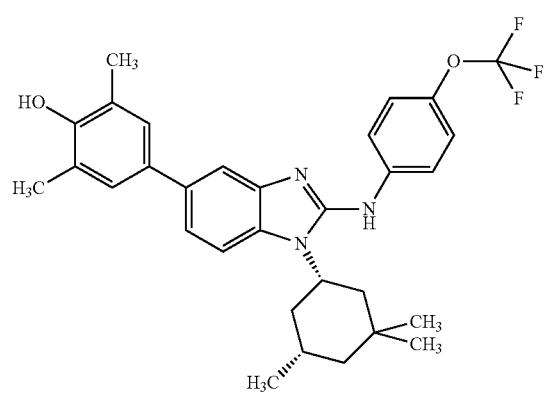

200 mg (0.37 mmol) 5-(4,4,5,5-Tetramethyl-1,3,2-dioxaborolan-2-yl)-N-[4-(trifluoromethoxy)phenyl]-1-(3,3,5-trimethylcyclohexyl)-1H-benzimidazol-2-amine (Intermediate 1-9) 74 mg (0.37 mmol) 4-bromo-2,6-dimethylphenol (commercially available, CAS-RN: 2374-05-2), 30 mg (0.04 mmol) 1,1'-(bisdiphenylphosphino)ferrocenedichloropalladium(II) and 117 mg (1.1 mmol) sodium carbonate in 3.9 mL dioxane (degassed) and 0.55 mL water (degassed) were heated at 110° C. for 90 min in a microwave oven. The reaction mixture was cooled and eluted with ethyl acetate (250 mL) via a FLAS column (20 g). After evaporation of the solvent the residue was purified by HPLC yielding 7 mg (3%) of the desired compound.

UPLC-MS (method B): $R_t$=1.68 min; m/z=538.3 (M+1).

$^1$H-NMR (300 MHz, DMSO-d$_6$): δ [ppm]=0.89-1.25 (m, 10H), 1.40 (d, 1H), 1.59 (d, 1H), 1.70-2.01 (m, 3H), 2.10 (t, 1H), 2.20 (s, 6H), 4.69 (br., 1H), 7.18 (s, 2H), 7.38 (d, 1H), 7.42-7.58 (m, 3H), 7.60-7.84 (m, 3H), 8.32 (br., 1H), 10.1 (very br., 1H).

Example 2-35

(±) 5-(3-ethoxy-5-methyl-1,2-oxazol-4-yl)-N-[4-(trifluoromethoxy)phenyl]-1-[(cis)-3,3,5-trimethyl-cyclohexyl]-1H-benzimidazol-2-amine

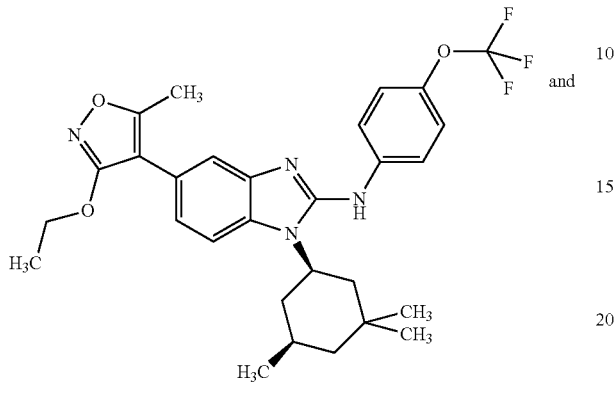

and

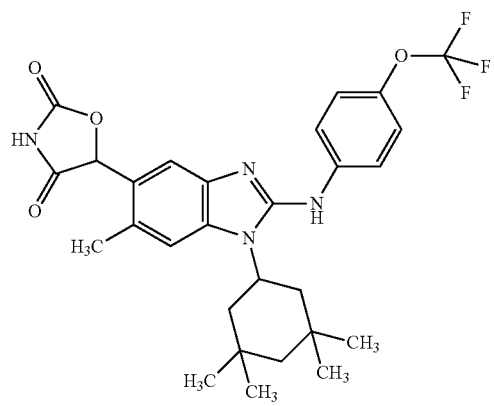 [SMILES: Cc1cc2c(cc1C1OC(=O)NC1=O)nc(Nc1ccc(OC(F)(F)F)cc1)n2C1CC(C)(C)CC(C)(C)C1]

Example 2-36

5-[6-methyl-1-(3,3,5,5-tetramethylcyclohexyl)-2-{[4-(trifluoromethoxy)phenyl]amino}-1H-benzimidazol-5-yl]-1,3-oxazolidine-2,4-dione 200 mg (0.37 mmol) 5-(4,4,5,5-Tetramethyl-1,3,2-dioxaborolan-2-yl)-N-[4-(trifluoromethoxy)phenyl]-1-(3,3,5-trimethylcyclohexyl)-1H-benzimidazol-2-amine (Intermediate 1-9) 75.8 mg (0.37 mmol) 4-bromo-3-ethoxy-5-methyl-1,2-oxazole (commercially available, CAS-RN: 169310-98-9), 30 mg (0.04 mmol) 1,1'-(bisdiphenylphosphino)ferrocenedichloropalladium(II) and 117 mg (1.1 mmol) sodium carbonate in 3.9 mL dioxane (degassed) and 0.55 mL water (degassed) were heated at 110° C. for 90 min in a microwave oven. The reaction mixture was cooled and eluted with ethyl acetate (250 mL) via a FLAS column (20 g). After evaporation of the solvent the residue was purified by HPLC yielding 89.1 mg (37.9%) of the title compound.

UPLC-MS: $R_t$=1.32 min; m/z=543.3 (M+1).

$^1$H-NMR (300 MHz, DMSO-$d_6$): δ [ppm]=0.88-1.18 (m, 10H), 1.20 (t, 3H), 1.33-1.49 (m, 2H), 1.69-1.98 (m, 3H), 2.07 (t, 1H), 2.41 (s, 3H), 3.87 (q, 2H), 4.66 (br., 1H), 7.21 (dd, 1H), 7.26-7.39 (m, 2H), 7.52 (d, 1H), 7.59 (d, 1H), 7.78-7.89 (m, 2H), 9.09 (s, 1H).

To a solution of ethyl [5-(2,4-dioxo-1,3-oxazolidin-5-yl)-6-methyl-1-(3,3,5,5-tetramethylcyclohexyl)-1H-benzimidazol-2-yl][4-(trifluoromethoxy)phenyl]carbamate (intermediate 1-10; 42 mg, 0.07 mmol) in methanol (5 mL) and water (1 mL), sodium hydroxide (6 mg, 0.14 mmol) was added. The reaction mixture was stirred at room temperature for 18 h then quenched by addition of aqueous hydrochloric acid (10 mL, 1 M) and extracted with ethyl acetate (3×25 mL). The combined organic layers were dried over solid sodium sulfate and concentrated under vacuum. The crude material was purified by triturating with dichloromethane to give the title compound (36 mg, 97%) as a colourless solid.

UPLC-MS (Method F): $R_t$=0.75 min; m/z=545 (M+H)$^+$.

$^1$H-NMR (300 MHz, Methanol-$d_4$): δ [ppm]=0.86 (s, 6H), 1.07 (s, 6H), 1.34 (s, 2H), 1.62 (d, 2H), 2.10 (t, 2H), 2.53 (s, 3H), 4.64 (m, 1H), 6.21 (s, 1H), 7.15-7.33 (m, 5H), 7.44 (s, 1H).

Example 2-37

5-[6-methyl-1-(3,3,5,5-tetramethylcyclohexyl)-2-{[4-(trifluoromethoxy)phenyl]amino}-1H-benzimidazol-5-yl]-1,2-oxazol-3-ol

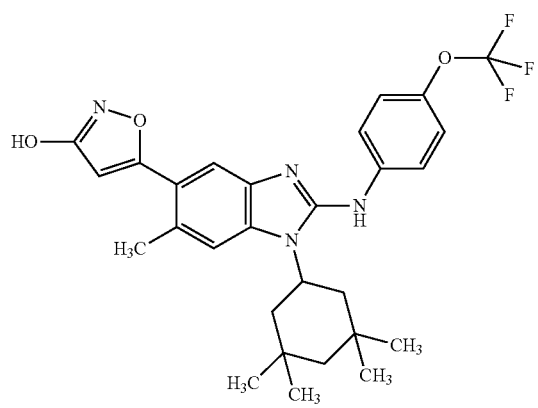 [SMILES: Cc1cc2c(cc1-c1cc(O)no1)nc(Nc1ccc(OC(F)(F)F)cc1)n2C1CC(C)(C)CC(C)(C)C1]

N-Hydroxy-2-{2-[6-methyl-1-(3,3,5,5-tetramethylcyclohexyl)-2-{[4-(trifluoromethoxy)phenyl]amino}-1H-benzimidazol-5-yl]-1,3-dioxolan-2-yl}acetamide (intermediate 1-11; 78 mg, 0.04 mmol, 33% purity) was dissolved in hydrochloric acid (3 mL, 9.90 mmol, 3.3 M in methanol) and stirred at 70° C. for 5 h. The solvent was removed by evaporation and the residue was dissolved in dichloromethane (20 mL) and saturated sodium bicarbonate solution (20 mL). The layers were separated and the aqueous layer was extracted with dichloromethane (2×20 mL). The combined organic layers were dried over solid sodium sulfate and concentrated under vacuum. The material was purified by reverse phase chromatography (BIOTAGE SP4, 30 g Biotage cartridge) using acetonitrile and water containing 10 mM ammonium bicarbonate at pH 10 buffer (10:90 to 100:0) to give the title compound (20 mg, 43%) as a colourless solid.

UPLC-MS (Method F): $R_t$=0.79; m/z=529 $(M+H)^+$.

$^1$H-NMR (400 MHz, DMSO-$d_6$): δ [ppm]=0.95 (s, 6H), 1.07 (s, 6H), 1.20-1.42 (m, 2H), 1.45-1.56 (m, 2H), 2.04 (t, 2H), 2.49 (s, 2H), 4.58 (m, 1H), 6.19 (s, 1H), 7.29 (d, 2H), 7.52 (s, 1H), 7.60-7.70 (m, 3H), 9.02 (br s, 1H).

Further, the compounds of formula (I) of the present invention can be converted to any salt as described herein, by any method which is known to the person skilled in the art. Similarly, any salt of a compound of formula (I) of the present invention can be converted into the free compound, by any method which is known to the person skilled in the art.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like. For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both. Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC—CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 min.

Lyophilised powder for IV administration: A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 min.

Intramuscular suspension: The following solution or suspension can be prepared, for intramuscular injection:
50 mg/mL of the desired, water-insoluble compound of this invention
5 mg/mL sodium carboxymethylcellulose
4 mg/mL TWEEN 80
9 mg/mL sodium chloride
9 mg/mL benzyl alcohol Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Combination Therapies

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known chemotherapeutic agents or anti-cancer agents, e.g. anti-hyper-proliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, toposisomerase inhibitors, biological response modifiers, or anti-hormones.

The term "chemotherapeutic anti-cancer agents", includes but is not limited to 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 1000394, belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, copanlisib, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, radium-223 chloride, raloxifene, raltitrexed, ranimustine, razoxane, refametinib, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

The compounds of the invention may also be administered in combination with protein therapeutics. Such protein therapeutics suitable for the treatment of cancer or other angiogenic disorders and for use with the compositions of the invention include, but are not limited to, an interferon (e.g., interferon .alpha., .beta., or .gamma.) supraagonistic monoclonal antibodies, Tuebingen, TRP-1 protein vaccine, Colostrinin, anti-FAP antibody, YH-16, gemtuzumab, infliximab, cetuximab, trastuzumab, denileukin diftitox, rituximab, thymosin alpha 1, bevacizumab, mecasermin, mecasermin rinfabate, oprelvekin, natalizumab, rhMBL, MFE-CP1+ZD-2767-P, ABT-828, ErbB2-specific immunotoxin, SGN-35, MT-103, rinfabate, AS-1402, B43-genistein, L-19 based radioimmunotherapeutics, AC-9301, NY-ESO-1 vaccine, IMC-1C11, CT-322, rhCC10, r(m)CRP, MORAb-009, aviscumine, MDX-1307, Her-2 vaccine, APC-8024, NGR-hTNF, rhH1.3, IGN-311, Endostatin, volociximab, PRO-1762, lexatumumab, SGN-40, pertuzumab, EMD-273063, L19-IL-2 fusion protein, PRX-321, CNTO-328, MDX-214, tigapotide, CAT-3888, labetuzumab, alpha-particle-emitting radioisotope-(linked lintuzumab, EM-1421, HyperAcute vaccine, tucotuzumab celmoleukin, galiximab, HPV-16-E7, Javelin—prostate cancer, Javelin—melanoma, NY-ESO-1 vaccine, EGF vaccine, CYT-004-MelQbG10, WT1 peptide, oregovomab, ofatumumab, zalutumumab, cintredekin besudotox, WX-G250, Albuferon, aflibercept, denosumab, vaccine, CTP-37, efungumab, or 131I-chTNT-1/B. Monoclonal antibodies useful as the protein therapeutic include, but are not limited to, muromonab-CD3, abciximab, edrecolomab, daclizumab, gentuzumab, alemtuzumab, ibritumomab, cetuximab, bevicizumab, efalizumab, adalimumab, omalizumab, muromomab-CD3, rituximab, daclizumab, trastuzumab, palivizumab, basiliximab, and infliximab.

A compound of general formula (I) as defined herein can optionally be administered in combination with one or more of the following: ARRY-162, ARRY-300, ARRY-704, AS-703026, AZD-5363, AZD-8055, BEZ-235, BGT-226, BKM-120, BYL-719, CAL-101, CC-223, CH-5132799, deforolimus, E-6201, enzastaurin, GDC-0032, GDC-0068, GDC-0623, GDC-0941, GDC-0973, GDC-0980, GSK-2110183, GSK-2126458, GSK-2141795, MK-2206, novolimus, OSI-027, perifosine, PF-04691502, PF-05212384, PX-866, rapamycin, RG-7167, RO-4987655, RO-5126766, selumetinib, TAK-733, trametinib, triciribine, UCN-01, WX-554, XL-147, XL-765, zotarolimus, ZSTK-474.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone, (2) provide for the administration of lesser amounts of the administered chemo-therapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumor progression, and/or (8) yield efficacy and tolerability results at least as good as those of the agents used alone, compared to known instances where other cancer agent combinations produce antagonistic effects.

Methods of Sensitizing Cells to Radiation

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated with one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in vivo.

As mentioned supra, the compounds of the present invention have surprisingly been found to effectively inhibit mutated isocitratdehydrogenase 1 (mIDH1 R132H) and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses are affected by inhibition of mutated isocitratdehydrogenase 1 (mIDH1 R132H), such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

In accordance with another aspect therefore, the present invention covers a compound of general formula (I), or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of general formula (I), described supra, or a stereoisomer, a tautomer, an N-oxide, a hydrate, a solvate, or a salt thereof, particularly a pharmaceutically acceptable salt thereof, or a mixture of same, for the prophylaxis or treatment of a disease.

Another particular aspect of the present invention is therefore the use of a compound of general formula (I) described supra for manufacturing a pharmaceutical composition for the treatment or prophylaxis of a disease.

The diseases referred to in the two preceding paragraphs are diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The term "inappropriate" within the context of the present invention, in particular in the context of "inappropriate cellular immune responses, or inappropriate cellular inflammatory responses", as used herein, is to be understood as meaning a response which is less than, or greater than normal, and which is associated with, responsible for, or results in, the pathology of said diseases.

Preferably, the use is in the treatment or prophylaxis of diseases, wherein the diseases are haemotological tumours, solid tumours and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder.

Hyperproliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, anaplastic astrocytoma, diffuse astrocytoma, glioblastoma, oligodendroglioma, secondary glioblastoma multiforme as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma. Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyperproliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases of said method are haematological tumours, solid tumour and/or metastases thereof.

The compounds of the present invention can be used in particular in therapy and prevention, i.e. prophylaxis, of tumour growth and metastases, especially in solid tumours of all indications and stages with or without pre-treatment of the tumour growth.

Methods of testing for a particular pharmacological or pharmaceutical property are well known to persons skilled in the art.

The example testing experiments described herein serve to illustrate the present invention and the invention is not limited to the examples given.

Biological Assays:

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

Mutant IDH1 R132H Biochemical Assay mIDH1 catalyzes the NADPH-dependent reduction of alpha-ketoglutarate (α-KG) to (2R)-2-hydroxyglutarate (2-HG). NADPH consumption was measured by luminescent readout.

The biochemical reactions were performed at 32° C. in 384-well plates using a reaction volume of 41 µl and the following assay buffer conditions: 50 mM Tris pH 7.5, 100 mM NaCl, 20 mM $MgCl_2$, 0.05% BSA, 0.01% Brij, 1 µM NADPH, and 250 µM α-KG. The IDH1 R132H enzyme was used in a final concentration of 1.5 nM. Test compounds were used in a concentration range between 0.002 and 10 µM. The final DMSO concentration was 2.4%.

The reaction was incubated for 30 minutes, then 40 µl of detection mix (0.75 µg/ml Luciferase, 0.02 U/ml Oxidoreductase, 4 µg/ml FMN, 2 µl/ml Decanal/Ethanol, 50 mM Tris pH 7.5, 0.5% Glycerin, 0.01% Tween-20, 0.05% BSA) was added. Luminescence was measured on a luminescent reader (10 seconds measuring time, 1 second integration period, 30% sensitivity). The decrease in luminescence is proportional to mIDH1 activity. $IC_{50}$ values are determined by interpolation from plots of relative luminescence versus inhibitor concentration.

TABLE 2

$IC_{50}$ values of selected examples in mutant IDH1 R132H biochemical assay

| Example | Mutant IDH1 R132H $IC_{50}$ [µM] |
|---|---|
| 2-1 | 0.12 |
| 2-1-1 | 0.24 |
| 2-1-2 | 0.07 |
| 2-2 | 0.07 |
| 2-3 | 0.46 |
| 2-4 | 0.08 |
| 2-5 | 0.09 |
| 2-5-1 | 0.67 |
| 2-5-2 | 1.54 |
| 2-7 | 0.11 |
| 2-8 | 0.13 |
| 2-9 | 0.18 |
| 2-10 | 0.14 |
| 2-10-1 | 0.30 |
| 2-10-2 | 0.14 |
| 2-11 | 0.21 |
| 2-12 | 0.10 |
| 2-12-1 | 4.3 |
| 2-12-2 | 1.6 |
| 2-13 | 1.1 |
| 2-13-1 | 0.24 |
| 2-13-2 | 1.0 |
| 2-14 | 1.3 |
| 2-15 | 1.5 |
| 2-16 | 0.29 |
| 2-16-1 | 7.8 |
| 2-16-2 | 0.78 |
| 2-17 | 0.44 |
| 2-18 | 4.0 |
| 2-19 | 1.9 |
| 2-20 | 10 |
| 2-21 | 10 |
| 2-21-1 | 1.1 |
| 2-21-2 | 0.29 |
| 2-22 | 0.77 |
| 2-23 | 10 |
| 2-23-1 | 10 |
| 2-23-2 | 0.18 |
| 2-24 | 10 |
| 2-24-1 | 10 |
| 2-24-2 | 0.14 |
| 2-25 | 0.13 |
| 2-26 | 0.22 |
| 2-27 | 1.8 |
| 2-28 | 0.07 |
| 2-29 | 4 |
| 2-30 | 0.12 |
| 2-31 | 0.39 |
| 2-32 | 10 |
| 2-33 | 0.67 |
| 2-34 | 0.18 |
| 2-35 | 0.24 |
| 2-36 | 0.014 |
| 2-37 | 0.03 |

Mutant IDH1 Cellular Assay

Levels of (2R)-2-hydroxyglutarate (2HG) were measured in medium of a cell line with overexpression of mutated isocitrate dehydrogenase (mIDH) protein. mIDH catalyzes the NADPH-dependent reduction of alpha-ketoglutarate to 2-HG. Cells (LN229 R132H, Mohrenz et al., Apoptosis (2013) 18:1416-1425) were grown in DMEM containing 10% FCS. They were harvested by trypsin and seeded into 96-well plates. Cells were incubated overnight at 37° C. in 5% $CO_2$. The next day test compounds were added to each cell well. The final concentration of DMSO was 0.1% and DMSO controls were included. The plates were then placed in an incubator for 24 hours.

2-HG was measured according to Balss et al. (Acta Neuropathol (2012) 124: 883-891). Briefly, $HClO_4$ was added to each well and the plates were centrifuged. Aliquots are removed and incubated with hydroxyglutarate dehydrogenase (HGDH), diaphorase, NAD+, and resazurin. The conversion of resazurin to resorufin was detected by fluorescence spectroscopy at Ex 540 nm Em 600 nm. The increase in fluorescence is proportional to 2-HG production. $IC_{50}$ values are determined by interpolation from plots of relative fluorescence vs inhibitor concentration.

TABLE 3

$IC_{50}$ values of selected examples in mutant IDH1 cellular assay

| Example | Mutant IDH1 $IC_{50}$ [µM] |
|---|---|
| 2-1 | 0.90 |
| 2-2 | 0.36 |
| 2-4 | 0.60 |
| 2-5 | 4 |
| 2-5-2 | 1.5 |
| 2-7 | 1.2 |
| 2-8 | 2.0 |
| 2-9 | 2.0 |
| 2-10 | 2.0 |
| 2-10-1 | 10 |
| 2-10-2 | 3.0 |
| 2-11 | 2.8 |
| 2-12 | 8.0 |
| 2-13 | 5.0 |
| 2-19 | 10 |
| 2-20 | 4.0 |
| 2-21-1 | 10 |
| 2-21-2 | 2.5 |
| 2-22 | 2.5 |
| 2-23-2 | 10 |
| 2-24-2 | 7.0 |
| 2-26 | 10 |

TABLE 3-continued

IC$_{50}$ values of selected examples in mutant IDH1 cellular assay

| Example | Mutant IDH1 IC$_{50}$ [µM] |
|---|---|
| 2-28 | 0.20 |
| 2-29 | 2.7 |
| 2-30 | 1.5 |
| 2-36 | 0.022 |
| 2-37 | 0.25 |

The invention claimed is:
1. A compound of formula (I)

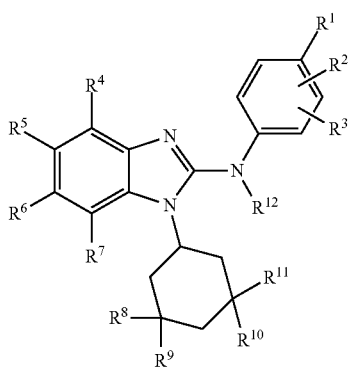

(I)

wherein:
R$^1$ is a halogen atom or a group selected from the group consisting of:
  C$_1$-C$_6$-alkyl, C$_1$-C$_6$-alkoxy, C$_1$-C$_6$-haloalkyl, C$_1$-C$_6$-haloalkoxy, cyano, (C$_1$-C$_6$-alkyl)-S—, and (C$_1$-C$_6$-haloalkyl)-S—;
R$^2$ is a hydrogen atom;
R$^3$ is a hydrogen atom;
R$^4$ is a hydrogen atom;
R$^5$ is a phenyl or heteroaryl group,
  wherein said phenyl or heteroaryl group is optionally substituted with one or more substituents independently selected from the group consisting of:
  halo-, cyano, C$_1$-C$_6$-alkyl, C$_3$-C$_6$-cycloalkyl, C$_1$-C$_6$-haloalkyl, C$_1$-C$_6$-haloalkoxy, nitro, R$^{13}$O—, R$^{13}$S—, R$^{13}$OC(=O)—(C$_1$-C$_6$-alkyl)-, R$^{13}$OC(=O)—(C$_2$-C$_6$-alkenyl)-, R$^{13}$OC(=O)—(C$_1$-C$_6$-alkoxy)-, R$^{14}$(R$^{15}$)NC(=O)—(C$_1$-C$_6$-alkyl)-, R$^{14}$(R$^{15}$)NC(=O)—(C$_2$-C$_6$-alkenyl)-, R$^{14}$(R$^{15}$)NC(=O)—(C$_1$-C$_6$-alkoxy)-, (C$_1$-C$_6$-alkyl)-S—, (C$_1$-C$_6$-alkyl)-S(=O)—, (C$_1$-C$_6$-alkyl)-S(=O)$_2$—, (C$_1$-C$_6$-haloalkyl)-S—, —C(=O)OR$^{13}$, —C(=O)N(R$^{14}$)R$^{15}$, —C(=O)N(R$^{14}$)S(=O)$_2$R$^{16}$, —N(R$^{14}$)R$^{15}$, —N(R$^{14}$)C(=O)R$^{16}$, —N(R$^{14}$)C(=O)R$^{17}$, —N(R$^{14}$)S(=O)$_2$R$^{16}$, —S(=O)$_2$OR$^{13}$, and —S(=O)$_2$N(R$^{14}$)R$^{15}$;
R$^6$ is a hydrogen atom, a halogen atom, or a group selected from the group consisting of C$_1$-C$_6$-alkyl and C$_1$-C$_6$-alkoxy;
R$^7$ is a hydrogen atom;
R$^8$ is C$_1$-C$_3$-alkyl;
R$^9$, R$^{10}$, and R$^{11}$
  are independently selected from the group consisting of hydrogen and C$_1$-C$_3$-alkyl;
R$^{12}$ is a hydrogen atom;

R$^{13}$ is a hydrogen atom or a group selected from the group consisting of:
  C$_1$-C$_6$-alkyl, C$_3$-C$_6$-cycloalkyl, HO—(C$_2$-C$_6$-alkyl)-, and (C$_1$-C$_3$-alkoxy)-(C$_2$-C$_6$-alkyl)-;
R$^{14}$ and R$^{15}$
  are independently selected from the group consisting of:
  hydrogen, C$_1$-C$_6$-alkyl, C$_3$-C$_6$-cycloalkyl, HO—(C$_2$-C$_6$-alkyl)-, (C$_1$-C$_3$-alkoxy)-(C$_2$-C$_6$-alkyl)-, H$_2$N—(C$_2$-C$_6$-alkyl)-, (C$_1$-C$_3$-alkyl)N(H)(C$_2$-C$_6$-alkyl)-, (C$_1$-C$_3$-alkyl)$_2$N(C$_2$-C$_6$-alkyl)-, R$^{13}$OC(=O)—(C$_1$-C$_6$-alkyl)-, 4- to 6-membered heterocycloalkyl, phenyl, heteroaryl, phenyl-(C$_1$-C$_6$-alkyl)-, and heteroaryl-(C$_1$-C$_6$-alkyl)-,
  wherein said phenyl and heteroaryl groups are optionally substituted with one or two substituents independently selected from the group consisting of:
  C$_3$-C$_6$-cycloalkyl, C$_1$-C$_3$-alkoxy, C$_3$-C$_6$-cycloalkyloxy, C$_1$-C$_3$-haloalkoxy, halogen, cyano, —C(=O)OR$^{13}$, and —C(=O)NH$_2$;
or
R$^{14}$ and R$^{15}$
  are taken together with the nitrogen atom to which they are attached to form a 4-6-membered heterocycloalkyl,
  wherein said 4-6-membered heterocycloalkyl is optionally substituted with one substituent selected from the group consisting of:
  C$_1$-C$_3$-alkyl C$_1$-C$_3$-haloalkyl C$_1$-C$_3$-alkoxy, C$_1$-C$_3$-haloalkoxy, C$_3$-C$_6$-cycloalkyl, C$_3$-C$_6$-cycloalkyloxy, amino, hydroxy, halogen, and cyano,
  or
  wherein said 4-6-membered heterocycloalkyl is optionally substituted with one or two halogen atoms;
R$^{16}$ is a hydrogen atom or a group selected from the group consisting of:
  C$_1$-C$_6$-alkyl, C$_3$-C$_6$-cycloalkyl, HO—(C$_3$-C$_6$-cycloalkyl)-, C$_1$-C$_6$-haloalkyl, (C$_1$-C$_3$-alkoxy)-(C$_1$-C$_6$-alkyl)-, phenyl, heteroaryl, and 4- to 6-membered heterocycloalkyl,
  wherein said phenyl and heteroaryl groups are optionally substituted with one or two substituents independently selected from the group consisting of:
  C$_1$-C$_3$-alkyl, C$_3$-C$_6$-cycloalkyl, C$_1$-C$_3$-alkoxy, C$_3$-C$_6$-cycloalkyloxy, C$_1$-C$_3$-haloalkyl, C$_1$-C$_3$-haloalkoxy, halogen, cyano, —C(=O)OR$^{13}$, and —C(=O)N(R$^{14}$)R$^{15}$; and
R$^{17}$ is a group selected from the group consisting of —N(R$^{14}$)R$^{15}$ and C$_1$-C$_6$-alkoxy,
or a stereoisomer, a tautomer, an N-oxide, a hydrate, a solvate, or a salt thereof, or a mixture of any of the foregoing.

2. The compound according to claim 1, wherein:
R$^1$ is a group selected from the group consisting of:
  C$_1$-C$_3$-alkyl, C$_1$-C$_3$-alkoxy, C$_1$-C$_3$-haloalkyl, C$_1$-C$_3$-haloalkoxy, (C$_1$-C$_3$-alkyl)-S—, and (C$_1$-C$_3$-haloalkyl)-S—,
or a stereoisomer, a tautomer, an N-oxide, a hydrate, a solvate, or a salt thereof, or a mixture of any of the foregoing.

3. The compound according to claim 1, wherein:
R$^1$ is a group selected from the group consisting of:
  C$_1$-C$_3$-haloalkyl, C$_1$-C$_3$-haloalkoxy, and (C$_1$-C$_3$-haloalkyl)-S—,
or a stereoisomer, a tautomer, an N-oxide, a hydrate, a solvate, or a salt thereof, or a mixture of any of the foregoing.

4. The compound according to claim 1, wherein:
$R^5$ is a phenyl or heteroaryl group,
wherein said phenyl or heteroaryl group is optionally substituted with one or more substituents independently selected from the group consisting of:
halo-, cyano, $C_1$-$C_6$-alkyl, $C_3$-$C_6$-cycloalkyl, $C_1$-$C_6$-haloalkyl, $C_1$-$C_6$-haloalkoxy, nitro, $R^{13}O$—, $R^{13}S$—, $R^{13}OC(=O)$—($C_1$-$C_6$-alkyl)-, $R^{13}OC(=O)$—($C_2$-$C_6$-alkenyl)-, $R^{13}OC(=O)$—($C_1$-$C_6$-alkoxy)-, $R^{14}(R^{15})NC(=O)$—($C_1$-$C_6$-alkyl)-, $R^{14}(R^{15})NC(=O)$—($C_2$-$C_6$-alkenyl)-, $R^{14}(R^{15})NC(=O)$—($C_1$-$C_6$-alkoxy)-, ($C_1$-$C_6$-alkyl)-S—, ($C_1$-$C_6$-alkyl)-S(=O)—, ($C_1$-$C_6$-alkyl)-S(=O)$_2$—, ($C_1$-$C_6$-haloalkyl)-S—, —C(=O)$OR^{13}$, —C(=O)N($R^{14}$)$R^{15}$, —C(=O)N($R^{14}$)S(=O)$_2R^{16}$, —N($R^4$)$R^{15}$, —N($R^{14}$)C(=O)$R^{16}$, —N($R^{14}$)C(=O)$R^{17}$, —N($R^{14}$)S(=O)$_2R^{16}$, —S(=O)$_2OR^{13}$, and —S(=O)$_2$N($R^{14}$)$R^{15}$, and
wherein said heteroaryl group is selected from the group consisting of:
thienyl, furanyl, pyrrolyl, oxazolyl, thiazolyl, imidazolyl, pyrazolyl, isoxazolyl, isothiazolyl, oxadiazolyl, triazolyl, tetrazolyl, thiadiazolyl, thia-4H-pyrazolyl, pyridinyl, pyridazinyl, pyrimidinyl, pyrazinyl, and triazinyl,
or a stereoisomer, a tautomer, an N-oxide, a hydrate, a solvate, or a salt thereof, or a mixture of any of the foregoing.

5. The compound according to claim 1, wherein:
$R^5$ is a phenyl or heteroaryl group,
wherein said phenyl or heteroaryl group is optionally substituted with one or more substituents independently selected from the group consisting of:
halo-, cyano, $C_1$-$C_6$-alkyl, $C_3$-$C_6$-cycloalkyl, $C_1$-$C_6$-haloalkyl, $C_1$-$C_6$-haloalkoxy, nitro, $R^{13}O$—, $R^{13}S$—, $R^{13}OC(=O)$—($C_1$-$C_6$-alkyl)-, $R^{13}OC(=O)$—($C_2$-$C_6$-alkenyl)-, $R^{13}OC(=O)$—($C_1$-$C_6$-alkoxy)-, $R^{14}(R^{15})NC(=O)$—($C_1$-$C_6$-alkyl)-, $R^{14}(R^{15})NC(=O)$—($C_2$-$C_6$-alkenyl)-, $R^{14}(R^{15})NC(=O)$—($C_1$-$C_6$-alkoxy)-, ($C_1$-$C_6$-alkyl)-S—, ($C_1$-$C_6$-alkyl)-S(=O)—, ($C_1$-$C_6$-alkyl)-S(=O)$_2$—, ($C_1$-$C_6$-haloalkyl)-S—, —C(=O)$OR^{13}$, —C(=O)N($R^{14}$)$R^{15}$, —C(=O)N($R^{14}$)S(=O)$_2R^{16}$, —N($R^4$)$R^{15}$, —N($R^{14}$)C(=O)$R^{16}$, —N($R^{14}$)C(=O)$R^{17}$, —N($R^{14}$)S(=O)$_2R^{16}$, —S(=O)$_2OR^{13}$, and —S(=O)$_2$N($R^{14}$)$R^{15}$, and
wherein said heteroaryl group is selected from the group consisting of:
oxazolyl, pyrazolyl, oxadiazolyl, triazolyl, tetrazolyl, and pyridinyl,
or a stereoisomer, a tautomer, an N-oxide, a hydrate, a solvate, or a salt thereof, or a mixture of any of the foregoing.

6. The compound according to claim 1, wherein:
$R^5$ is a phenyl or heteroaryl group,
wherein said phenyl or heteroaryl group is optionally substituted with one or more substituents independently selected from the group consisting of:
halo-, $C_1$-$C_6$-alkyl, $C_1$-$C_6$-haloalkyl, $R^{13}O$—, —C(=O)$OR^{13}$, and —C(=O)N($R^{14}$)$R^{15}$, and
wherein said heteroaryl group is selected from the group consisting of:
thienyl, furanyl, pyrrolyl, oxazolyl, thiazolyl, imidazolyl, pyrazolyl, isoxazolyl, isothiazolyl, oxadiazolyl, triazolyl, tetrazolyl, thiadiazolyl, thia-4H-pyrazolyl, pyridinyl, pyridazinyl, pyrimidinyl, pyrazinyl, and triazinyl,
or a stereoisomer, a tautomer, an N-oxide, a hydrate, a solvate, or a salt thereof, or a mixture of any of the foregoing.

7. The compound according to claim 1, wherein:
$R^5$ is a phenyl or heteroaryl group,
wherein said phenyl or heteroaryl group is optionally substituted with one or more substituents independently selected from the group consisting of:
halo-, $C_1$-$C_6$-alkyl, $C_1$-$C_6$-haloalkyl, $R^{13}O$—, —C(=O)$OR^{13}$, and —C(=O)N($R^{14}$)$R^{15}$, and
wherein said heteroaryl group is selected from the group consisting of:
oxazolyl, pyrazolyl, oxadiazolyl, triazolyl, tetrazolyl, and pyridinyl,
or a stereoisomer, a tautomer, an N-oxide, a hydrate, a solvate, or a salt thereof, or a mixture of any of the foregoing.

8. The compound according to claim 1, wherein:
$R^6$ is a hydrogen atom, a halogen atom, or a group selected from the group consisting of $C_1$-$C_3$-alkyl and $C_1$-$C_3$-alkoxy,
or a stereoisomer, a tautomer, an N-oxide, a hydrate, a solvate, or a salt thereof, or a mixture of any of the foregoing.

9. The compound according to claim 1, wherein:
$R^6$ is a hydrogen atom or a methyl group,
or a stereoisomer, a tautomer, an N-oxide, a hydrate, a solvate, or a salt thereof, or a mixture of any of the foregoing.

10. The compound according to claim 1, wherein:
$R^8$ is a methyl group;
$R^9$ is a hydrogen atom;
$R^{10}$ is a methyl group, and
$R^{11}$ is a methyl group,
or a stereoisomer, a tautomer, an N-oxide, a hydrate, a solvate, or a salt thereof, or a mixture of any of the foregoing.

11. The compound according to claim 1, wherein:
$R^8$ is a methyl group, $R^9$ is a methyl group,
$R^{10}$ is a methyl group, and
$R^{11}$ is a methyl group,
or a stereoisomer, a tautomer, an N-oxide, a hydrate, a solvate, or a salt thereof, or a mixture of any of the foregoing.

12. The compound according to claim 1, wherein:
$R^{13}$ is a hydrogen atom or a $C_1$-$C_3$-alkyl group,
or a stereoisomer, a tautomer, an N-oxide, a hydrate, a solvate, or a salt thereof, or a mixture of any of the foregoing.

13. The compound according to claim 1, wherein:
$R^{14}$ and $R^{15}$ are independently selected from the group consisting of:
hydrogen, $C_1$-$C_6$-alkyl, and $C_3$-$C_6$-cycloalkyl,
or a stereoisomer, a tautomer, an N-oxide, a hydrate, a solvate, or a salt thereof, or a mixture of any of the foregoing.

14. The compound according to claim 1, wherein:
$R^{14}$ is a hydrogen atom; and
$R^{15}$ is a hydrogen atom,
or a stereoisomer, a tautomer, an N-oxide, a hydrate, a solvate, or a salt thereof, or a mixture of any of the foregoing.

15. The compound according to claim 1, which is selected from the group consisting of:
5-(3,5-dimethyl-1,2-oxazol-4-yl)-N-[4-(trifluoromethoxy)phenyl]-1-(3,3,5-trimethylcyclohexyl)-1H-benzimidazol-2-amine;

5-(3,5-dimethyl-1,2-oxazol-4-yl)-N-[4-(trifluoromethoxy)phenyl]-1-[(1R,5R)-3,3,5-trimethylcyclohexyl]-1H-benzimidazol-2-amine;

5-(3,5-dimethyl-1,2-oxazol-4-yl)-N-[4-(trifluoromethoxy)phenyl]-1-[(1S,5S)-3,3,5-trimethylcyclohexyl]-1H-benzimidazol-2-amine;

3-[2-{[4-(trifluoromethoxy)phenyl]amino}-1-(3,3,5-trimethylcyclohexyl)-1H-benzimidazol-5-yl]benzoic acid;

3-(2-{[4-(trifluoromethoxy)phenyl]amino}-1-[(1R,5R)-3,3,5-trimethylcyclohexyl]-1H-benzimidazol-5-yl)benzoic acid;

3-(2-{[4-(trifluoromethoxy)phenyl]amino}-1-[(1 S,5S)-3,3,5-trimethylcyclohexyl]-1H-benzimidazol-5-yl)benzoic acid;

4-[2-{[4-(trifluoromethoxy)phenyl]amino}-1-(3,3,5-trimethylcyclohexyl)-1H-benzimidazol-5-yl]benzoic acid;

4-(2-{[4-(trifluoromethoxy)phenyl]amino}-1-[(1R,5R)-3,3,5-trimethylcyclohexyl]-1H-benzimidazol-5-yl)benzoic acid;

4-(2-{[4-(trifluoromethoxy)phenyl]amino}-1-[(1 S,5S)-3,3,5-trimethylcyclohexyl]-1H-benzimidazol-5-yl)benzoic acid;

5-(1H-pyrazol-4-yl)-N-[4-(trifluoromethoxy)phenyl]-1-(3,3,5-trimethylcyclohexyl)-1H-benzimidazol-2-amine;

5-(1H-pyrazol-4-yl)-N-[4-(trifluoromethoxy)phenyl]-1-[(1R,5R)-3,3,5-trimethylcyclohexyl]-1H-benzimidazol-2-amine;

5-(1H-pyrazol-4-yl)-N-[4-(trifluoromethoxy)phenyl]-1-[(1 S,5S)-3,3,5-trimethylcyclohexyl]-1H-benzimidazol-2-amine;

5-(3,5-dimethyl-1H-pyrazol-4-yl)-N-[4-(trifluoromethoxy)phenyl]-1-(3,3,5-trimethylcyclohexyl)-1H-benzimidazol-2-amine;

5-(3,5-dimethyl-1H-pyrazol-4-yl)-N-[4-(trifluoromethoxy)phenyl]-1-[(1R,5R)-3,3,5-trimethylcyclohexyl]-1H-benzimidazol-2-amine;

5-(3,5-dimethyl-1H-pyrazol-4-yl)-N-[4-(trifluoromethoxy)phenyl]-1-[(1S,5S)-3,3,5-trimethylcyclohexyl]-1H-benzimidazol-2-amine;

5-(1,3-dimethyl-1H-pyrazol-5-yl)-N-[4-(trifluoromethoxy)phenyl]-1-(3,3,5-trimethylcyclohexyl)-1H-benzimidazol-2-amine;

5-(1,3-dimethyl-1H-pyrazol-5-yl)-N-[4-(trifluoromethoxy)phenyl]-1-[(1R,5R)-3,3,5-trimethylcyclohexyl]-1H-benzimidazol-2-amine;

5-(1,3-dimethyl-1H-pyrazol-5-yl)-N-[4-(trifluoromethoxy)phenyl]-1-[(1S,5S)-3,3,5-trimethylcyclohexyl]-1H-benzimidazol-2-amine;

5-(3-methyl-1H-pyrazol-4-yl)-N-[4-(trifluoromethoxy)phenyl]-1-(3,3,5-trimethylcyclohexyl)-1H-benzimidazol-2-amine;

5-(3-methyl-1H-pyrazol-4-yl)-N-[4-(trifluoromethoxy)phenyl]-1-[(1R,5R)-3,3,5-trimethylcyclohexyl]-1H-benzimidazol-2-amine;

5-(3-methyl-1H-pyrazol-4-yl)-N-[4-(trifluoromethoxy)phenyl]-1-[(1 S,5S)-3,3,5-trimethylcyclohexyl]-1H-benzimidazol-2-amine;

5-(1H-pyrazol-5-yl)-N-[4-(trifluoromethoxy)phenyl]-1-(3,3,5-trimethylcyclohexyl)-1H-benzimidazol-2-amine;

5-(1H-pyrazol-5-yl)-N-[4-(trifluoromethoxy)phenyl]-1-[(1R,5R)-3,3,5-trimethylcyclohexyl]-1H-benzimidazol-2-amine;

5-(1H-pyrazol-5-yl)-N-[4-(trifluoromethoxy)phenyl]-1-[(1 S,5S)-3,3,5-trimethylcyclohexyl]-1H-benzimidazol-2-amine;

5-(1,2-oxazol-4-yl)-N-[4-(trifluoromethoxy)phenyl]-1-(3,3,5-trimethylcyclohexyl)-1H-benzimidazol-2-amine;

5-(1,2-oxazol-4-yl)-N-[4-(trifluoromethoxy)phenyl]-1-[(1R,5R)-3,3,5-trimethylcyclohexyl]-1H-benzimidazol-2-amine;

5-(1,2-oxazol-4-yl)-N-[4-(trifluoromethoxy)phenyl]-1-[(1 S,5S)-3,3,5-trimethylcyclohexyl]-1H-benzimidazol-2-amine;

5-(3,5-dimethyl-1H-pyrazol-4-yl)-N-{4-[(trifluoromethyl)sulfanyl]phenyl}-1-(3,3,5-trimethylcyclohexyl)-1H-benzimidazol-2-amine;

5-(3,5-dimethyl-1H-pyrazol-4-yl)-N-{4-[(trifluoromethyl)sulfanyl]phenyl}-1-[(1R,5R)-3,3,5-trimethylcyclohexyl]-1H-benzimidazol-2-amine;

5-(3,5-dimethyl-1H-pyrazol-4-yl)-N-{4-[(trifluoromethyl)sulfanyl]phenyl}-1-[(1S,5S)-3,3,5-trimethylcyclohexyl]-1H-benzimidazol-2-amine;

3-[2-{[4-(trifluoromethoxy)phenyl]amino}-1-(3,3,5-trimethylcyclohexyl)-1H-benzimidazol-5-yl]benzamide;

3-(2-{[4-(trifluoromethoxy)phenyl]amino}-1-[(1R,5R)-3,3,5-trimethylcyclohexyl]-1H-benzimidazol-5-yl)benzamide;

3-(2-{[4-(trifluoromethoxy)phenyl]amino}-1-[(1 S,5S)-3,3,5-trimethylcyclohexyl]-1H-benzimidazol-5-yl)benzamide;

5-(1,3-dimethyl-1H-pyrazol-5-yl)-N-[4-(trifluoromethoxy)phenyl]-1-(3,3,5-trimethylcyclohexyl)-1H-benzimidazol-2-amine;

5-(1,3-dimethyl-1H-pyrazol-5-yl)-N-[4-(trifluoromethoxy)phenyl]-1-[(1R,5R)-3,3,5-trimethylcyclohexyl]-1H-benzimidazol-2-amine;

5-(1,3-dimethyl-1H-pyrazol-5-yl)-N-[4-(trifluoromethoxy)phenyl]-1-[(1S,5S)-3,3,5-trimethylcyclohexyl]-1H-benzimidazol-2-amine;

5-(1-methyl-1H-pyrazol-4-yl)-N-[4-(trifluoromethoxy)phenyl]-1-(3,3,5-trimethylcyclohexyl)-1H-benzimidazol-2-amine;

5-(1-methyl-1H-pyrazol-4-yl)-N-[4-(trifluoromethoxy)phenyl]-1-[(1R,5R)-3,3,5-trimethylcyclohexyl]-1H-benzimidazol-2-amine;

5-(1-methyl-1H-pyrazol-4-yl)-N-[4-(trifluoromethoxy)phenyl]-1-[(1 S,5S)-3,3,5-trimethylcyclohexyl]-1H-benzimidazol-2-amine;

5-(2-methoxypyridin-4-yl)-N-[4-(trifluoromethoxy)phenyl]-1-(3,3,5-trimethylcyclohexyl)-1H-benzimidazol-2-amine;

5-(2-methoxypyridin-4-yl)-N-[4-(trifluoromethoxy)phenyl]-1-[(1R,5R)-3,3,5-trimethylcyclohexyl]-1H-benzimidazol-2-amine;

5-(2-methoxypyridin-4-yl)-N-[4-(trifluoromethoxy)phenyl]-1-[(1 S,5S)-3,3,5-trimethylcyclohexyl]-1H-benzimidazol-2-amine;

methyl 3-[2-{[4-(trifluoromethoxy)phenyl]amino}-1-(3,3,5-trimethylcyclohexyl)-1H-benzimidazol-5-yl]benzoate;

methyl 3-(2-{[4-(trifluoromethoxy)phenyl]amino}-1-[(1R,5R)-3,3,5-trimethylcyclohexyl]-1H-benzimidazol-5-yl)benzoate;

methyl 3-(2-{[4-(trifluoromethoxy)phenyl]amino}-1-[(1 S,5S)-3,3,5-trimethylcyclohexyl]-1H-benzimidazol-5-yl)benzoate;

5-[1-methyl-3-(trifluoromethyl)-1H-pyrazol-4-yl]-N-[4-(trifluoromethoxy)phenyl]-1-(3,3,5-trimethylcyclohexyl)-1H-benzimidazol-2-amine;

5-[1-methyl-3-(trifluoromethyl)-1H-pyrazol-4-yl]-N-[4-(trifluoromethoxy)phenyl]-1-[(1R,5R)-3,3,5-trimethylcyclohexyl]-1H-benzimidazol-2-amine;

5-[1-methyl-3-(trifluoromethyl)-1H-pyrazol-4-yl]-N-[4-(trifluoromethoxy)phenyl]-1-[(1 S, 5S)-3,3,5-trimethylcyclohexyl]-1H-benzimidazol-2-amine;

4-[2-{[4-(trifluoromethoxy)phenyl]amino}-1-(3,3,5-trimethylcyclohexyl)-1H-benzimidazol-5-yl]benzamide;

4-(2-{[4-(trifluoromethoxy)phenyl]amino}-1-[(1R,5R)-3,3,5-trimethylcyclohexyl]-1H-benzimidazol-5-yl)benzamide;

4-(2-{[4-(trifluoromethoxy)phenyl]amino}-1-[(1 S,5S)-3,3,5-trimethylcyclohexyl]-1H-benzimidazol-5-yl]benzamide;

methyl 4-[2-{[4-(trifluoromethoxy)phenyl]amino}-1-(3,3,5-trimethylcyclohexyl)-1H-benzimidazol-5-yl]benzoate;

methyl 4-(2-{[4-(trifluoromethoxy)phenyl]amino}-1-[(1R,5R)-3,3,5-trimethylcyclohexyl]-1H-benzimidazol-5-yl)benzoate;

methyl 4-(2-{[4-(trifluoromethoxy)phenyl]amino}-1-[(1 S,5S)-3,3,5-trimethylcyclohexyl]-1H-benzimidazol-5-yl)benzoate;

N-[4-(trifluoromethoxy)phenyl]-1-(3,3,5-trimethylcyclohexyl)-5-(1,3,5-trimethyl-1H-pyrazol-4-yl)-1H-benzimidazol-2-amine;

N-[4-(trifluoromethoxy)phenyl]-1-[(1R,5R)-3,3,5-trimethylcyclohexyl]-5-(1,3,5-trimethyl-1H-pyrazol-4-yl)-1H-benzimidazol-2-amine;

N-[4-(trifluoromethoxy)phenyl]-1-[(1 S, 5S)-3,3,5-trimethylcyclohexyl]-5-(1,3,5-trimethyl-1H-pyrazol-4-yl)-1H-benzimidazol-2-amine;

5-(1-methyl-1H-pyrazol-5-yl)-N-[4-(trifluoromethoxy)phenyl]-1-(3,3,5-trimethylcyclohexyl)-1H-benzimidazol-2-amine;

5-(1-methyl-1H-pyrazol-5-yl)-N-[4-(trifluoromethoxy)phenyl]-1-[(1R,5R)-3,3,5-trimethylcyclohexyl]-1H-benzimidazol-2-amine;

5-(1-methyl-1H-pyrazol-5-yl)-N-[4-(trifluoromethoxy)phenyl]-1-[(1 S,5S)-3,3,5-trimethylcyclohexyl]-1H-benzimidazol-2-amine;

5-(3,5-dimethyl-1,2-oxazol-4-yl)-N-{4-[(trifluoromethyl)sulfanyl]phenyl}-1-(3,3,5-trimethylcyclohexyl)-1H-benzimidazol-2-amine;

5-(3,5-dimethyl-1,2-oxazol-4-yl)-N-{4-[(trifluoromethyl)sulfanyl]phenyl}-1-[(1R,5R)-3,3,5-trimethylcyclohexyl]-1H-benzimidazol-2-amine;

5-(3,5-dimethyl-1,2-oxazol-4-yl)-N-{4-[(trifluoromethyl)sulfanyl]phenyl}-1-[(1 S,5S)-3,3,5-trimethylcyclohexyl]-1H-benzimidazol-2-amine;

5-(1H-pyrazol-5-yl)-N-{4-[(trifluoromethyl)sulfanyl]phenyl}-1-(3,3,5-trimethylcyclohexyl)-1H-benzimidazol-2-amine;

5-(1H-pyrazol-5-yl)-N-{4-[(trifluoromethyl)sulfanyl]phenyl}-1-[(1R,5R)-3,3,5-trimethylcyclohexyl]-1H-benzimidazol-2-amine;

5-(1H-pyrazol-5-yl)-N-{4-[(trifluoromethyl)sulfanyl]phenyl}-1-[(1 S,5S)-3,3,5-trimethylcyclohexyl]-1H-benzimidazol-2-amine;

5-(3,5-dimethyl-1,2-oxazol-4-yl)-N-[4-(trifluoromethyl)phenyl]-1-(3,3,5-trimethylcyclohexyl)-1H-benzimidazol-2-amine;

5-(3,5-dimethyl-1,2-oxazol-4-yl)-N-[4-(trifluoromethyl)phenyl]-1-[(1R,5R)-3,3,5-trimethylcyclohexyl]-1H-benzimidazol-2-amine;

5-(3,5-dimethyl-1,2-oxazol-4-yl)-N-[4-(trifluoromethyl)phenyl]-1-[(1S,5S)-3,3,5-trimethylcyclohexyl]-1H-benzimidazol-2-amine;

5-(3,5-dimethyl-1H-pyrazol-4-yl)-N-[4-(trifluoromethyl)phenyl]-1-(3,3,5-trimethylcyclohexyl)-1H-benzimidazol-2-amine;

5-(3,5-dimethyl-1H-pyrazol-4-yl)-N-[4-(trifluoromethyl)phenyl]-1-[(1R,5R)-3,3,5-trimethylcyclohexyl]-1H-benzimidazol-2-amine;

5-(3,5-dimethyl-1H-pyrazol-4-yl)-N-[4-(trifluoromethyl)phenyl]-1-[(1S,5S)-3,3,5-trimethylcyclohexyl]-1H-benzimidazol-2-amine;

5-(5-Methyl-1,3,4-oxadiazol-2-yl)-1-(3,3,5,5-tetramethylcyclohexyl)-N-[4-(trifluoromethoxy)phenyl]-1H-benzimidazol-2-amine;

5-(5-Methyl-1,2,4-oxadiazol-3-yl)-1-(3,3,5,5-tetramethylcyclohexyl)-N-[4-(trifluoromethoxy)phenyl]-1H-benzimidazol-2-amine;

5-(1H-tetrazol-5-yl)-N-[4-(trifluoromethoxy)phenyl]-1-(3,3,5-trimethylcyclohexyl)-1H-benzimidazol-2-amine;

5-(1H-tetrazol-5-yl)-N-[4-(trifluoromethoxy)phenyl]-1-[(1R,5S)-3,3,5-trimethylcyclohexyl]-1H-benzimidazol-2-amine;

5-(1H-tetrazol-5-yl)-N-[4-(trifluoromethoxy)phenyl]-1-[(1 S,5S)-3,3,5-trimethylcyclohexyl]-1H-benzimidazol-2-amine;

1-(3,3,5,5-tetramethylcyclohexyl)-5-(1H-tetrazol-5-yl)-N-[4-(trifluoromethoxy)phenyl]-1H-benzimidazol-2-amine;

5-(3,5-dimethyl-1H-pyrazol-4-yl)-6-methyl-1-(3,3,5,5-tetramethylcyclohexyl)-N-[4-(trifluoromethoxy)phenyl]-1H-benzimidazol-2-amine;

6-methyl-5-(5-methyl-4H-1,2,4-triazol-3-yl)-1-(3,3,5,5-tetramethylcyclohexyl)-N-[4-(trifluoromethoxy)phenyl]-1H-benzimidazol-2-amine;

5-(5-methyl-1,3,4-oxadiazol-2-yl)-N-[4-(trifluoromethoxy)phenyl]-1-(3,3,5-trimethylcyclohexyl)-1H-benzimidazol-2-amine;

5-(5-methyl-1,3,4-oxadiazol-2-yl)-N-[4-(trifluoromethoxy)phenyl]-1-[(1R,5R)-3,3,5-trimethylcyclohexyl]-1H-benzimidazol-2-amine;

5-(5-methyl-1,3,4-oxadiazol-2-yl)-N-[4-(trifluoromethoxy)phenyl]-1-[(1S,5S)-3,3,5-trimethylcyclohexyl]-1H-benzimidazol-2-amine;

5-(3,5-difluoro-4-methoxyphenyl)-N-[4-(trifluoromethoxy)phenyl]-1-(3,3,5-trimethylcyclohexyl)-1H-benzimidazol-2-amine;

5-(3,5-difluoro-4-methoxyphenyl)-N-[4-(trifluoromethoxy)phenyl]-1-[(1R,5R)-3,3,5-trimethylcyclohexyl]-1H-benzimidazol-2-amine;

5-(3,5-difluoro-4-methoxyphenyl)-N-[4-(trifluoromethoxy)phenyl]-1-[(1 S,5S)-3,3,5-trimethylcyclohexyl]-1H-benzimidazol-2-amine;

2,6-difluoro-4-[2-{[4-(trifluoromethoxy)phenyl]amino}-1-(3,3,5-trimethylcyclohexyl)-1H-benzimidazol-5-yl]phenol;

2,6-difluoro-4-(2-{[4-(trifluoromethoxy)phenyl]amino}-1-[(1R,5R)-3,3,5-trimethylcyclohexyl]-1H-benzimidazol-5-yl)phenol;

2,6-difluoro-4-(2-{[4-(trifluoromethoxy)phenyl]amino}-1-[(1 S,5S)-3,3,5-trimethylcyclohexyl]-1H-benzimidazol-5-yl)phenol;

2,6-dimethyl-4-[2-{[4-(trifluoromethoxy)phenyl]amino}-1-(3,3,5-trimethylcyclohexyl)-1H-benzimidazol-5-yl]phenol;

2,6-dimethyl-4-(2-{[4-(trifluoromethoxy)phenyl]amino}-1-[(1R,5R)-3,3,5-trimethylcyclohexyl]-1H-benzimidazol-5-yl)phenol;

2,6-dimethyl-4-(2-{[4-(trifluoromethoxy)phenyl]amino}-1-[(1S,5S)-3,3,5-trimethylcyclohexyl]-1H-benzimidazol-5-yl)phenol;

5-(3-ethoxy-5-methyl-1,2-oxazol-4-yl)-N-[4-(trifluoromethoxy)phenyl]-1-(3,3,5-trimethylcyclohexyl)-1H-benzimidazol-2-amine;

5-(3-ethoxy-5-methyl-1,2-oxazol-4-yl)-N-[4-(trifluoromethoxy)phenyl]-1-[(1R,5R)-3,3,5-trimethylcyclohexyl]-1H-benzimidazol-2-amine;

5-(3-ethoxy-5-methyl-1,2-oxazol-4-yl)-N-[4-(trifluoromethoxy)phenyl]-1-[(1S,5S)-3,3,5-trimethylcyclohexyl]-1H-benzimidazol-2-amine;

5-[6-methyl-1-(3,3,5,5-tetramethylcyclohexyl)-2-{[4-(trifluoromethoxy)phenyl]amino}-1H-benzimidazol-5-yl]-1,3-oxazolidine-2,4-dione; and 5-[6-methyl-1-(3,3,5,5-tetramethylcyclohexyl)-2-{[4-(trifluoromethoxy)phenyl]amino}-1H-benzimidazol-5-yl]-1,2-oxazol-3-ol, or a stereoisomer, a tautomer, an N-oxide, a hydrate, a solvate, or a salt thereof, or a mixture of any of the foregoing.

16. A method of preparing the compound of formula (I) according to claim 1, comprising reacting an intermediate compound of formula (VI):

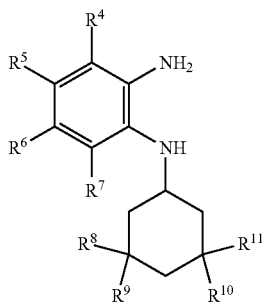

(VI)

wherein $R^4$, $R^5$, $R^6$, $R^7$, $R^8$, $R^9$, $R^{10}$ and $R^{11}$ are as defined for the compound of formula (I) according to claim 1, with a compound of formula (III):

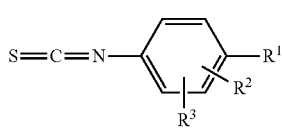

(III)

wherein $R^1$, $R^2$ and $R^3$ are as defined for the compound of formula (I) according to claim 1, to give the compound of formula (I):

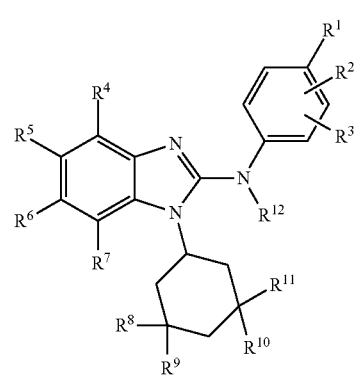

(I)

wherein $R^1$, $R^2$, $R^3$, $R^4$, $R^5$, $R^6$, $R^7$, $R^8$, $R^9$, $R^{10}$, $R^{11}$ and $R^{12}$ are as defined for the compound of formula (I) according to claim 1.

17. A method of preparing the compound of formula (I) according to claim 1, comprising reacting an intermediate compound of formula (IV):

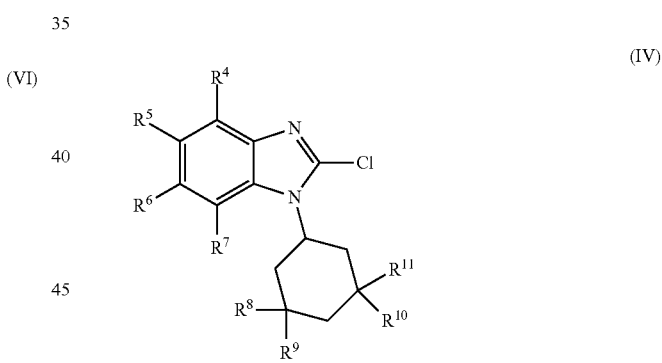

(IV)

wherein $R^4$, $R^5$, $R^6$, $R^7$, $R^8$, $R^9$, $R^{10}$ and $R^{11}$ are as defined for the compound of formula (I) according to claim 1, with a compound of formula (V):

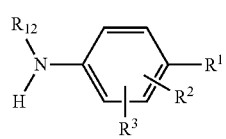

(V)

wherein $R^1$, $R^2$, $R^3$ and $R^{12}$ are as defined for the compound of formula (I) according to claim 1, to give the compound of formula (I):

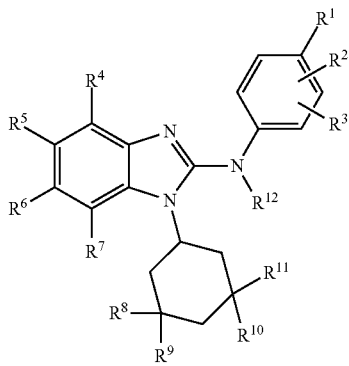

wherein $R^1$, $R^2$, $R^3$, $R^4$, $R^5$, $R^6$, $R^7$, $R^8$, $R^9$, $R^{10}$, $R^{11}$ and $R^{12}$ are as defined for the compound of formula (I) according to claim 1.

18. A method of preparing the compound of formula (I) according to claim 1, comprising reacting an intermediate compound of formula (II):

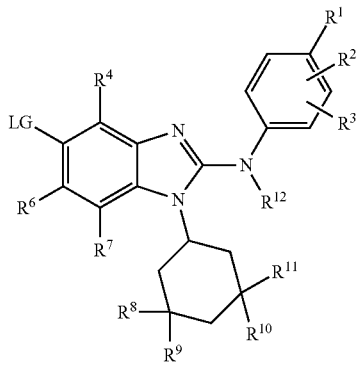

wherein $R^4$, $R^6$, $R^7$, $R^8$, $R^9$, $R^{10}$, $R^{11}$ and $R^{12}$ are as defined for the compound of formula (I) according to claim 1, and LG is a leaving group, with a compound of formula (VII):

$$R^5—Y \qquad (VII)$$

wherein $R^5$ is as defined as for the compound of formula (I) according to claim 1 and Y is a group enabling palladium catalysed coupling reactions, to give the compound of formula (I):

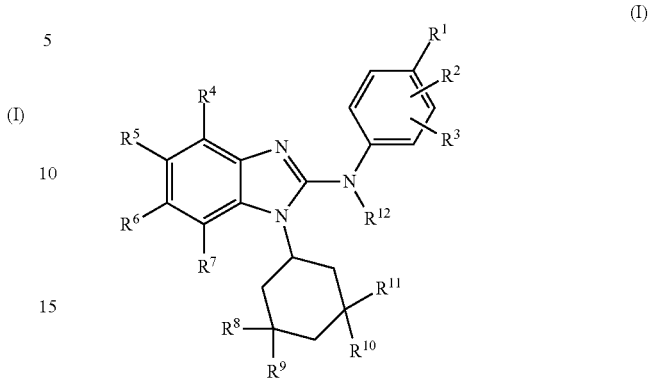

wherein $R^1$, $R^2$, $R^3$, $R^4$, $R^5$, $R^6$, $R^7$, $R^8$, $R^{10}$, $R^{11}$ and $R^{12}$ are as defined for the compound of formula (I) according to claim 1.

19. A pharmaceutical composition comprising the compound of formula (I) according to claim 1, or a stereoisomer, a tautomer, an N-oxide, a hydrate, a solvate, or a salt thereof, or a mixture of any of the foregoing, and a pharmaceutically acceptable diluent or carrier.

20. A pharmaceutical combination comprising:
one or more first active ingredients selected from the compound of formula (I) according to claim 1, or a stereoisomer, a tautomer, an N-oxide, a hydrate, a solvate, or a salt thereof, or a mixture of any of the foregoing; and
one or more second active ingredients selected from chemotherapeutic anti-cancer agents.

21. A method for treatment of a disease responsive to inhibition of mIDH1 activity, comprising administering to a patient in need thereof a pharmaceutically effective amount of the compound of formula (I) according to claim 1, or a stereoisomer, a tautomer, an N-oxide, a hydrate, a solvate, or a salt thereof, or a mixture of any of the foregoing.

22. The method according to claim 21, wherein said disease responsive to inhibition of mIDH1 activity is a disease of uncontrolled cell growth, proliferation and/or survival, an inappropriate cellular immune response, or an inappropriate cellular inflammatory response.

23. The method according to claim 21, wherein said disease responsive to inhibition of mIDH1 activity is a haematological tumour, a solid tumour, or metastases thereof.

24. The method according to claim 21, wherein said disease responsive to inhibition of mIDH1 activity is leukaemia, myelodysplastic syndrome, malignant lymphoma, a head and neck tumour, a brain tumour, a tumour of the thorax, a non-small cell lung tumour, a small cell lung tumour, a gastrointestinal tumour, an endocrine tumour, a mammary tumour, a gynaecological tumour, a urological tumour, a renal tumour, a bladder tumour, a prostate tumour, a skin tumour, sarcoma, or metastases thereof.

25. The compound of claim 1 or a salt thereof.
26. The compound of claim 15 or a salt thereof.
27. The pharmaceutical composition of claim 19, comprising the compound of formula (I) or a salt thereof.
28. The pharmaceutical combination of claim 20, comprising the compound of formula (I) or a salt thereof.
29. The method of claim 21, comprising administering the compound of formula (I) or a salt thereof.

* * * * *